US011077301B2

(12) United States Patent
Creasey et al.

(10) Patent No.: US 11,077,301 B2
(45) Date of Patent: Aug. 3, 2021

(54) TOPICAL NERVE STIMULATOR AND SENSOR FOR BLADDER CONTROL

(71) Applicant: Neurostim OAB, Inc., Waltham, MA (US)

(72) Inventors: Graham Creasey, Menlo Park, CA (US); Hoo-Min D Toong, Cambridge, MA (US)

(73) Assignee: NeurostimOAB, Inc., Waltham, MA (US)

(*) Notice: Subject to any disclaimer, the term of this patent is extended or adjusted under 35 U.S.C. 154(b) by 0 days.

(21) Appl. No.: 15/048,760

(22) Filed: Feb. 19, 2016

(65) Prior Publication Data

US 2017/0281938 A1 Oct. 5, 2017

Related U.S. Application Data

(63) Continuation-in-part of application No. 14/893,946, filed on Nov. 25, 2015, now Pat. No. 10,016,600.
(Continued)

(51) Int. Cl.
A61N 1/36 (2006.01)
A61B 5/00 (2006.01)
(Continued)

(52) U.S. Cl.
CPC .......... A61N 1/36007 (2013.01); A61B 5/204 (2013.01); A61B 5/205 (2013.01);
(Continued)

(58) Field of Classification Search
CPC ................ A61N 1/0551; A61N 1/3787; A61N 1/36139; A61N 1/37229; A61N 1/36125;
(Continued)

(56) References Cited

U.S. PATENT DOCUMENTS 4,277,980 A 7/1981 Coats et al.
4,532,930 A 8/1985 Crosby et al.
(Continued)

FOREIGN PATENT DOCUMENTS

CN 101868279 A 10/2010
CN 107362447 A 11/2017
(Continued)

OTHER PUBLICATIONS

US 8,398,630 B2, 03/2013, Demarais et al. (withdrawn)
(Continued)

Primary Examiner — Deborah L Malamud
(74) Attorney, Agent, or Firm — Potomac Law Group, PLLC

(57) ABSTRACT

What is provided is a method and apparatus for modifying bladder function comprising: applying a dermal patch having an integral electrode in proximity to a sacral or pudendal nerve; selecting the sacral or pudendal nerve by a sensor integral on the dermal patch; determining a stimulation corresponding to the sacral or pudendal nerve, by logic of the dermal patch; applying the stimulation by the electrodes and a stimulator integral to the dermal patch to produce an electric field; and selectively activating the sacral or pudendal nerve by the electric field.

20 Claims, 8 Drawing Sheets

Related U.S. Application Data

(60) Provisional application No. 62/119,134, filed on Feb. 21, 2015.

(51) Int. Cl.

| | | |
|---|---|---|
| *A61B 5/20* | (2006.01) | |
| *A61B 8/08* | (2006.01) | |
| *A61N 1/04* | (2006.01) | |
| *A61N 1/02* | (2006.01) | |
| *A61B 5/107* | (2006.01) | |

(52) U.S. Cl.
CPC .......... *A61B 5/4836* (2013.01); *A61B 5/4887* (2013.01); *A61B 5/686* (2013.01); *A61B 8/08* (2013.01); *A61N 1/36014* (2013.01); *A61B 5/1073* (2013.01); *A61B 5/1075* (2013.01); *A61B 5/4893* (2013.01); *A61B 2505/07* (2013.01); *A61B 2505/09* (2013.01); *A61B 2562/0247* (2013.01); *A61N 1/025* (2013.01); *A61N 1/0456* (2013.01); *A61N 1/0492* (2013.01); *A61N 1/36031* (2017.08)

(58) Field of Classification Search
CPC .................. A61N 1/0456; A61N 1/37211; A61N 1/3756; A61N 1/36014; A61N 1/37235; A61N 1/36003; A61N 1/36135; A61N 1/36146; A61N 1/0492; A61N 1/375; A61N 1/36; A61N 1/36132; A61N 1/0484; A61N 1/0452; A61N 1/08; A61N 1/04; A61N 1/0404; A61N 1/0472; A61B 5/4836; A61B 2562/164; A61B 5/11; A61B 5/4519; A61B 5/6833; A61B 5/00; A61B 5/0484; A61B 5/4041; A61B 5/04; A61B 5/6877

See application file for complete search history.

(56) References Cited

U.S. PATENT DOCUMENTS

| | | |
|---|---|---|
| 4,542,753 A | 9/1985 | Brenman et al. |
| 4,549,556 A | 10/1985 | Tarjan et al. |
| 4,553,549 A | 11/1985 | Pope et al. |
| 4,590,949 A | 5/1986 | Pohndorf |
| 4,614,395 A | 9/1986 | Peers-Trevarton |
| 4,658,835 A | 4/1987 | Pohndorf |
| 4,677,989 A | 7/1987 | Robblee |
| 4,690,144 A | 9/1987 | Rise et al. |
| 4,702,254 A | 10/1987 | Zabara |
| 4,706,682 A | 11/1987 | Stypulkowski et al. |
| 4,717,581 A | 1/1988 | Robblee |
| 4,759,228 A | 7/1988 | Butler et al. |
| 4,800,898 A | 1/1989 | Hess et al. |
| 4,817,628 A | 4/1989 | Zealear et al. |
| 4,881,526 A | 11/1989 | Johnson et al. |
| 4,883,666 A | 11/1989 | Sabel et al. |
| 4,919,148 A | 4/1990 | Muccio |
| 4,940,453 A | 7/1990 | Cadwell |
| 4,959,532 A | 9/1990 | Owechko |
| 5,031,621 A | 7/1991 | Grandjean et al. |
| 5,035,242 A | 7/1991 | Franklin et al. |
| 5,047,005 A | 9/1991 | Cadwell |
| 5,092,332 A | 3/1992 | Lee et al. |
| 5,092,835 A | 3/1992 | Schurig et al. |
| 5,095,905 A | 3/1992 | Klepinski |
| 5,211,657 A | 5/1993 | Yamada et al. |
| 5,265,608 A | 11/1993 | Lee et al. |
| 5,381,801 A | 1/1995 | McShane et al. |
| 5,476,494 A | 12/1995 | Edell et al. |
| 5,501,703 A | 3/1996 | Holsheimer et al. |
| 5,569,307 A | 10/1996 | Schulman et al. |
| 5,575,813 A | 11/1996 | Edell et al. |
| 5,584,869 A | 12/1996 | Heck et al. |
| 5,597,381 A | 1/1997 | Rizzo, III |
| 5,603,726 A | 2/1997 | Schulman et al. |
| 5,609,616 A | 3/1997 | Schulman et al. |
| 5,628,769 A | 5/1997 | Saringer |
| 5,643,330 A | 7/1997 | Holsheimer et al. |
| 5,679,340 A | 10/1997 | Chappel |
| 5,713,922 A | 2/1998 | King |
| 5,738,625 A | 4/1998 | Gluck |
| 5,741,314 A | 4/1998 | Daly et al. |
| 5,792,209 A | 8/1998 | Varner |
| 5,795,790 A | 8/1998 | Schinstine et al. |
| 5,824,022 A | 10/1998 | Zilberman et al. |
| 5,830,651 A | 11/1998 | Cauley et al. |
| 5,837,236 A | 11/1998 | Dinsmore |
| 5,853,370 A | 12/1998 | Chance et al. |
| 5,871,534 A | 2/1999 | Messick et al. |
| 5,876,425 A | 3/1999 | Gord et al. |
| 5,891,437 A | 4/1999 | Pietropaolo et al. |
| 5,916,870 A | 6/1999 | Lee et al. |
| 5,921,245 A | 7/1999 | O'Donnell, Jr. |
| 5,922,012 A | 7/1999 | Sakano |
| 5,937,318 A | 8/1999 | Warner, Jr. et al. |
| 5,938,691 A | 8/1999 | Schulman et al. |
| 5,948,428 A | 9/1999 | Lee et al. |
| 5,987,361 A | 11/1999 | Mortimer |
| 5,989,445 A | 11/1999 | Wise et al. |
| 5,992,769 A | 11/1999 | Wise et al. |
| 6,002,960 A | 12/1999 | Sternberger et al. |
| 6,011,018 A | 1/2000 | Crabtree et al. |
| 6,016,449 A | 1/2000 | Fischell et al. |
| 6,058,331 A | 5/2000 | King |
| 6,060,048 A | 5/2000 | Cherksey |
| 6,060,054 A | 5/2000 | Staerz |
| 6,066,084 A | 5/2000 | Edrich et al. |
| 6,067,474 A | 5/2000 | Schulman et al. |
| 6,085,115 A | 7/2000 | Weaver et al. |
| 6,096,537 A | 8/2000 | Chappel |
| 6,119,071 A | 9/2000 | Gorenflo et al. |
| 6,120,538 A | 9/2000 | Rizzo, III et al. |
| 6,140,116 A | 10/2000 | Dinsmore |
| 6,178,349 B1 | 1/2001 | Kieval |
| 6,203,792 B1 | 3/2001 | Filbin |
| 6,204,053 B1 | 3/2001 | Dinsmore |
| 6,258,353 B1 | 7/2001 | Isacson et al. |
| 6,264,950 B1 | 7/2001 | Staerz |
| 6,265,175 B1 | 7/2001 | Gage et al. |
| 6,270,831 B2 | 8/2001 | Kumar et al. |
| 6,277,372 B1 | 8/2001 | Fraser et al. |
| 6,284,245 B1 | 9/2001 | Edge |
| 6,288,527 B1 | 9/2001 | Sugihara et al. |
| 6,294,383 B1 | 9/2001 | Isacson et al. |
| 6,304,784 B1 | 10/2001 | Allee et al. |
| 6,304,787 B1 | 10/2001 | Kuzma et al. |
| 6,359,550 B1 | 3/2002 | Brisebois et al. |
| 6,374,140 B1 | 4/2002 | Rise |
| 6,379,393 B1 | 4/2002 | Mavroidis et al. |
| 6,392,118 B1 | 5/2002 | Hammang et al. |
| 6,392,550 B1 | 5/2002 | Najor |
| 6,393,327 B1 | 5/2002 | Scribner |
| 6,415,186 B1 | 7/2002 | Chim et al. |
| 6,421,232 B2 | 7/2002 | Sallam |
| 6,427,083 B1 | 7/2002 | Owen et al. |
| 6,444,205 B2 | 9/2002 | Dinsmore et al. |
| 6,472,181 B1 | 10/2002 | Mineau-Hanschke |
| 6,510,347 B2 | 1/2003 | Borkan |
| 6,517,833 B2 | 2/2003 | Edge |
| 6,533,732 B1 | 3/2003 | Urmey |
| 6,537,200 B2 | 3/2003 | Leysieffer et al. |
| 6,546,291 B2 | 4/2003 | Merfeld et al. |
| 6,561,975 B1 | 5/2003 | Pool et al. |
| 6,565,503 B2 | 5/2003 | Leysieffer et al. |
| 6,575,894 B2 | 6/2003 | Leysieffer et al. |
| 6,599,695 B2 | 7/2003 | Gage et al. |
| 6,640,118 B2 | 10/2003 | Van Heerden et al. |
| 6,640,121 B1 | 10/2003 | Telischi et al. |
| RE38,323 E | 11/2003 | Sugihara et al. |
| 6,647,297 B2 | 11/2003 | Scribner |
| 6,690,974 B2 | 2/2004 | Archer et al. |
| 6,697,674 B2 | 2/2004 | Leysieffer |

(56) References Cited

U.S. PATENT DOCUMENTS

| | | |
|---|---|---|
| 6,727,696 B2 | 4/2004 | Kruspe et al. |
| 6,744,367 B1 | 6/2004 | Forster |
| 6,788,976 B2 | 9/2004 | Gesotti |
| 6,795,737 B2 | 9/2004 | Gielen et al. |
| 6,807,445 B2 | 10/2004 | Baumann et al. |
| 6,839,596 B2 | 1/2005 | Nelson et al. |
| 6,850,802 B2 | 2/2005 | Holsheimer |
| 6,879,855 B2 | 4/2005 | Schulman et al. |
| 6,884,122 B2 | 4/2005 | Robinson et al. |
| 6,892,097 B2 | 5/2005 | Holsheimer |
| 6,893,812 B2 | 5/2005 | Woltering et al. |
| 6,894,616 B1 | 5/2005 | Forster |
| 6,902,547 B2 | 6/2005 | Aves et al. |
| 6,931,273 B2 | 8/2005 | Groenewegen et al. |
| 6,949,251 B2 | 9/2005 | Dalal et al. |
| 6,970,745 B2 | 11/2005 | Scribner |
| 6,976,998 B2 | 12/2005 | Rizzo et al. |
| 7,001,608 B2 | 2/2006 | Fishman et al. |
| 7,003,335 B2 | 2/2006 | Briancon |
| 7,010,351 B2 | 3/2006 | Firlik et al. |
| 7,027,873 B2 | 4/2006 | Pajunk et al. |
| 7,030,411 B2 | 4/2006 | Krulevitch et al. |
| 7,037,603 B2 | 5/2006 | Lasater |
| 7,047,080 B2 | 5/2006 | Palanker et al. |
| 7,058,455 B2 | 6/2006 | Huie, Jr. et al. |
| 7,079,882 B1 | 7/2006 | Schmidt |
| 7,101,542 B1 | 9/2006 | Vallera et al. |
| 7,106,190 B1 | 9/2006 | Owens |
| 7,107,104 B2 | 9/2006 | Keravel et al. |
| 7,115,071 B1 | 10/2006 | Sunbeck |
| 7,117,034 B2 | 10/2006 | Kronberg |
| 7,120,499 B2 | 10/2006 | Thrope et al. |
| 7,127,301 B1 | 10/2006 | Okandan et al. |
| 7,155,278 B2 | 12/2006 | King et al. |
| 7,167,750 B2 | 1/2007 | Knudson et al. |
| 7,174,223 B2 | 2/2007 | Dalton et al. |
| 7,181,288 B1 | 2/2007 | Rezai et al. |
| 7,191,018 B2 | 3/2007 | Gielen et al. |
| 7,193,414 B2 | 3/2007 | Kruspe et al. |
| 7,206,632 B2 | 4/2007 | King |
| 7,209,787 B2 | 4/2007 | DiLorenzo |
| 7,218,216 B1 | 5/2007 | Uehran |
| 7,218,964 B2 | 5/2007 | Hill et al. |
| 7,228,178 B2 | 6/2007 | Carroll et al. |
| 7,228,727 B2 | 6/2007 | Discenzo |
| 7,239,918 B2 | 7/2007 | Strother et al. |
| 7,249,998 B2 | 7/2007 | van Esbroeck et al. |
| 7,283,867 B2 | 10/2007 | Strother et al. |
| 7,297,420 B2 | 11/2007 | Jiang |
| 7,299,034 B2 | 11/2007 | Kates |
| 7,308,303 B2 | 12/2007 | Whitehurst et al. |
| 7,308,317 B1 | 12/2007 | Okandan et al. |
| 7,333,851 B2 | 2/2008 | Echauz et al. |
| 7,337,004 B2 | 2/2008 | Classen et al. |
| 7,349,169 B2 | 3/2008 | Lee et al. |
| RE40,209 E | 4/2008 | Sugihara et al. |
| 7,376,467 B2 | 5/2008 | Thrope et al. |
| 7,384,145 B2 | 6/2008 | Hetling et al. |
| 7,392,093 B2 | 6/2008 | Khan |
| 7,398,255 B2 | 7/2008 | Lauer et al. |
| 7,415,309 B2 | 8/2008 | McIntyre |
| 7,420,760 B2 | 9/2008 | Zhang et al. |
| 7,422,564 B2 | 9/2008 | Parsons et al. |
| 7,435,443 B2 | 10/2008 | Jiang |
| 7,435,585 B2 | 10/2008 | Tykocinski et al. |
| 7,437,193 B2 | 10/2008 | Parramon et al. |
| 7,437,196 B2 | 10/2008 | Wyler et al. |
| 7,483,747 B2 | 1/2009 | Gliner et al. |
| 7,499,745 B2 | 3/2009 | Littrup et al. |
| 7,499,748 B2 | 3/2009 | Moffitt et al. |
| 7,502,652 B2 | 3/2009 | Gaunt et al. |
| 7,519,419 B2 | 4/2009 | Jiang et al. |
| 7,529,582 B1 | 5/2009 | DiLorenzo |
| 7,553,307 B2 | 6/2009 | Bleich et al. |
| 7,555,343 B2 | 6/2009 | Bleich |
| 7,561,919 B2 | 7/2009 | Shalev et al. |
| 7,565,199 B2 | 7/2009 | Sheffield et al. |
| 7,565,200 B2 | 7/2009 | Wyler et al. |
| 7,571,002 B2 | 8/2009 | Thrope et al. |
| 7,571,006 B2 | 8/2009 | Gordon et al. |
| 7,578,819 B2 | 8/2009 | Bleich et al. |
| 7,584,004 B2 | 9/2009 | Caparso et al. |
| 7,587,238 B2 | 9/2009 | Moffitt et al. |
| 7,598,031 B2 | 10/2009 | Liew |
| 7,599,737 B2 | 10/2009 | Yomtov et al. |
| 7,620,456 B2 | 11/2009 | Gliner et al. |
| 7,622,303 B2 | 11/2009 | Soykan et al. |
| 7,636,597 B2 | 12/2009 | Gross et al. |
| 7,643,874 B2 | 1/2010 | Nitzan et al. |
| 7,657,308 B2 | 2/2010 | Miles et al. |
| 7,658,707 B2 | 2/2010 | Topolev |
| 7,662,558 B2 | 2/2010 | Liew |
| 7,676,274 B2 | 3/2010 | Hung et al. |
| 7,680,526 B2 | 3/2010 | McIntyre et al. |
| 7,684,866 B2 | 3/2010 | Fowler et al. |
| 7,689,285 B2 | 3/2010 | Garabet |
| D613,868 S | 4/2010 | Lhuillery et al. |
| 7,699,768 B2 | 4/2010 | Kishawi et al. |
| 7,704,740 B2 | 4/2010 | Schindler et al. |
| 7,706,888 B2 | 4/2010 | Jolly |
| 7,706,893 B2 | 4/2010 | Hung et al. |
| 7,711,416 B1 | 5/2010 | Akkin et al. |
| 7,715,919 B2 | 5/2010 | Osorio et al. |
| 7,715,924 B2 | 5/2010 | Rezai et al. |
| 7,725,196 B2 | 5/2010 | Machado et al. |
| 7,732,407 B2 | 6/2010 | Hunter |
| 7,738,968 B2 | 6/2010 | Bleich |
| 7,738,969 B2 | 6/2010 | Bleich |
| 7,740,631 B2 | 6/2010 | Bleich et al. |
| 7,747,318 B2 | 6/2010 | John et al. |
| 7,756,583 B2 | 7/2010 | Demarais et al. |
| 7,756,584 B2 | 7/2010 | Sheffield et al. |
| 7,769,462 B2 | 8/2010 | Meadows et al. |
| 7,769,470 B1 | 8/2010 | Rezai et al. |
| 7,798,982 B2 | 9/2010 | Zets et al. |
| 7,799,021 B2 | 9/2010 | Leung et al. |
| 7,801,603 B2 | 9/2010 | Westlund et al. |
| 7,813,809 B2 | 10/2010 | Strother et al. |
| 7,819,801 B2 | 10/2010 | Miles et al. |
| 7,819,869 B2 | 10/2010 | Godara et al. |
| 7,831,305 B2 | 11/2010 | Gliner |
| 7,844,340 B2 | 11/2010 | Pawlowicz, III |
| 7,877,136 B1 | 1/2011 | Moffitt et al. |
| 7,892,180 B2 | 2/2011 | Epley |
| 7,894,911 B2 | 2/2011 | Greenberg et al. |
| 7,894,914 B2 | 2/2011 | Stahmann et al. |
| 7,899,542 B2 | 3/2011 | Cowan et al. |
| 7,914,842 B1 | 3/2011 | Greenberg et al. |
| 7,917,231 B2 | 3/2011 | Farah et al. |
| 7,918,802 B2 | 4/2011 | Urmey |
| 7,922,676 B2 | 4/2011 | Daskal et al. |
| 7,943,632 B2 | 5/2011 | Katzman et al. |
| 7,945,330 B2 | 5/2011 | Gliner et al. |
| 7,947,448 B2 | 5/2011 | Couillard-Despres et al. |
| RE42,449 E | 6/2011 | Forster |
| 7,959,577 B2 | 6/2011 | Schmitz et al. |
| 7,963,915 B2 | 6/2011 | Bleich |
| 7,967,751 B2 | 6/2011 | Goscha et al. |
| 7,974,689 B2 | 7/2011 | Volpe et al. |
| 7,981,144 B2 | 7/2011 | Geist et al. |
| 7,988,688 B2 | 8/2011 | Webb et al. |
| 7,991,475 B1 | 8/2011 | Tang et al. |
| 7,991,480 B2 | 8/2011 | Stahmann et al. |
| 7,992,521 B2 | 8/2011 | Bocquier |
| 8,000,782 B2 | 8/2011 | Gharib et al. |
| 8,000,796 B2 | 8/2011 | Tass et al. |
| 8,000,804 B2 | 8/2011 | Wessendorf et al. |
| 8,010,202 B2 | 8/2011 | Shah et al. |
| 8,014,868 B2 | 9/2011 | Greenberg et al. |
| 8,014,878 B2 | 9/2011 | Greenberg et al. |
| 8,025,632 B2 | 9/2011 | Einarsson |
| 8,027,716 B2 | 9/2011 | Gharib et al. |
| 8,033,996 B2 | 10/2011 | Behar |
| 8,060,210 B1 | 11/2011 | Carroll |

(56) References Cited

U.S. PATENT DOCUMENTS

| | | |
|---|---|---|
| 8,065,012 B2 | 11/2011 | Firlik et al. |
| 8,067,173 B2 | 11/2011 | Liew |
| 8,073,526 B2 | 12/2011 | Graham et al. |
| 8,073,546 B2 | 12/2011 | Sheffield et al. |
| 8,075,556 B2 | 12/2011 | Betts |
| 8,078,252 B2 | 12/2011 | Kipke et al. |
| 8,090,446 B2 | 1/2012 | Fowler et al. |
| 8,092,398 B2 | 1/2012 | Weinberg et al. |
| 8,095,209 B2 | 1/2012 | Flaherty |
| 8,101,358 B2 | 1/2012 | Liew |
| 8,110,358 B2 | 2/2012 | Liew |
| 8,114,019 B2 | 2/2012 | Miles et al. |
| 8,114,597 B2 | 2/2012 | Liew |
| 8,116,875 B2 | 2/2012 | Osypka et al. |
| 8,126,562 B2 | 2/2012 | Fowler et al. |
| 8,131,376 B1 | 3/2012 | Faraji et al. |
| 8,133,674 B2 | 3/2012 | Liew |
| 8,133,675 B2 | 3/2012 | Liew |
| 8,135,472 B2 | 3/2012 | Fowler et al. |
| 8,137,258 B1 | 3/2012 | Dennis et al. |
| 8,137,284 B2 | 3/2012 | Miles et al. |
| 8,140,152 B2 | 3/2012 | John et al. |
| 8,140,162 B1 | 3/2012 | Jiang et al. |
| 8,140,170 B2 | 3/2012 | Rezai et al. |
| 8,148,072 B2 | 4/2012 | Liew |
| 8,155,757 B1 | 4/2012 | Neisz et al. |
| 8,160,713 B2 | 4/2012 | Greenberg et al. |
| 8,162,846 B2 | 4/2012 | Epley |
| 8,165,685 B1 | 4/2012 | Knutson et al. |
| 8,170,676 B2 | 5/2012 | Greenberg et al. |
| 8,174,371 B2 | 5/2012 | Schwieger |
| 8,180,453 B2 | 5/2012 | Greenberg et al. |
| 8,180,460 B2 | 5/2012 | Nevsmith et al. |
| 8,192,357 B2 | 6/2012 | Miles et al. |
| 8,195,300 B2 | 6/2012 | Gliner et al. |
| 8,195,307 B2 | 6/2012 | Vilims |
| 8,200,338 B2 | 6/2012 | Grennberg et al. |
| 8,215,773 B2 | 7/2012 | Gibson-Horn et al. |
| 8,216,135 B2 | 7/2012 | Goscha et al. |
| 8,226,661 B2 | 7/2012 | Balling et al. |
| 8,228,202 B2 | 7/2012 | Buchner et al. |
| 8,239,036 B2 | 8/2012 | Shah et al. |
| 8,255,044 B2 | 8/2012 | Miles et al. |
| 8,257,922 B2 | 9/2012 | Liew |
| 8,260,428 B2 | 9/2012 | Fink et al. |
| 8,260,439 B2 | 9/2012 | DiUbaldi et al. |
| 8,280,516 B2 | 10/2012 | Graupe |
| 8,301,266 B1 | 10/2012 | Zilberman et al. |
| 8,303,516 B2 | 11/2012 | Schmitz et al. |
| 8,308,665 B2 | 11/2012 | Harry et al. |
| 8,313,443 B2 | 11/2012 | Tom |
| 8,323,320 B2 | 12/2012 | Lowry et al. |
| 8,328,354 B2 | 12/2012 | Li et al. |
| 8,332,037 B2 | 12/2012 | Imran |
| 8,332,044 B2 | 12/2012 | McIntyre |
| 8,346,367 B2 | 1/2013 | Carroll |
| 8,352,022 B2 | 1/2013 | Akkin et al. |
| 8,359,083 B2 | 1/2013 | Clark et al. |
| 8,364,257 B2 | 1/2013 | Van Den Eerenbeemd |
| 8,364,258 B2 | 1/2013 | Della Rocca et al. |
| 8,374,698 B2 | 2/2013 | Ok et al. |
| 8,374,701 B2 | 2/2013 | Hyde et al. |
| 8,382,656 B1 | 2/2013 | Brown |
| 8,386,032 B2 | 2/2013 | Bachinski et al. |
| 8,386,053 B2 | 2/2013 | Kornet |
| 8,388,678 B2 | 3/2013 | Singhal et al. |
| 8,391,970 B2 | 3/2013 | Tracey et al. |
| 8,391,986 B2 | 3/2013 | Graupe et al. |
| 8,391,987 B2 | 3/2013 | Faraji et al. |
| 8,396,556 B2 | 3/2013 | Libbus et al. |
| 8,403,841 B2 | 3/2013 | Miles et al. |
| 8,406,886 B2 | 3/2013 | Gaunt et al. |
| 8,412,328 B2 | 4/2013 | Whelan et al. |
| 8,412,335 B2 | 4/2013 | Gliner et al. |
| 8,417,345 B2 | 4/2013 | Machado et al. |
| 8,419,653 B2 | 4/2013 | Bleich et al. |
| 8,428,732 B2 | 4/2013 | Nishida et al. |
| 8,428,738 B2 | 4/2013 | Valencia |
| 8,428,739 B2 | 4/2013 | Ahuja et al. |
| 8,430,882 B2 | 4/2013 | Lowry et al. |
| 8,444,640 B2 | 5/2013 | Demarais et al. |
| 8,457,764 B2 | 6/2013 | Ramachandran et al. |
| 8,460,167 B2 | 6/2013 | Chornenky et al. |
| 8,463,383 B2 | 6/2013 | Sakai et al. |
| 8,473,048 B2 | 6/2013 | Greenberg et al. |
| 8,494,640 B2 | 7/2013 | Peterson et al. |
| 8,494,642 B2 | 7/2013 | Cowan et al. |
| 8,498,717 B2 | 7/2013 | Lee et al. |
| 8,498,720 B2 | 7/2013 | Pellinen et al. |
| 8,506,613 B2 | 8/2013 | Webb et al. |
| 8,509,903 B2 | 8/2013 | York et al. |
| 8,512,235 B2 | 8/2013 | Miles et al. |
| 8,515,533 B2 | 8/2013 | Rofougaran |
| 8,515,543 B2 | 8/2013 | Greenberg et al. |
| 8,517,961 B2 | 8/2013 | Imran et al. |
| 8,524,311 B1 | 9/2013 | Greenberg et al. |
| 8,532,776 B2 | 9/2013 | Greenberg et al. |
| 8,538,537 B2 | 9/2013 | Hulvershorn et al. |
| 8,543,210 B2 | 9/2013 | Sharma |
| 8,548,600 B2 | 10/2013 | Deem et al. |
| 8,554,328 B2 | 10/2013 | Faraji et al. |
| 8,554,337 B2 | 10/2013 | Barolat |
| 8,556,838 B2 | 10/2013 | Moutray |
| 8,560,041 B2 | 10/2013 | Flaherty et al. |
| 8,562,521 B2 | 10/2013 | Miles et al. |
| 8,565,894 B2 | 10/2013 | Vetter et al. |
| 8,568,331 B2 | 10/2013 | Bertagnoli et al. |
| 8,571,665 B2 | 10/2013 | Moffitt et al. |
| 8,579,837 B1 | 11/2013 | Makower et al. |
| 8,583,238 B1 | 11/2013 | Heldman et al. |
| 8,588,918 B2 | 11/2013 | Bighetti |
| 8,594,798 B2 | 11/2013 | Osorio et al. |
| 8,600,514 B1 | 12/2013 | Carroll |
| 8,608,664 B2 | 12/2013 | Kunitake et al. |
| 8,612,002 B2 | 12/2013 | Faltys et al. |
| 8,615,308 B2 | 12/2013 | Hung et al. |
| 8,617,808 B2 | 12/2013 | Braesch-Andersen et al. |
| 8,626,265 B2 | 1/2014 | Hempel et al. |
| 8,626,305 B2 | 1/2014 | Nielsen et al. |
| 8,628,469 B2 | 1/2014 | Miles et al. |
| 8,634,930 B2 | 1/2014 | Dalal et al. |
| 8,634,932 B1 | 1/2014 | Ye et al. |
| 8,639,344 B2 | 1/2014 | Greenberg et al. |
| 8,644,900 B2 | 2/2014 | Balberg et al. |
| 8,644,937 B2 | 2/2014 | Greenberg et al. |
| 8,644,938 B2 | 2/2014 | Craggs |
| 8,647,346 B2 | 2/2014 | Bleich et al. |
| 8,649,845 B2 | 2/2014 | McIntyre et al. |
| 8,649,868 B2 | 2/2014 | Greenberg et al. |
| 8,652,129 B2 | 2/2014 | Wu et al. |
| 8,652,187 B2 | 2/2014 | Wells et al. |
| 8,655,455 B2 | 2/2014 | Mann et al. |
| 8,660,655 B2 | 2/2014 | Peterson et al. |
| 8,666,500 B2 | 3/2014 | Greenberg et al. |
| 8,667,971 B2 | 3/2014 | Makkar et al. |
| 8,667,972 B2 | 3/2014 | Makkar et al. |
| 8,669,058 B2 | 3/2014 | Liew |
| 8,670,837 B2 | 3/2014 | Daneshvar et al. |
| 8,674,838 B2 | 3/2014 | Konishi et al. |
| 8,676,274 B2 | 3/2014 | Li |
| 8,682,443 B2 | 3/2014 | Faraji et al. |
| 8,698,637 B2 | 4/2014 | Raichman |
| 8,702,685 B2 | 4/2014 | Schwartz et al. |
| 8,706,241 B2 | 4/2014 | Firlik et al. |
| 8,708,899 B2 | 4/2014 | Miles et al. |
| 8,712,517 B2 | 4/2014 | Jolly |
| 8,712,538 B2 | 4/2014 | Greenberg et al. |
| 8,712,549 B2 | 4/2014 | Zdeblick et al. |
| 8,721,637 B2 | 5/2014 | Zarins et al. |
| 8,725,251 B2 | 5/2014 | Della Rocca et al. |
| 8,734,339 B2 | 5/2014 | Rao et al. |
| 8,740,783 B2 | 6/2014 | Gharib et al. |
| 8,740,896 B2 | 6/2014 | Zarins et al. |
| 8,744,570 B2 | 6/2014 | Lee et al. |

(56) References Cited

U.S. PATENT DOCUMENTS

| | | |
|---|---|---|
| 8,750,957 B2 | 6/2014 | Tang et al. |
| 8,753,271 B1 | 6/2014 | Miles et al. |
| 8,755,896 B2 | 6/2014 | Humayun et al. |
| 8,761,889 B2 | 6/2014 | Wingeier et al. |
| 8,774,922 B2 | 7/2014 | Zarins et al. |
| 8,774,937 B2 | 7/2014 | Mercanzini et al. |
| 8,777,942 B2 | 7/2014 | Wu et al. |
| 8,781,603 B2 | 7/2014 | Ye et al. |
| 8,784,461 B2 | 7/2014 | Webb et al. |
| 8,788,064 B2 | 7/2014 | Mercanzini et al. |
| 8,788,065 B2 | 7/2014 | Rezai et al. |
| 8,790,338 B2 | 7/2014 | Asirvatham et al. |
| 8,798,756 B2 | 8/2014 | McClure et al. |
| 8,801,589 B2 | 8/2014 | Peterchev et al. |
| 8,805,467 B2 | 8/2014 | Yobas et al. |
| 8,805,517 B2 | 8/2014 | Radivojevic et al. |
| 8,805,521 B2 | 8/2014 | Carroll |
| 8,821,396 B1 | 9/2014 | Miles et al. |
| 8,831,750 B2 | 9/2014 | Ramachandran et al. |
| 8,834,545 B2 | 9/2014 | Stafford et al. |
| 8,835,163 B2 | 9/2014 | Zhao et al. |
| 8,843,201 B1 | 9/2014 | Heldman et al. |
| 8,843,204 B2 | 9/2014 | Garnham et al. |
| 8,843,210 B2 | 9/2014 | Simon et al. |
| 8,849,412 B2 | 9/2014 | Perryman et al. |
| 8,855,767 B2 | 10/2014 | Faltys et al. |
| 8,862,236 B2 | 10/2014 | Wolpaw et al. |
| 8,864,665 B2 | 10/2014 | Rotondo et al. |
| 8,864,759 B2 | 10/2014 | Godara et al. |
| 8,866,621 B2 | 10/2014 | Wolfe et al. |
| 8,868,164 B2 | 10/2014 | Kabakov et al. |
| 8,868,172 B2 | 10/2014 | Leyde et al. |
| 8,868,216 B2 | 10/2014 | Dunagan |
| 8,870,857 B2 | 10/2014 | Seymour et al. |
| 8,874,216 B2 | 10/2014 | Kim et al. |
| 8,874,239 B2 | 10/2014 | Greenberg et al. |
| 8,880,189 B2 | 11/2014 | Lipani |
| 8,886,324 B2 | 11/2014 | Beuter et al. |
| 8,888,773 B2 | 11/2014 | Chang et al. |
| 8,892,215 B2 | 11/2014 | Lipani |
| 8,903,494 B2 | 12/2014 | Goldwasser et al. |
| 8,903,501 B2 | 12/2014 | Perryman |
| 8,909,343 B2 | 12/2014 | Towe |
| 8,909,344 B2 | 12/2014 | Arle et al. |
| 8,909,345 B1 | 12/2014 | Danilov et al. |
| 8,912,149 B1 | 12/2014 | Rawat et al. |
| 8,915,846 B2 | 12/2014 | Miles et al. |
| 8,915,867 B2 | 12/2014 | Imran et al. |
| 8,918,178 B2 | 12/2014 | Simon et al. |
| 8,921,473 B1 | 12/2014 | Hyman |
| 8,926,959 B2 | 1/2015 | Deisseroth et al. |
| 8,929,990 B2 | 1/2015 | Moffitt et al. |
| 8,932,196 B2 | 1/2015 | Chornenky et al. |
| 8,942,797 B2 | 1/2015 | Bartol et al. |
| 8,942,812 B2 | 1/2015 | Machado et al. |
| 8,942,821 B2 | 1/2015 | Barolat |
| 8,945,004 B2 | 2/2015 | Miles et al. |
| 8,945,216 B2 | 2/2015 | Parker et al. |
| 8,948,884 B2 | 2/2015 | Ramachandran et al. |
| 8,951,193 B2 | 2/2015 | Ong et al. |
| 8,954,144 B2 | 2/2015 | Anderson et al. |
| 8,954,150 B2 | 2/2015 | Swanson et al. |
| 8,954,157 B2 | 2/2015 | Faraji et al. |
| 8,954,167 B2 | 2/2015 | Zarembo et al. |
| 8,956,387 B2 | 2/2015 | Naghavi et al. |
| 8,958,862 B2 | 2/2015 | Hetke et al. |
| 8,958,883 B2 | 2/2015 | Mueller et al. |
| 8,958,890 B2 | 2/2015 | Kipke et al. |
| 8,965,513 B2 | 2/2015 | Wingeier et al. |
| 8,969,532 B2 | 3/2015 | DeFrees et al. |
| 8,972,026 B2 | 3/2015 | Kipke et al. |
| 8,974,402 B2 | 3/2015 | Oddsson et al. |
| 8,983,593 B2 | 3/2015 | Bartol et al. |
| 8,983,601 B2 | 3/2015 | Fukamachi et al. |
| 8,983,628 B2 | 3/2015 | Simon et al. |
| 8,983,629 B2 | 3/2015 | Simon et al. |
| 8,985,057 B2 | 3/2015 | Woodward |
| 8,986,294 B2 | 3/2015 | Demarais et al. |
| 8,992,522 B2 | 3/2015 | Pellegrino et al. |
| 8,996,131 B1 | 3/2015 | Owen et al. |
| 8,998,894 B2 | 4/2015 | Mauch et al. |
| 9,002,458 B2 | 4/2015 | Pal et al. |
| 9,002,477 B2 | 4/2015 | Burnett |
| 9,005,191 B2 | 4/2015 | Azamian et al. |
| 9,008,784 B2 | 4/2015 | Chan et al. |
| 9,014,810 B2 | 4/2015 | Sauter-Starace et al. |
| 9,014,811 B2 | 4/2015 | Pal et al. |
| 9,014,823 B2 | 4/2015 | Simon et al. |
| 9,019,106 B2 | 4/2015 | Alameh et al. |
| 9,020,598 B2 | 4/2015 | Simon et al. |
| 9,020,612 B1 | 4/2015 | Danilov et al. |
| 9,023,037 B2 | 5/2015 | Zarins et al. |
| 9,034,640 B2 | 5/2015 | Matos et al. |
| 9,037,268 B2 | 5/2015 | Knight |
| 9,042,958 B2 | 5/2015 | Karmarkar et al. |
| 9,043,001 B2 | 5/2015 | Simon et al. |
| 9,044,596 B2 | 6/2015 | Mahadevan-Jansen et al. |
| 9,044,611 B2 | 6/2015 | Zhao et al. |
| 9,056,197 B2 | 6/2015 | Kishawi et al. |
| 9,061,097 B2 | 6/2015 | Holt et al. |
| 9,061,134 B2 | 6/2015 | Askin, III et al. |
| 9,061,135 B1 | 6/2015 | Keller et al. |
| 9,072,886 B2 | 7/2015 | Gaunt et al. |
| 9,072,889 B1 | 7/2015 | Guarraia et al. |
| 9,072,891 B1 | 7/2015 | Rao |
| 9,084,550 B1 | 7/2015 | Bartol et al. |
| 9,084,610 B2 | 7/2015 | Goshgarian et al. |
| 9,084,895 B2 | 7/2015 | Greenberg et al. |
| 9,084,900 B2 | 7/2015 | Hershey et al. |
| 9,089,341 B2 | 7/2015 | Chomas et al. |
| 9,089,687 B2 | 7/2015 | Lee et al. |
| 9,089,691 B2 | 7/2015 | Libbus et al. |
| 9,095,267 B2 | 8/2015 | Halpern et al. |
| 9,095,320 B2 | 8/2015 | Littrup et al. |
| 9,095,538 B2 | 8/2015 | Yu et al. |
| 9,101,279 B2 | 8/2015 | Ritchey et al. |
| 9,113,912 B1 | 8/2015 | Mehta et al. |
| 9,114,261 B2 | 8/2015 | Yonce |
| 9,119,628 B1 | 9/2015 | Mehta et al. |
| 9,119,964 B2 | 9/2015 | Marnfeldt |
| 9,126,197 B2 | 9/2015 | Orwar et al. |
| 9,132,058 B2 | 9/2015 | Imboden et al. |
| 9,138,579 B2 | 9/2015 | Wolpaw et al. |
| 9,144,677 B2 | 9/2015 | Garnham et al. |
| 9,155,887 B2 | 10/2015 | Miller, III et al. |
| 9,158,890 B2 | 10/2015 | Meredith et al. |
| 9,162,010 B2 | 10/2015 | Lenarz et al. |
| 9,162,064 B2 | 10/2015 | Faltys et al. |
| 9,173,585 B2 | 11/2015 | Tsampazis et al. |
| 9,179,850 B2 | 11/2015 | Wingeier et al. |
| 9,179,875 B2 | 11/2015 | Hua |
| 9,189,613 B1 | 11/2015 | Tuthill et al. |
| 9,192,757 B2 | 11/2015 | Seymour |
| 9,192,767 B2 | 11/2015 | Mercanzini et al. |
| 9,199,089 B2 | 12/2015 | Perryman et al. |
| 9,205,275 B2 | 12/2015 | Pan et al. |
| 9,220,897 B2 | 12/2015 | Perryman et al. |
| 9,220,899 B2 | 12/2015 | Cattaneo et al. |
| 9,220,900 B2 | 12/2015 | Libbus et al. |
| 9,221,177 B2 | 12/2015 | Herr et al. |
| 9,227,051 B1 | 1/2016 | Fisk et al. |
| 9,227,056 B1 | 1/2016 | Heldman et al. |
| 9,254,382 B2 | 2/2016 | Ahmad et al. |
| 9,855,427 B2 | 1/2018 | Bennett et al. |
| 9,895,546 B2 | 2/2018 | Jiang et al. |
| 10,118,040 B2 | 11/2018 | Zhu |
| 10,342,977 B2 | 7/2019 | Raghunathan |
| 10,412,828 B1 | 9/2019 | Yamakawa |
| 2001/0034477 A1 | 10/2001 | Mansfield |
| 2001/0055776 A1 | 12/2001 | Greenwalt |
| 2002/0009461 A1 | 1/2002 | Isacson |
| 2002/0019652 A1 | 2/2002 | Silva et al. |
| 2002/0031497 A1 | 3/2002 | Fraser |
| 2002/0034819 A1 | 3/2002 | Smith |

(56) References Cited

U.S. PATENT DOCUMENTS

| | | |
|---|---|---|
| 2002/0055779 A1 | 5/2002 | Andrews |
| 2002/0090722 A1 | 7/2002 | Dominko |
| 2002/0136705 A1 | 9/2002 | Dinsmore |
| 2002/0176849 A1 | 11/2002 | Slepian |
| 2003/0002297 A1 | 1/2003 | Nemtsev |
| 2003/0004547 A1 | 1/2003 | Owen |
| 2003/0049328 A1 | 3/2003 | Dalal |
| 2003/0088274 A1 | 5/2003 | Gliner |
| 2003/0097161 A1 | 5/2003 | Firlik |
| 2003/0100367 A1 | 5/2003 | Cooke |
| 2003/0104993 A1 | 6/2003 | Rueger |
| 2003/0109901 A1 | 6/2003 | Greatbatch |
| 2003/0125786 A1 | 7/2003 | Gliner |
| 2003/0149450 A1 | 8/2003 | Mayberg |
| 2003/0157712 A1 | 8/2003 | Daniel |
| 2003/0195441 A1 | 10/2003 | Firouzgar |
| 2003/0198664 A1 | 10/2003 | Sullivan |
| 2003/0232055 A1 | 12/2003 | Medzhitov |
| 2004/0005291 A1 | 1/2004 | Rogers |
| 2004/0014662 A1 | 1/2004 | Lindquist |
| 2004/0028613 A1 | 2/2004 | Quay |
| 2004/0030365 A1 | 2/2004 | Rubin |
| 2004/0038888 A1 | 2/2004 | Mercer et al. |
| 2004/0048279 A1 | 3/2004 | Olek et al. |
| 2004/0048373 A1 | 3/2004 | Gage et al. |
| 2004/0049134 A1 | 3/2004 | Tosaya |
| 2004/0054300 A1 | 3/2004 | Hung et al. |
| 2004/0062755 A1 | 4/2004 | Smith et al. |
| 2004/0064052 A1 | 4/2004 | Chance |
| 2004/0081652 A1 | 4/2004 | Zack |
| 2004/0093093 A1 | 5/2004 | Andrews |
| 2004/0097401 A1 | 5/2004 | Datta |
| 2004/0097839 A1 | 5/2004 | Epley |
| 2004/0102525 A1 | 5/2004 | Kozachuk |
| 2004/0106966 A1 | 6/2004 | Scribner |
| 2004/0121464 A1 | 6/2004 | Rathjen |
| 2004/0143170 A1 | 7/2004 | DuRousseau |
| 2004/0147975 A1 | 7/2004 | Popovic |
| 2004/0156826 A1 | 8/2004 | Dangond |
| 2004/0162583 A1 | 8/2004 | Bingham |
| 2004/0172100 A1 | 9/2004 | Humayun |
| 2004/0172102 A1 | 9/2004 | Leysieffer |
| 2004/0185557 A1 | 9/2004 | Smith et al. |
| 2004/0199235 A1 | 10/2004 | Younis |
| 2004/0212504 A1 | 10/2004 | Forcier et al. |
| 2004/0219184 A1 | 11/2004 | Brown et al. |
| 2004/0228831 A1 | 11/2004 | Belinka, Jr. |
| 2004/0229702 A1 | 11/2004 | Cooke |
| 2004/0230226 A1 | 11/2004 | Bingham |
| 2004/0243021 A1 | 12/2004 | Murphy |
| 2005/0003998 A1 | 1/2005 | Bertilsson |
| 2005/0015133 A1 | 1/2005 | Ibrahim |
| 2005/0020519 A1 | 1/2005 | Albiston |
| 2005/0020945 A1 | 1/2005 | Tosaya |
| 2005/0038473 A1 | 2/2005 | Tamarkin |
| 2005/0054096 A1 | 3/2005 | Piniella |
| 2005/0054907 A1 | 3/2005 | Page et al. |
| 2005/0070819 A1 | 3/2005 | Poux |
| 2005/0073649 A1 | 4/2005 | Spector |
| 2005/0107859 A1 | 5/2005 | Daglow et al. |
| 2005/0125044 A1 | 6/2005 | Tracey |
| 2005/0165323 A1 | 7/2005 | Montgomery |
| 2005/0203366 A1 | 9/2005 | Donoghue |
| 2005/0203601 A1 | 9/2005 | Palanker |
| 2005/0222631 A1 | 10/2005 | Dalal et al. |
| 2005/0226852 A1 | 10/2005 | Toda |
| 2005/0234370 A1 | 10/2005 | Beal |
| 2005/0267552 A1 | 12/2005 | Conquergood |
| 2005/0272097 A1 | 12/2005 | Calenoff |
| 2005/0273890 A1 | 12/2005 | Flaherty |
| 2005/0277918 A1 | 12/2005 | Shah |
| 2006/0034767 A1 | 2/2006 | Lum |
| 2006/0047326 A1 | 3/2006 | Wheeler |
| 2006/0049950 A1 | 3/2006 | Lockhart |
| 2006/0049957 A1 | 3/2006 | Surgenor |
| 2006/0058627 A1 | 3/2006 | Flaherty |
| 2006/0118035 A1 | 6/2006 | Lasater |
| 2006/0122458 A1 | 6/2006 | Bleich |
| 2006/0122529 A1 | 6/2006 | Tsau |
| 2006/0122864 A1 | 6/2006 | Gottesman |
| 2006/0140930 A1 | 6/2006 | Rodriguez |
| 2006/0149345 A1 | 7/2006 | Boggs, II |
| 2006/0161225 A1 | 7/2006 | Sormann |
| 2006/0167498 A1 | 7/2006 | DiLorenzo |
| 2006/0167564 A1 | 7/2006 | Flaherty |
| 2006/0171933 A1 | 8/2006 | Short |
| 2006/0184219 A1 | 8/2006 | Pajunk |
| 2006/0190056 A1 | 8/2006 | Fowler |
| 2006/0195146 A1 | 8/2006 | Tracey et al. |
| 2006/0195153 A1 | 8/2006 | Diubaldi et al. |
| 2006/0206167 A1 | 9/2006 | Flaherty |
| 2006/0206178 A1 | 9/2006 | Kim |
| 2006/0234376 A1 | 10/2006 | Mistry |
| 2006/0263336 A1 | 11/2006 | Caplan |
| 2006/0265037 A1 | 11/2006 | Kuzma |
| 2006/0281130 A1 | 12/2006 | Bock |
| 2007/0005106 A1 | 1/2007 | Adducci |
| 2007/0021803 A1 | 1/2007 | Deem |
| 2007/0043591 A1 | 2/2007 | Meretei |
| 2007/0049814 A1 | 3/2007 | Muccio |
| 2007/0049842 A1 | 3/2007 | Hill |
| 2007/0067004 A1 | 3/2007 | Boveja |
| 2007/0073361 A1 | 3/2007 | Goren |
| 2007/0088335 A1 | 4/2007 | Jolly |
| 2007/0100393 A1 | 5/2007 | Whitehurst |
| 2007/0102009 A1 | 5/2007 | Wong |
| 2007/0107071 A1 | 5/2007 | Couillard-Despres |
| 2007/0123778 A1 | 5/2007 | Kantorovich |
| 2007/0129769 A1 | 6/2007 | Bourget |
| 2007/0134657 A1 | 6/2007 | Poznansky |
| 2007/0135846 A1 | 6/2007 | Knudson |
| 2007/0165322 A1 | 7/2007 | Strom |
| 2007/0173893 A1 | 7/2007 | Pitts |
| 2007/0173903 A1 | 7/2007 | Goren |
| 2007/0179558 A1 | 8/2007 | Gliner |
| 2007/0180542 A1 | 8/2007 | Brinster |
| 2007/0192881 A1 | 8/2007 | Brinster |
| 2007/0203533 A1 | 8/2007 | Goren |
| 2007/0208212 A1 | 9/2007 | DiLorenzo |
| 2007/0208385 A1 | 9/2007 | Carroll |
| 2007/0219074 A1 | 9/2007 | Pride |
| 2007/0239211 A1 | 10/2007 | Lorincz |
| 2007/0249952 A1 | 10/2007 | Rubin |
| 2007/0276449 A1 | 11/2007 | Gunter |
| 2007/0282396 A1 | 12/2007 | Overstreet |
| 2007/0287613 A1 | 12/2007 | Adducci |
| 2007/0293893 A1 | 12/2007 | Stolen |
| 2007/0299483 A1 | 12/2007 | Strother |
| 2008/0002276 A1 | 1/2008 | Strom |
| 2008/0033520 A1 | 2/2008 | Jolly |
| 2008/0040951 A1 | 2/2008 | Kates |
| 2008/0057028 A1 | 3/2008 | Alitalo et al. |
| 2008/0064946 A1 | 3/2008 | Greenberg |
| 2008/0071321 A1 | 3/2008 | Boggs, II |
| 2008/0074794 A1 | 3/2008 | Lee |
| 2008/0077192 A1 | 3/2008 | Harry et al. |
| 2008/0095747 A1 | 4/2008 | Rutishauser |
| 2008/0097530 A1 | 4/2008 | Muccio |
| 2008/0120029 A1 | 5/2008 | Zelek et al. |
| 2008/0125870 A1 | 5/2008 | Carmichael |
| 2008/0133016 A1 | 6/2008 | Heinz |
| 2008/0139907 A1 | 6/2008 | Rao |
| 2008/0154335 A1 | 6/2008 | Thrope |
| 2008/0161879 A1 | 7/2008 | Firlik |
| 2008/0161882 A1 | 7/2008 | Firlik |
| 2008/0161887 A1 | 7/2008 | Hagen |
| 2008/0170234 A1 | 7/2008 | Kim |
| 2008/0170316 A1 | 7/2008 | Kim |
| 2008/0195163 A1 | 8/2008 | Scharmer |
| 2008/0200967 A1 | 8/2008 | Ponomarev |
| 2008/0208280 A1 | 8/2008 | Lindenthaler et al. |
| 2008/0215112 A1 | 9/2008 | Firlik |
| 2008/0221653 A1 | 9/2008 | Agrawal |
| 2008/0241208 A1 | 10/2008 | Shanley |

(56) References Cited

U.S. PATENT DOCUMENTS

| | | |
|---|---|---|
| 2008/0242607 A1 | 10/2008 | DeFrees |
| 2008/0243218 A1 | 10/2008 | Bottomley |
| 2008/0248959 A1 | 10/2008 | DeFrees |
| 2008/0249439 A1 | 10/2008 | Tracey |
| 2008/0253992 A1 | 10/2008 | DeFrees |
| 2008/0255582 A1 | 10/2008 | Harris |
| 2008/0262557 A1 | 10/2008 | Brown |
| 2008/0262584 A1 | 10/2008 | Bottomley |
| 2008/0274958 A1 | 11/2008 | DeFrees |
| 2008/0275546 A1 | 11/2008 | Storey |
| 2008/0280818 A1 | 11/2008 | DeFrees |
| 2008/0312538 A1 | 12/2008 | Shahar et al. |
| 2008/0318314 A1 | 12/2008 | Fulga et al. |
| 2009/0012586 A1 | 1/2009 | Kepecs |
| 2009/0012590 A1 | 1/2009 | Inman |
| 2009/0029912 A1 | 1/2009 | Gronthos |
| 2009/0036938 A1 | 2/2009 | Shipley |
| 2009/0036945 A1* | 2/2009 | Chancellor ........ A61N 1/36007 607/39 |
| 2009/0054800 A1 | 2/2009 | Martinerie |
| 2009/0054950 A1 | 2/2009 | Stephens |
| 2009/0076421 A1 | 3/2009 | Grant, Jr. |
| 2009/0076444 A1 | 3/2009 | Machado |
| 2009/0086015 A1 | 4/2009 | Larsen |
| 2009/0105149 A1 | 4/2009 | Albrechtsen |
| 2009/0112278 A1 | 4/2009 | Wingeier |
| 2009/0112279 A1 | 4/2009 | Wingeier |
| 2009/0118777 A1 | 5/2009 | Iki et al. |
| 2009/0118788 A1 | 5/2009 | Firlik |
| 2009/0124965 A1 | 5/2009 | Greenberg |
| 2009/0131995 A1 | 5/2009 | Sloan et al. |
| 2009/0132018 A1 | 5/2009 | DiUbaldi et al. |
| 2009/0149782 A1 | 6/2009 | Cohen |
| 2009/0149900 A1 | 6/2009 | Moffitt et al. |
| 2009/0157091 A1 | 6/2009 | Buysman |
| 2009/0171381 A1 | 7/2009 | Schmitz |
| 2009/0182393 A1 | 7/2009 | Bachinski |
| 2009/0201671 A1 | 8/2009 | Huntley |
| 2009/0214474 A1 | 8/2009 | Jennings |
| 2009/0215896 A1 | 8/2009 | Morseman |
| 2009/0220466 A1 | 9/2009 | Ratajczak |
| 2009/0226598 A1 | 9/2009 | Feng |
| 2009/0227025 A1 | 9/2009 | Nichols |
| 2009/0227831 A1 | 9/2009 | Burnett et al. |
| 2009/0227965 A1 | 9/2009 | Wijesiriwardana |
| 2009/0234265 A1 | 9/2009 | Reid, Jr. |
| 2009/0258048 A1 | 10/2009 | Ward |
| 2009/0270958 A1 | 10/2009 | Greenberg |
| 2009/0292338 A1 | 11/2009 | Gordon |
| 2009/0299439 A1 | 12/2009 | Mire et al. |
| 2009/0306728 A1 | 12/2009 | Wright |
| 2009/0306745 A1 | 12/2009 | Parker |
| 2009/0326612 A1 | 12/2009 | Distler |
| 2010/0004654 A1 | 1/2010 | Schmitz |
| 2010/0010550 A1 | 1/2010 | Ponomarev |
| 2010/0016732 A1 | 1/2010 | Wells |
| 2010/0035299 A1 | 2/2010 | DeFrees |
| 2010/0037755 A1 | 2/2010 | McMillen |
| 2010/0042180 A1 | 2/2010 | Mueller et al. |
| 2010/0042185 A1 | 2/2010 | Curtis |
| 2010/0045595 A1 | 2/2010 | Bakke |
| 2010/0047915 A1 | 2/2010 | Soykan |
| 2010/0092983 A1 | 4/2010 | Liew |
| 2010/0092984 A1 | 4/2010 | Liew |
| 2010/0094311 A1 | 4/2010 | Jolly et al. |
| 2010/0099786 A1 | 4/2010 | Dias |
| 2010/0112026 A1 | 5/2010 | Karp |
| 2010/0114195 A1 | 5/2010 | Burnes |
| 2010/0124745 A1 | 5/2010 | Liew |
| 2010/0124746 A1 | 5/2010 | Liew |
| 2010/0145427 A1 | 6/2010 | Gliner |
| 2010/0168739 A1 | 7/2010 | Wu |
| 2010/0179284 A1 | 7/2010 | Ward |
| 2010/0185042 A1 | 7/2010 | Schneider |
| 2010/0189712 A1 | 7/2010 | L'Heureux |
| 2010/0203520 A1 | 8/2010 | Liew |
| 2010/0204538 A1 | 8/2010 | Burnett et al. |
| 2010/0204777 A1 | 8/2010 | Storey |
| 2010/0211172 A1 | 8/2010 | Bellamkonda |
| 2010/0222630 A1 | 9/2010 | Mangrum |
| 2010/0222844 A1 | 9/2010 | Troosters |
| 2010/0241195 A1 | 9/2010 | Meadows |
| 2010/0268055 A1 | 10/2010 | Jung et al. |
| 2010/0268125 A9 | 10/2010 | Epley |
| 2010/0280570 A1 | 11/2010 | Sturm |
| 2010/0280571 A1 | 11/2010 | Sloan |
| 2010/0286067 A1 | 11/2010 | DeFrees |
| 2010/0292759 A1 | 11/2010 | Hahn |
| 2010/0298916 A1 | 11/2010 | Rabischong |
| 2010/0304864 A1 | 12/2010 | Johnson |
| 2010/0305674 A1 | 12/2010 | Zarembo |
| 2010/0310529 A1 | 12/2010 | Aizman |
| 2010/0324355 A1 | 12/2010 | Spitaels |
| 2010/0324626 A1 | 12/2010 | Lefkovitz |
| 2011/0009959 A1 | 1/2011 | Tiedtke |
| 2011/0014189 A1 | 1/2011 | Soula et al. |
| 2011/0022105 A9 | 1/2011 | Owen |
| 2011/0022131 A1 | 1/2011 | Giuliano |
| 2011/0028345 A1 | 2/2011 | Fang et al. |
| 2011/0040204 A1 | 2/2011 | Ivorra et al. |
| 2011/0040349 A1 | 2/2011 | Graupe |
| 2011/0059447 A1 | 3/2011 | Liew |
| 2011/0060266 A1 | 3/2011 | Streeter |
| 2011/0082531 A1 | 4/2011 | Swanson |
| 2011/0092863 A1 | 4/2011 | Kim |
| 2011/0098777 A1 | 4/2011 | Silverstone |
| 2011/0106207 A1 | 5/2011 | Cauller |
| 2011/0106219 A1 | 5/2011 | Cauller |
| 2011/0112352 A1 | 5/2011 | Pilla et al. |
| 2011/0118556 A1 | 5/2011 | Siegel |
| 2011/0124959 A1 | 5/2011 | Murison |
| 2011/0137189 A1 | 6/2011 | Kuo |
| 2011/0158444 A1 | 6/2011 | Waldmann |
| 2011/0177029 A1 | 7/2011 | DeFrees |
| 2011/0184269 A1 | 7/2011 | Sauter-Starace |
| 2011/0190882 A1 | 8/2011 | Parker |
| 2011/0195106 A1 | 8/2011 | McMurtrey |
| 2011/0196454 A1 | 8/2011 | Strand |
| 2011/0202120 A1 | 8/2011 | Ball et al. |
| 2011/0208226 A1 | 8/2011 | Fatone et al. |
| 2011/0218593 A1 | 9/2011 | Rubinstein et al. |
| 2011/0224565 A1 | 9/2011 | Ong |
| 2011/0224754 A1 | 9/2011 | Wei |
| 2011/0257501 A1 | 10/2011 | Huys et al. |
| 2011/0257504 A1 | 10/2011 | Hendricks |
| 2011/0262501 A1 | 10/2011 | Webster |
| 2011/0264178 A1 | 10/2011 | Mehregany |
| 2011/0268776 A1 | 11/2011 | Schapira |
| 2011/0270345 A1 | 11/2011 | Johnston |
| 2011/0270361 A1 | 11/2011 | Borsody |
| 2011/0295156 A1 | 12/2011 | Arturi |
| 2011/0301662 A1* | 12/2011 | Bar-Yoseph ......... A61N 1/0514 607/40 |
| 2011/0313270 A1 | 12/2011 | Pereira Neves |
| 2011/0319703 A1 | 12/2011 | Wiskerke |
| 2012/0016431 A1 | 1/2012 | Paul |
| 2012/0016440 A1 | 1/2012 | Muccio |
| 2012/0022616 A1 | 1/2012 | Garnham |
| 2012/0035684 A1 | 2/2012 | Thompson |
| 2012/0045487 A1 | 2/2012 | Lahann |
| 2012/0046702 A1 | 2/2012 | Gibson |
| 2012/0059389 A1 | 3/2012 | Larson |
| 2012/0064628 A1 | 3/2012 | Blick |
| 2012/0076830 A1 | 3/2012 | Sitharaman |
| 2012/0078327 A1 | 3/2012 | Sloan et al. |
| 2012/0089047 A1 | 4/2012 | Ryba et al. |
| 2012/0095166 A1 | 4/2012 | Ward |
| 2012/0095524 A1 | 4/2012 | Nelson |
| 2012/0101326 A1* | 4/2012 | Simon ................ A61N 1/36034 600/9 |
| 2012/0101413 A1 | 4/2012 | Beetel |
| 2012/0109233 A1 | 5/2012 | Lee et al. |
| 2012/0123508 A1 | 5/2012 | Wentz |
| 2012/0124470 A1 | 5/2012 | West |

(56) References Cited

U.S. PATENT DOCUMENTS

| | | |
|---|---|---|
| 2012/0130360 A1 | 5/2012 | Buckley |
| 2012/0134965 A1 | 5/2012 | Kim et al. |
| 2012/0136232 A1 | 5/2012 | Jeong |
| 2012/0143293 A1 | 6/2012 | Mauch et al. |
| 2012/0158095 A1 | 6/2012 | Jolly |
| 2012/0158104 A1 | 6/2012 | Huynh |
| 2012/0158113 A1 | 6/2012 | Jolly et al. |
| 2012/0158114 A1 | 6/2012 | Debruyne |
| 2012/0179076 A1 | 7/2012 | Bavelier |
| 2012/0185173 A1 | 7/2012 | Yamamoto |
| 2012/0191052 A1 | 7/2012 | Rao |
| 2012/0191086 A1 | 7/2012 | Moll |
| 2012/0197092 A1 | 8/2012 | Luo et al. |
| 2012/0197252 A1 | 8/2012 | Deem |
| 2012/0197374 A1 | 8/2012 | Vogt |
| 2012/0214737 A1 | 8/2012 | Marchionni |
| 2012/0221072 A1 | 8/2012 | Fukamachi |
| 2012/0226331 A1 | 9/2012 | Banna et al. |
| 2012/0237557 A1 | 9/2012 | Lewitus et al. |
| 2012/0238924 A1 | 9/2012 | Avni |
| 2012/0239363 A1 | 9/2012 | Durrani et al. |
| 2012/0244503 A1 | 9/2012 | Neveldine |
| 2012/0245534 A1 | 9/2012 | Jolly |
| 2012/0253236 A1 | 10/2012 | Snow |
| 2012/0259255 A1 | 10/2012 | Tomlinson |
| 2012/0259390 A1 | 10/2012 | Canion |
| 2012/0277825 A1 | 11/2012 | Mawson |
| 2012/0277842 A1 | 11/2012 | Kunis |
| 2012/0282228 A1 | 11/2012 | Bhasin |
| 2012/0283800 A1 | 11/2012 | Perryman |
| 2012/0296191 A1 | 11/2012 | McGrath |
| 2012/0296230 A1 | 11/2012 | Davis |
| 2012/0296444 A1 | 11/2012 | Greenberg |
| 2012/0302856 A1 | 11/2012 | Chang |
| 2012/0310140 A1 | 12/2012 | Kramer |
| 2012/0323288 A1 | 12/2012 | Anderson |
| 2013/0006322 A1 | 1/2013 | Tai |
| 2013/0012831 A1 | 1/2013 | Schmitz |
| 2013/0018240 A1 | 1/2013 | McCoy |
| 2013/0018444 A1 | 1/2013 | Glenn |
| 2013/0035745 A1 | 2/2013 | Ahmed |
| 2013/0041432 A1 | 2/2013 | Tucker et al. |
| 2013/0052712 A1 | 2/2013 | Cha |
| 2013/0053853 A1 | 2/2013 | Schmitz |
| 2013/0053934 A1 | 2/2013 | Gluckman |
| 2013/0066147 A1 | 3/2013 | Brown |
| 2013/0066216 A1 | 3/2013 | Park |
| 2013/0066391 A1 | 3/2013 | Hulvershorn |
| 2013/0066392 A1 | 3/2013 | Simon |
| 2013/0066395 A1 | 3/2013 | Simon |
| 2013/0072808 A1 | 3/2013 | Neves |
| 2013/0072835 A1 | 3/2013 | Harry et al. |
| 2013/0090542 A1 | 4/2013 | Kipke et al. |
| 2013/0090711 A1 | 4/2013 | Ramachandran |
| 2013/0101635 A1 | 4/2013 | Park et al. |
| 2013/0116685 A1 | 5/2013 | Deem et al. |
| 2013/0116744 A1 | 5/2013 | Blum |
| 2013/0122528 A1 | 5/2013 | Tyrell |
| 2013/0123568 A1 | 5/2013 | Hamilton |
| 2013/0123570 A1 | 5/2013 | Ly et al. |
| 2013/0131743 A1 | 5/2013 | Yamasaki |
| 2013/0131753 A1 | 5/2013 | Simon |
| 2013/0137955 A1 | 5/2013 | Kong et al. |
| 2013/0144143 A1 | 6/2013 | Kim et al. |
| 2013/0144369 A1 | 6/2013 | Elias |
| 2013/0144370 A1 | 6/2013 | Debruyne |
| 2013/0150653 A1 | 6/2013 | Borsody |
| 2013/0154838 A1 | 6/2013 | Alameh |
| 2013/0157229 A1 | 6/2013 | Lauritzen |
| 2013/0178765 A1 | 7/2013 | Mishelevich |
| 2013/0184792 A1 | 7/2013 | Simon |
| 2013/0184795 A1 | 7/2013 | Kipke et al. |
| 2013/0184799 A1 | 7/2013 | Kipke et al. |
| 2013/0204122 A1 | 8/2013 | Hendler et al. |
| 2013/0204317 A1 | 8/2013 | Sauter-Starace |
| 2013/0210041 A1 | 8/2013 | Anderberg |
| 2013/0218456 A1 | 8/2013 | Zelek |
| 2013/0231725 A1 | 9/2013 | Williams |
| 2013/0238066 A1 | 9/2013 | Boggs, II |
| 2013/0238074 A1 | 9/2013 | Zimmerling |
| 2013/0245480 A1 | 9/2013 | Crockford |
| 2013/0245486 A1 | 9/2013 | Simon et al. |
| 2013/0245711 A1 | 9/2013 | Simon |
| 2013/0245712 A1 | 9/2013 | Simon |
| 2013/0245717 A1 | 9/2013 | Stohl et al. |
| 2013/0245765 A1 | 9/2013 | Lowry et al. |
| 2013/0248226 A1 | 9/2013 | Sime |
| 2013/0253299 A1 | 9/2013 | Weber |
| 2013/0274540 A1 | 10/2013 | Pilla |
| 2013/0274658 A1 | 10/2013 | Steinke |
| 2013/0274842 A1 | 10/2013 | Gaunt |
| 2013/0280233 A1 | 10/2013 | Kahn et al. |
| 2013/0282001 A1 | 10/2013 | Hezi-Yamit |
| 2013/0282090 A1 | 10/2013 | Decre |
| 2013/0288233 A1 | 10/2013 | Murray |
| 2013/0289659 A1* | 10/2013 | Nelson ............... A61N 1/36007 607/59 |
| 2013/0289678 A1 | 10/2013 | Clark |
| 2013/0289686 A1 | 10/2013 | Masson |
| 2013/0296767 A1 | 11/2013 | Zarins et al. |
| 2013/0309278 A1 | 11/2013 | Peyman |
| 2013/0310909 A1 | 11/2013 | Simon |
| 2013/0317400 A1 | 11/2013 | Ferezy |
| 2013/0317580 A1 | 11/2013 | Simon |
| 2013/0324994 A1 | 12/2013 | Pellegrino et al. |
| 2013/0331869 A1 | 12/2013 | Runge et al. |
| 2013/0338729 A1 | 12/2013 | Spector |
| 2013/0341185 A1 | 12/2013 | Collaert et al. |
| 2014/0003696 A1 | 1/2014 | Taghva |
| 2014/0018792 A1 | 1/2014 | Gang et al. |
| 2014/0022162 A1 | 1/2014 | Yu et al. |
| 2014/0023999 A1 | 1/2014 | Greder |
| 2014/0024981 A1 | 1/2014 | Chun et al. |
| 2014/0025301 A1 | 1/2014 | Storm, Jr. et al. |
| 2014/0030735 A1 | 1/2014 | Merali et al. |
| 2014/0046423 A1* | 2/2014 | Rajguru ............... A61N 1/0456 607/144 |
| 2014/0051938 A1 | 2/2014 | Goldstein et al. |
| 2014/0058481 A1 | 2/2014 | Perryman et al. |
| 2014/0058483 A1 | 2/2014 | Zao et al. |
| 2014/0066924 A1 | 3/2014 | Azamian et al. |
| 2014/0073883 A1 | 3/2014 | Rao et al. |
| 2014/0074186 A1 | 3/2014 | Faltys et al. |
| 2014/0081682 A1 | 3/2014 | Perlmuter |
| 2014/0094674 A1 | 4/2014 | Nurmikko et al. |
| 2014/0099352 A1 | 4/2014 | Matheny |
| 2014/0107397 A1 | 4/2014 | Simon et al. |
| 2014/0107398 A1 | 4/2014 | Simon et al. |
| 2014/0114168 A1 | 4/2014 | Block et al. |
| 2014/0127171 A1 | 5/2014 | Nocera et al. |
| 2014/0128939 A1 | 5/2014 | Embrey et al. |
| 2014/0135607 A1 | 5/2014 | Lee et al. |
| 2014/0135680 A1 | 5/2014 | Peyman |
| 2014/0142374 A1 | 5/2014 | Makower et al. |
| 2014/0148649 A1 | 5/2014 | Miles et al. |
| 2014/0148871 A1 | 5/2014 | Southwell et al. |
| 2014/0148872 A1 | 5/2014 | Goldwasser et al. |
| 2014/0155811 A1 | 6/2014 | Gibson |
| 2014/0155973 A1 | 6/2014 | Grigsby et al. |
| 2014/0163580 A1 | 6/2014 | Tischendorf et al. |
| 2014/0163641 A1 | 6/2014 | Yao et al. |
| 2014/0163658 A1 | 6/2014 | Faraji et al. |
| 2014/0171807 A1 | 6/2014 | Akkin et al. |
| 2014/0180036 A1 | 6/2014 | Bukkapatnam et al. |
| 2014/0180196 A1 | 6/2014 | Stone et al. |
| 2014/0180365 A1 | 6/2014 | Perryman et al. |
| 2014/0187872 A1 | 7/2014 | Stivoric et al. |
| 2014/0194951 A1 | 7/2014 | Gong et al. |
| 2014/0197937 A1 | 7/2014 | Huang et al. |
| 2014/0200432 A1 | 7/2014 | Banerji et al. |
| 2014/0200466 A1 | 7/2014 | Sereno et al. |
| 2014/0200496 A1 | 7/2014 | Hyde et al. |
| 2014/0200681 A1 | 7/2014 | Kennedy et al. |
| 2014/0206947 A1 | 7/2014 | Isserow et al. |

(56) References Cited

U.S. PATENT DOCUMENTS

| | | |
|---|---|---|
| 2014/0207292 A1 | 7/2014 | Ramagem et al. |
| 2014/0213842 A1 | 7/2014 | Simon et al. |
| 2014/0213971 A1 | 7/2014 | Dolan et al. |
| 2014/0220555 A1 | 8/2014 | Chen et al. |
| 2014/0222125 A1 | 8/2014 | Glenn et al. |
| 2014/0225763 A1 | 8/2014 | Kavaler et al. |
| 2014/0228901 A1 | 8/2014 | Vogt |
| 2014/0228926 A1 | 8/2014 | Della Santina et al. |
| 2014/0235950 A1 | 8/2014 | Miles et al. |
| 2014/0236249 A1 | 8/2014 | Rao et al. |
| 2014/0236847 A1 | 8/2014 | Hamilton |
| 2014/0243616 A1 | 8/2014 | Johnson |
| 2014/0243932 A1 | 8/2014 | Libbus et al. |
| 2014/0249395 A1 | 9/2014 | Zhou et al. |
| 2014/0255461 A9 | 9/2014 | McMurtrey |
| 2014/0257063 A1 | 9/2014 | Ong et al. |
| 2014/0257437 A1 | 9/2014 | Simon et al. |
| 2014/0267123 A1 | 9/2014 | Ludwig |
| 2014/0275737 A1 | 9/2014 | Shore et al. |
| 2014/0276718 A1 | 9/2014 | Turovskiy et al. |
| 2014/0276760 A1 | 9/2014 | Bonyak et al. |
| 2014/0277031 A1 | 9/2014 | Ballakur et al. |
| 2014/0277033 A1 | 9/2014 | Taylor et al. |
| 2014/0277220 A1 | 9/2014 | Brennan et al. |
| 2014/0277237 A1 | 9/2014 | Maskara et al. |
| 2014/0277271 A1 | 9/2014 | Chan et al. |
| 2014/0277310 A1 | 9/2014 | Beetel et al. |
| 2014/0277582 A1 | 9/2014 | Leuthardt et al. |
| 2014/0288379 A1 | 9/2014 | Miles et al. |
| 2014/0296646 A1 | 10/2014 | Wingeier et al. |
| 2014/0300490 A1 | 10/2014 | Kotz et al. |
| 2014/0303525 A1 | 10/2014 | Sitharaman |
| 2014/0303548 A1 | 10/2014 | Jolly et al. |
| 2014/0304773 A1 | 10/2014 | Woods et al. |
| 2014/0309548 A1 | 10/2014 | Merz et al. |
| 2014/0316398 A1 | 10/2014 | Kelly et al. |
| 2014/0320289 A1 | 10/2014 | Raichman |
| 2014/0324120 A1 | 10/2014 | Bogie et al. |
| 2014/0330337 A1 | 11/2014 | Linke et al. |
| 2014/0336631 A1 | 11/2014 | Wu et al. |
| 2014/0336722 A1 | 11/2014 | Rocon De Lima et al. |
| 2014/0350041 A1 | 11/2014 | Yun et al. |
| 2014/0350633 A1 | 11/2014 | Gustafson et al. |
| 2014/0357453 A1 | 12/2014 | Tamanaha |
| 2014/0357933 A1 | 12/2014 | Lee et al. |
| 2014/0360511 A1 | 12/2014 | Mohler |
| 2014/0371547 A1 | 12/2014 | Gartenberg et al. |
| 2014/0371564 A1 | 12/2014 | Anikeeva et al. |
| 2014/0371622 A1 | 12/2014 | Hausman et al. |
| 2014/0375457 A1 | 12/2014 | Diaz |
| 2014/0378779 A1 | 12/2014 | Freeman et al. |
| 2014/0378789 A1 | 12/2014 | McKinley et al. |
| 2014/0378946 A1 | 12/2014 | Thompson et al. |
| 2014/0379045 A1 | 12/2014 | Rahimi et al. |
| 2014/0379049 A1 | 12/2014 | Mashiach et al. |
| 2015/0005607 A1 | 1/2015 | Cui et al. |
| 2015/0005680 A1 | 1/2015 | Lipani |
| 2015/0005840 A1 | 1/2015 | Pal et al. |
| 2015/0005841 A1 | 1/2015 | Pal et al. |
| 2015/0005851 A1 | 1/2015 | Bradley |
| 2015/0010607 A1 | 1/2015 | Francis et al. |
| 2015/0012079 A1 | 1/2015 | Goroszeniuk et al. |
| 2015/0016647 A1 | 1/2015 | Segovia Martinez |
| 2015/0017140 A1 | 1/2015 | Bhatia et al. |
| 2015/0018659 A1 | 1/2015 | Ware et al. |
| 2015/0032044 A9 | 1/2015 | Peyman |
| 2015/0032178 A1 | 1/2015 | Simon et al. |
| 2015/0032184 A1 | 1/2015 | Muccio |
| 2015/0038886 A1 | 2/2015 | Snow |
| 2015/0039055 A1 | 2/2015 | Wagner et al. |
| 2015/0049325 A1 | 2/2015 | Curtis |
| 2015/0051439 A1 | 2/2015 | Hillbratt |
| 2015/0051684 A1 | 2/2015 | Greenberg et al. |
| 2015/0057736 A1 | 2/2015 | Zachar |
| 2015/0059390 A1 | 3/2015 | Hayes |
| 2015/0062018 A1 | 3/2015 | Naidu et al. |
| 2015/0066126 A1 | 3/2015 | Marx et al. |
| 2015/0067422 A1 | 3/2015 | Hamilton |
| 2015/0073232 A1 | 3/2015 | Ahmad et al. |
| 2015/0073520 A1 | 3/2015 | Strahl et al. |
| 2015/0080709 A1 | 3/2015 | Chaturvedi |
| 2015/0080926 A1 | 3/2015 | Emery |
| 2015/0088030 A1 | 3/2015 | Taylor |
| 2015/0088223 A1 | 3/2015 | Blum et al. |
| 2015/0088224 A1 | 3/2015 | Goldwasser et al. |
| 2015/0088225 A1 | 3/2015 | Noble et al. |
| 2015/0102925 A1 | 4/2015 | Foldyna et al. |
| 2015/0105794 A1 | 4/2015 | Dhanasingh et al. |
| 2015/0105795 A1 | 4/2015 | Lenarz et al. |
| 2015/0112234 A1 | 4/2015 | McCaffrey et al. |
| 2015/0112321 A1 | 4/2015 | Cadouri |
| 2015/0112359 A1 | 4/2015 | Gillbe |
| 2015/0112360 A1 | 4/2015 | Pellinen et al. |
| 2015/0112404 A1 | 4/2015 | Holding et al. |
| 2015/0112405 A1 | 4/2015 | Brown et al. |
| 2015/0112408 A1 | 4/2015 | Kals |
| 2015/0119673 A1 | 4/2015 | Pellinen et al. |
| 2015/0119790 A1 | 4/2015 | Moffitt et al. |
| 2015/0119954 A2 | 4/2015 | Bhadra et al. |
| 2015/0119989 A1 | 4/2015 | Pimenta et al. |
| 2015/0126997 A1 | 5/2015 | Beetel et al. |
| 2015/0133761 A1 | 5/2015 | Vetter et al. |
| 2015/0133956 A1 | 5/2015 | Dayan et al. |
| 2015/0135840 A1 | 5/2015 | Sato et al. |
| 2015/0148643 A1 | 5/2015 | Small et al. |
| 2015/0148644 A1 | 5/2015 | Vaidyanathan et al. |
| 2015/0148736 A1 | 5/2015 | Jolly et al. |
| 2015/0148869 A1 | 5/2015 | Dorvall, II et al. |
| 2015/0148878 A1 | 5/2015 | Yoo et al. |
| 2015/0150508 A1 | 6/2015 | Glenn et al. |
| 2015/0157398 A1 | 6/2015 | Zarins et al. |
| 2015/0157851 A1 | 6/2015 | Sefkow et al. |
| 2015/0157854 A1 | 6/2015 | Hetke et al. |
| 2015/0157862 A1 | 6/2015 | Greenberg et al. |
| 2015/0164360 A1 | 6/2015 | Kipke et al. |
| 2015/0164401 A1 | 6/2015 | Toth et al. |
| 2015/0173673 A1 | 6/2015 | Toth et al. |
| 2015/0173918 A1 | 6/2015 | Herr et al. |
| 2015/0174403 A1 | 6/2015 | Pal et al. |
| 2015/0174418 A1 | 6/2015 | Tyler et al. |
| 2015/0182753 A1 | 7/2015 | Harris et al. |
| 2015/0190635 A1 | 7/2015 | Neuvonen et al. |
| 2015/0190636 A1 | 7/2015 | Simon et al. |
| 2015/0190637 A1 | 7/2015 | Simon et al. |
| 2015/0196767 A1 | 7/2015 | Ahmed |
| 2015/0201855 A1 | 7/2015 | Pellinen et al. |
| 2015/0202331 A1 | 7/2015 | Blumenfeld et al. |
| 2015/0202437 A1 | 7/2015 | Franke et al. |
| 2015/0209104 A1 | 7/2015 | Tran et al. |
| 2015/0209577 A1 | 7/2015 | Golestanirad et al. |
| 2015/0209586 A1 | 7/2015 | Silva et al. |
| 2015/0217125 A1 | 8/2015 | Chornenky et al. |
| 2015/0223731 A1 | 8/2015 | Sahin |
| 2015/0224300 A1 | 8/2015 | Hagr |
| 2015/0224330 A1 | 8/2015 | Kaib et al. |
| 2015/0230749 A1 | 8/2015 | Gharib et al. |
| 2015/0231396 A1 | 8/2015 | Burdick et al. |
| 2015/0235529 A1 | 8/2015 | Deschamps |
| 2015/0238104 A1 | 8/2015 | Tass |
| 2015/0238253 A1 | 8/2015 | Wu et al. |
| 2015/0238764 A1 | 8/2015 | Franke |
| 2015/0246072 A1 | 9/2015 | Bhatia et al. |
| 2015/0248470 A1 | 9/2015 | Coleman et al. |
| 2015/0251004 A1 | 9/2015 | Imran et al. |
| 2015/0254992 A1 | 9/2015 | Sethi |
| 2015/0257824 A1 | 9/2015 | Mauch |
| 2015/0272805 A1 | 10/2015 | Burnett et al. |
| 2015/0273206 A1 | 10/2015 | Monteiro |
| 2015/0283365 A1 | 10/2015 | Dacey, Jr. et al. |
| 2015/0284416 A1 | 10/2015 | Zhao |
| 2015/0290439 A1 | 10/2015 | Eldredge et al. |
| 2015/0290450 A1 | 10/2015 | Kolb et al. |
| 2015/0290464 A1 | 10/2015 | Monteiro |
| 2015/0290472 A1 | 10/2015 | Maguire et al. |

(56) References Cited

U.S. PATENT DOCUMENTS

| | | |
|---|---|---|
| 2015/0297104 A1 | 10/2015 | Chen et al. |
| 2015/0297444 A1 | 10/2015 | Tass |
| 2015/0297914 A1 | 10/2015 | Hamid et al. |
| 2015/0305667 A1 | 10/2015 | Durand |
| 2015/0305686 A1 | 10/2015 | Coleman et al. |
| 2015/0310762 A1 | 10/2015 | Seim et al. |
| 2015/0313498 A1 | 11/2015 | Coleman et al. |
| 2015/0313512 A1 | 11/2015 | Hausman et al. |
| 2015/0314017 A1 | 11/2015 | Zhao |
| 2015/0320560 A1 | 11/2015 | Mulliken et al. |
| 2015/0320588 A1 | 11/2015 | Connor |
| 2015/0321000 A1 | 11/2015 | Rosenbluth et al. |
| 2015/0321010 A1 | 11/2015 | Marnfeldt |
| 2015/0321017 A1 | 11/2015 | Perryman et al. |
| 2015/0322155 A1 | 11/2015 | Zhao |
| 2015/0328454 A1 | 11/2015 | Lambert |
| 2015/0328455 A1 | 11/2015 | Meadows et al. |
| 2015/0335288 A1 | 11/2015 | Toth et al. |
| 2015/0335876 A1 | 11/2015 | Jeffery et al. |
| 2015/0335877 A1 | 11/2015 | Jeffery et al. |
| 2015/0335883 A1 | 11/2015 | Halpern et al. |
| 2015/0335888 A1 | 11/2015 | Demers et al. |
| 2015/0343196 A1 | 12/2015 | Vasapollo |
| 2015/0343215 A1 | 12/2015 | De Ridder |
| 2015/0343242 A1 | 12/2015 | Tyler et al. |
| 2015/0354922 A1 | 12/2015 | Carriere |
| 2015/0359704 A1 | 12/2015 | Imboden et al. |
| 2015/0364018 A1 | 12/2015 | Mirov et al. |
| 2015/0374515 A1 | 12/2015 | Meijer et al. |
| 2015/0379880 A1 | 12/2015 | Sethi |
| 2016/0015962 A1 | 1/2016 | Maragheh et al. |
| 2017/0001003 A1 | 1/2017 | Pivonka et al. |
| 2017/0080216 A1 | 3/2017 | Pham |
| 2017/0209693 A1 | 7/2017 | An et al. |
| 2017/0224990 A1 | 8/2017 | Goldwasser et al. |
| 2017/0312512 A1 | 11/2017 | Creasey et al. |
| 2017/0312526 A1 | 11/2017 | Steinke et al. |
| 2017/0333695 A1 | 11/2017 | Kaplan et al. |
| 2018/0116877 A1 | 5/2018 | Ineichen |
| 2018/0133479 A1 | 5/2018 | Bennett et al. |
| 2018/0318585 A1 | 11/2018 | Pfeifer |
| 2020/0069941 A1 | 3/2020 | Campean et al. |
| 2020/0069942 A1 | 3/2020 | Campean et al. |

FOREIGN PATENT DOCUMENTS

| | | |
|---|---|---|
| FR | 2646779 B1 | 7/1993 |
| JP | 2011502707 A | 1/2011 |
| JP | 2012512682 A | 6/2012 |
| JP | 2013500080 A | 1/2013 |
| JP | 2013512076 A | 4/2013 |
| WO | 2009064641 A1 | 5/2009 |
| WO | 2011011748 A1 | 1/2011 |
| WO | 2011053607 A1 | 5/2011 |
| WO | 2012129574 A2 | 9/2012 |
| WO | 2015183620 A3 | 4/2016 |

OTHER PUBLICATIONS

US 8,613,701 B2, 12/2013, Rao et al. (withdrawn)
US 8,652,133 B2, 02/2014, Zarins et al. (withdrawn)
White, N, et al.; Overactive Bladder; Obstet Gynecol Clin North Am; 2016; 59-68; 43.
Vigil, HR, et al.; Urinary tract infection in the neurogenic bladder; Transl Androl Urol; 2016; 72-87; 5.
Su, X, et al.; Optimization of Neuromodulation for Bladder Control in a Rat Cystitis Model; Neuromodulation; 2016; 101-107; 19.
Speer, LM, et al.; Chronic Pelvic Pain in Women; Am Fam Physician; 2016; 380-387; 93.
Shah, P, et al.; Unique spatiotemporal neuromodulation of the lumbosacral circuitry shapes locomotor success after spinal cord injury; J Neurotrauma; 2016;Abstract,
Sanford, MT, et al.; Neuromodulation in neurogenic bladder; Transl Androl Urol; 2016; 117-126; 5.
Roth, TM; Safe Simultaneous Use of Sacral Neuromodulation and Vagal Nerve Stimulation; Female Pelvic Med Reconstr Surg; 2016; e1-2; 22;Abstract,
Puccini, F, et al.; Sacral neuromodulation: an effective treatment for lower urinary tract symptoms in multiple sclerosis; Int Urogynecol J; 2016; 347-354; 27.
Penson, DF; Re: Physician Use of Sacral Neuromodulation among Medicare Beneficiaries with Overactive Bladded and Urinary Retention; J Urol; 2016; 689; 195.
Olivera, CK, et al.; Non-antimuscarinic treatment for overactive bladder: a systematic review; Am J Obstet Gynecol; 2016;Abstract.
Noblett, K, et al.; Results of a prospective, multicenter study evaluating quality of life, safety, and efficacy of sacral neuromodulation at twelve months in subjects with symptoms of overactive bladder: Neurourol Urodyn: 2016: 246-251: 35.
Musco, S, et al.; Percutaneous Tibial Nerve Stimulation Improves Female Sexual Function in Women With Overactive Bladder Syndrome; J Sex Med; 2016
Mason, MD, et al.; Prospective Evaluation of Sacral Neuromodulation in Children: Outcomes and Urodynamic Predictors of Success; J Urol; 2016.
Manriquez, V, et al.; Transcutaneous posterior tibial nerve stimulation versus extended release oxybutynin in overactive bladder patients. A prospective randomized trial: Eur J Obstet Gynecol Reprod Biol: 2016: 42531: 196.
Lyon, TD, et al.; Pudendal but not tibial nerve stimulation inhibits bladder constractions induced by stimulation of pontine micturition center in cats; Am J Physiol Regul Integr Comp Physiol: 2016: R366-374: 310.
Iqbal, F, et al.; Bilateral transcutaneous tibial nerve stimulation for chronic constipation; Colorectal Dis; 2016; 173-178; 18.
Frokjaer, JB, et al.; Modulation of vagal tone enhances gastroduodenal motility and reduces somatic pain sensitivity; Neurogastroenterol Motil; 2016.
Evers, J, et al.; Reversal of sensory deficit through sacral neuromodulation in an animal model fo fecal incontinence; Neurogastroenterol Motil; 2016;Abstract.
Devane, LA, et al.; Acute lumbosacral nerve stimulation does not affect anorectal motor function in a rodent model; Neurogastroenterol Motil; 2016; 358-363; 28.
Choudhary, M, et al.; Inhibitory effects of tibial nerve stimulation on bladder neurophysiology in rats; Springerplus; 2016; 35; 5.
Cadish, LA, et al.; Stimulation latency and comparison of cycling regimens in women using sacral neuromodulation; Neurourol Urodyn; 2016;Abstract.
Batla, A, et al.; Lower urinary tract dysfunction in patients with functional movement disorders; J Neurol Sci; 2016; 192-194; 361.
Baron, M, et al.; [Does urinary sacral neuromodulation improve bowel symptoms other than fecal incontinence: A systematic review]; Prog Urol; 2016;Abstract.
Zecca, C, et al.; Posterior tibial nerve stimulation in the management of lower urinary tract symptoms in patients with multiple sclerosis; Int Urogynecol J; 2015.
Zariffa, J, et al.; A Phase-Based Electrical Plethysmography Approach to Bladder Volume Measurement; Ann Biomed Eng; 2015.
Yamanishi, T, et al.; Neuromodulation for the Treatment of Lower Urinary Tract Symptoms; Low Urin Tract Symptoms; 2015; 121-132; 7.
Williams, MJ, et al.; Self-Reported Medication Costs in Patients Receiving Sacral Neuromodulation for Overactive Bladder; Value Health; 2015; A352; 18.
Wexner, SD, et al.; Current surgical strategies to treat fecal incontinence; Expert Rev Gastroenterol Hepatol; 2015; 1577-1589; 9;Abstract.
Wenzler, DL, et al.; Proof of concept trial on changes in current perception threshold after sacral neuromodulation; Neuromodulation; 2015; 228-231; discussion 232; 18.
Wein, AJ; Re: Results of a Prospective, Randomized, Multicenter Study Evaluating Sacral Neuromodulation with InterStim Therapy Compared to Standard Medical Therapy at 6-Months in Subjects with Mild Symptoms of Overactive Bladder; J Urol; 2015; 1051-1052; 194.

(56) References Cited

OTHER PUBLICATIONS

Wark, HA, et al.; Restoration from acute urinary dysfunction using Utah electrode arrays implanted into the feline pudendal nerve; Neuromodulation; 2015; 317-323; 18.
Veit-Rubin, N, et al.; [Overactive bladder syndrome—a public health challenge]; Rev Med Suisse; 2015; 2016-2021; 11;Abstract.
Trevizol, AP, et al.; Trigeminal Nerve Stimulation (TNS) for the Treament of Irritable Bowel Syndrome in an Elderly Patient with Major Depressive Disorder: A Case Study; Brain Stimul; 2015; 1235-1236; 8.
Tian, Y, et al.; Inhibitory Effect and Possible Mechanism of Intraurethral Stimulation on Overactive Bladder in Female Rats; Int Neurourol J; 2015; 151-157; 19.
Thin, NN, et al.; Randomized clinical trial of sacral versus percutaneous tibial nerve stimulation in patients with faecal incontinence; Br J Surg; 2015; 349-358; 102.
Tweel, WA, et al.; Neurogenic bladder in spinal cord injury patients; Res Rep Urol; 2015; 85-99; 7.
Suskind, AM, et al.; Physician Use of Sacral Neuromodulation Among Medicare Beneficiaries With Overactive Bladder and Urinary Retention; Urology; 2015; 30-34;86.
Su, X, et al.; Differentiation and interaction of tibial versus spinal nerve stimulation for micturition control in the rat; Neurourol Urodyn; 2015; 92-97; 34.
Su, X, et al.; Preclinical assessment of potential interactions between botulinum toxin and neuromodulation for bladder micturition reflex; BMC Urol; 2015; 50; 15.
Siegel, S, et al.; Results of a prospective, randomized, multicenter study evaluating sacral neuromodulation with InterStim therapy compared to standard medical therapy at 6-months in subjects with mild symptoms of overactive bladder; Neurourol Urodyn; 2015; 224-230; 34.
Shvarts, PG, et al.; [The modern methods of the electical stimulation for the management of neurogenic disturbances of urination]; Vopr Kurortol Fizioter Lech Fiz Kult; 2015; 18-21; 92.
Shi, P, et al.; Bladder response to acute sacral neuromodulation while treating rats in different phases of complete spinal cord injury: a preliminary study; Int Braz J Urol; 2015; 1194-1201; 41.
Schurch, B, et al.; Dysfunction of lower urinary tract in patients with spinal cord injury; Handb Clin Neurol; 2015; 247-267; 130.
Scheiner, DA, et al.; [Interstitial cystitis/bladder pain syndrom (IC/BPS)]; Praxis (Bern 1994); 2015; 909-918; 104.
Sadiq, A, et al.; Management of neurogenic lower urinary tract dysfunction in multiple sclerosis patients; Curr Urol Rep; 2015; 44; 16.
Saber-Khalaf, M, et al.; Sacral neuromodulation outcomes in male patients with chronic urinary retention; Neuromodulation; 2015; 329-334; discussion 334; 18.
Rogers, MJ, et al.; Propranolol, but not naloxone, enhances spinal reflex bladder activity and reduces pudendal inhibition in cats; Am J Physiol Integr Comp Physiol; 2015; R42-49; 308.
Rogers, MJ, et al.; Role of glycine in nociceptive and non-nocicpetive bladder reflexes and pudendal afferent inhibition of these reflexes in cats; Neurourol Urodyn; 2015;Abstract.
Rimmer, CJ, et al.; Short-term Outcomes of a Randomized Pilot Trial of 2 Treatment Regimens of Transcutaneous Tibial Nerve Stimulation for Fecal Incontinence; Dis Colon Rectum; 2015; 974-982; 58.
Reese, JN, et al.; Role of spinal metabotropic glutamate receptor 5 in pudendal inhibition of the nociceptive bladder reflex in cats; Am J Physiol Renal Physiol; 2015; F832-838; 308.
Ramage, L, et al.; A systematic review of sacral nerve stimulation for low anterior resection syndrome; Colorectal Dis; 2015; 762-771; 17.
Rahnama'l, MS, et al.; Evidence for prostaglandin E2 receptor expression in the intramural ganglia of the guinea pig urinary bladder; J Chem Neuroanat; 2015; 43-47; 64-65.
Phe, V, et al.; How to define a refractory idiopathic overactive bladder?; Neurourol Urodyn; 2015; 42411; 34.

Peyronnet, B, et al.; [Management of overactive bladder in women]; Prog Urol; 2015; 877-883; 25;Abstract.
Peters, KM, et al.; Predictors of reoperation after sacral neuromodulation: A single institution evaluation of over 400 patients; Neurourol Urodyn; 2015;Abstract.
Peters, KM, et al.; Effect of Sacral Neuromodulation on Outcome Measures and Urine Chemokines in Interstitial Cystitis/Painful Bladder Syndrome Patients; Low Urin Tract Symptoms; 2015; 77-83; 7.
Patidar, N, et al.; Transcutaneous posterior tibial nerve stimulation in pediatric overactive bladder: A preliminary report; J Pediatr Urol; 2015; 351.e351-356; 11.
Parnell, BA, et al.; The effect of sacral neuromodulation on pudendal nerve function and female sexual function; Neurourol Urodyn; 2015; 456-460; 34.
Panicker, JN, et al.; Lower urinary tract dysfunction in the neurological patient: clinical assessment and management; Lancet Neurol; 2015; 720-732; 14.
Mishra, NN; Clinical presentation and treament of bladder pain syndrome/interstitial cystitis (BPS/IC) in India; Transl Androl Urol; 2015; 512-523; 4.
Meissnitzer, T, et al.; CT-Guided Lead Placement for Selective Sacral Neuromodulation to Treat Lower Urinary Tract Dysfunctions; AJR Am J Roentgenol; 2015; 1139-1142; 205.
Marinkovic, SP, et al.; Neuromodulation for Overactive Bladder Symptoms in Women Utilizing Either Motor or Sensory/Motor Provocation With a Minimum Nine-Year Follow-Up; Neuromodulation; 2015; 517-521; discussion 521; 18.
Maeda, Y, et al.; Sacral nerve stimulation for faecal incontinence and constipation: a European consensus statement; Colorectal Dis; 2015; O74-87; 17.
Lombardi, G, et al.; Sacral neuromodulation and female sexuality; Int Urogynecol J; 2015; 1751-1757; 26.
Lin, YT, et al.; Effects of pudendal neuromodulation on bladder function in chronic spinal cord-injured rats; J Formos Med Assoc; 2015.
Laudano, MA, et al.; Disparities in the Use of Sacral Neuromodulation among Medicare Beneficiaries; J Urol; 2015; 449-453; 194.
La, TH, et al.; Intermittent sacral neuromodulation for idiopathic urgency urinary incontinence in women; Neurourol Urodyn; 2015;Abstract.
Kuo, TL, et al.; Pelvic floor spasm as a cause of voiding dysfunction; Curr Opin Urol; 2015; 311-316; 25.
Kumsar, S, et al.; Effects of sacral neuromodulation on isolated urinary bladder function in a rat model of spinal cord injury; Neuromodulation; 2015; 67-74; discussion 74-65; 18.
Kovacevic, M, et al.; Reflex neuromodulation of bladder function elicited by posterior tibial nerve stimulation in anesthetized rats; Am J Physiol Renal Physiol; 2015; F320-329; 308.
Knowles, CH, et al.; Percutaneous tibial nerve stimulation versus sham electrical stimulation for the treatment of faecal incontinence in adults (CONFIDeNT): a double-blind, multicentre, pragmatic, parallel-group, randomised controlled trial; Lancet; 2015; 1640-1648; 386.
Karmarkar, R, et al.; Emergin drugs for overactive baldder; Expert Opin Emerg Drugs; 2015; 613-624; 20;Abstract.
Karam, R, et al.; Real-Time Classification of Bladder Events for Effective Diagnosis and Treatment of Urinary Incontinence; IEEE Trans Biomed Eng; 2015.
Joussain, C, et al.; Electrical managment of neurogenic lower urinary tract disorders; Ann Phys Rehabil Med; 2015; 245-250; 58.
Jin, H, et al.; Electrical neuromodulation at acupoint ST36 normalizes impaired colonic motility induced by rectal distension in dogs; Am J Physiol Gastrointest Liver Physiol; 2015; G368-376; 309.
Jimenez-Toscano, M, et al.; Efficacy and quality of life after transcutaneous posterior tibial neuromodulation for faecal incontinence; Colorectal Dis; 2015; 718-723; 17.
Jesus, LE, et al.; Psychosocial and respiratory disease related to severe bladder dysfunction and non-monosymptomatic enuresis; J Pediatr Urol; 2015;Abstract.
Horrocks, EJ, et al.; Double-blind randomised controlled trial of percutaneous tibial nerve stimulation versus sham electrical stimulation in the treatment of faecal incontinence: CONtrol of Faecal

(56) References Cited

OTHER PUBLICATIONS

Incontinence using Distal NeuromodulaTion (the CONFIDeNT trial); Health Technol Assess; 2015; 1-164; 19.
Hoag, N, et al.; Underactive Bladder: Clinical Features, Urodynamic Parameters, and Treatment; Int Neurourol J; 2015; 185-189; 19.
Hill, AJ, et al.; Resolution of Chronic Vulvar Pruritus With Replacement of a Neuromodulation Device; J Minim Invasive Gynecol; 2015; 889-891; 22.
Heinze, K, et al.; [Neuromodulation—new techniques]; Urologe A; 2015; 373-377; 54.
Hassouna, MM, et al.; Economic evaluation of sacral neuromodulation in overactive bladder: A Canadian perspective; Can Urol Assoc J; 2015; 242-247; 9.
Hashim, H, et al.; Patient preferences for treating refractory overactive bladder in the UK; Int Urol Nephrol; 2015; 1619-1627; 47.
Gupta, P, et al.; Percutaneous tibial nerve stimulation and sacral neuromodulation: an update; Curr Urol Rep; 2015; 4; 16.
Gormley, EA, et al.; Diagnosis and treatment of overactive bladder (non-neurogenic) in adults: AUA/SUFU guideline amendment; J Urol; 2015; 1572-1580; 193.
Franzen, K, et al.; Surgery for urinary incontinence in women 65 years and older: a systematic review; Int Urogynecol J; 2015; 1095-1102; 26.
Ford, AP, et al.; P2X3 receptors and sensitization of autonomic reflexes; Auton Neurosci; 2015; 16-24; 191.
Ferroni; MC, et al.; Role of the brain stem in tibial inhibition of the micturition reflex in cats; Am J Physiol Renal Physiol; 2015; F242-250; 309.
Drossaerts, J, et al.; Screening for depression and anxiety in patients with storage or voiding dysfunction: A retrospective cohort study predicting outcome of sacral neuromodulation: Neurourol Urodyn; 2015:Abstract.
Drossaerts, J, et al.; The value of urodynamic tools to guide patient selection in sacral neuromodulation; World J Urol; 2015; 1889-1895; 33.
Drake, MJ; Management and rehabilitation of neurologic patients with lower urinary tract dysfunction; Handb Clin Neurol; 2015; 451-468; 130.
Di Giovangiulio, M, et al.; The Neuromodulation of the Intestinal Immune System and its Relevance in Inflammatory Bowel Disease; Front Immunol; 2015; 590; 6.
Desrosiers, L, et al.; Urogynecologic conditions: interstitial cystitis/painful bladder syndrome; FP Essent; 2015; 17-22; 430;Abstract.
De Groat, WC, et al.; Impact of Bioelectronic Medicine on the Neural Regulation of Pelvic Visceral Function; Bioelectron Med; 2015; 25-36; 2015.
Comiter, CV; Conscious Neuromodulation of the Bladder before Clinical Use; J Urol; 2015; 16-17; 194.
Colaco, M, et al.; Current guidelines in the management of interstitial cystitis; Tranl Androl Urol; 2015; 677-683; 4.
Chan, DK, et al.; Effective treatment of dyssynergic defecation using sacral neuromodulation in a patient with cerebral palsy; Female Pelvic Med Reconstr Surg; 2015; e27-29; 21;Abstract.
Canbaz Kabay, S, et al.; Long term sustained therapeutic effects of percutaneous posterior tibial nerve stimulation treatment of neurogenic overactive bladder in multiple sclerosis patients; 12-months results; Neurourol Urodyn; 2015;Abstract.
Brown, ET, et al.; New evidence in the treatment of overactive bladder; Curr Opin Obstet Gynecol; 2015; 366-372; 27.
Brink, TS, et al.; A Chronic, Conscious Large Animal Platform to Quantify Therapeutic Effects of Sacral Neuromodulation on Bladder Function; J Urol; 2015; 252-258; 194.
Beusterien, K, et al.; Use of best-worst scaling to assess patient perceptions of treatments for refractory overactive bladder; Neurourol Urodyn; 2015;Abstract.
Bertapelle, MP, et al.; Sacral neuromodulation and Botulinum toxin A for refractory idiopathic overactive bladder: a cost-utility analysis in the perspective of Italian Healthcare System; World J Urol; 2015; 1109-1117; 33.
Bayrak, O, et al.; Botulinum toxin injections for treating neurogenic detrusor overactivity; Turk J Urol; 2015; 221-227; 41.
Banakhar, M, et al.; Sacral neuromodulation for Genitourinary Problems; Prog Neurol Surg; 2015; 192-199; 29;Abstract.
Aoun, F, et al.; [Lower urinary tract dysfunction following radical hysterectomy]; Prog Urol; 2015; 1184-1190; 25;Abstract.
Zheng, J, et al.; [Sacral Neuromodulation in the treatment of intractable constipation]; Zhonghua Wei Chang Wai Ke Za Zhi; 2015; 1175-1178; 17;Abstract.
Zhao, X, et al.; Diffused and sustained inhibitory effects of intestinal electrical stimulation on intestinal motility mediated via sympathetic pathway; Neuromodulation; 2014; 373-379; discussion 380; 17.
Zhang, N, et al.; Transcutaneous Neuromodulation at Posterior Tibial Nerve and ST36 for Chronic Constipation; Evid Based Complement Alternat Med; 2014; 560802; 2014.
Zecca, C, et al.; Motor and sensory responses after percutaneous tibial nerve stimulation in multiple sclerosis patients with lower urinary tract symptoms treated in daily practive; Eur J Neurol; 2014; 506-511; 21.
Yang, G, et al.; Pudendal nerve stimulation and block by a wireless-controlled implantable stimulator in cats; Neuromodulation; 2014; 490-496; discussion 496; 17.
Xiao, Z, et al.; Somatic modulation of spinal reflex bladder activity mediated by nociceptive bladder afferent nerve fibers in cats; Am J Physiol Renal Physiol; 2014; F673-679; 307.
Xiao, Z, et al.; Role of spinal GABAA receptors in pudendal inhibition of nociceptive and nonnociceptive bladder reflexes in cats; Am J Physiol Renal Physiol; 2014; F781-789; 306.
Wood, LN, et al.; Urinary incontinence in women; Bmj; 2014; g4531; 349.
Withington, J, et al.; The changing face of urinary continence surgery in England: a perspective from the Hospital Episode Statistics databse; BJU Int; 2014; 268-277; 114.
Wein, AJ; Re: inhibition of bladder overactivity by a combination of tibial neuromodulation and tramadol treatment in cats; J Urol; 2014; 868-869; 191.
Unger, CA, et al.; Fecal incontinence: the role of the urologist; Curr Urol Rep; 2014; 388; 15.
Tang, H, et al.; Combination of sacral neuromodulation and tolterodine of treatment of idiopathic overactive bladder in women: a clinical trial; Urol J; 2014; 1800-1805; 11.
Sillen, U, et al.; Effects of transcutaneous neuromodulation (TENS) on overactive bladder symptoms in children: a randomized controlled trial; J Pediatr Urol; 2014; 1100-1105; 10.
Shalom, DF, et al.; Sacral nerve stimulation reduces elevated urinary nerve growth factor levels in women with symptomatic detrusor overactivity; Am J Obstet Gynecol; 2014; 561 e561-565; 211.
Schwen, Z, et al.; Combination of foot stimulation and tolterodine treatment eliminates bladder overactivity in cats; Neurourol Urodyn; 2014; 1266-1271; 33.
Possover, M; A novel implantation technique for pudendal nerve stimulation for treatment of overactive bladder and urgency incontinence; J Minim Invasive Gynecol; 2014; 888-892; 21.
Pescatori, LC, et al.; Sphincteroplasty for anal incontinence; Gastroenterol Rep (Oxf); 2014; 92-97; 2.
Peeters, K, et al.; Long-term follow-up of sacral neuromodulation for lower urinary tract dysfunction; BJU Int; 2014; 789-794; 113.
Osman, NI, et al.; Fowler's syndrome—a cause of unexplained urinary retention in young women?; Nat Rev Urol; 2014; 87-98; 11;Abstract.
Noblett, KL, et al.; Sacral nerve stimulation for the treatment of refractory voiding and bowel dysfunction; Am J Obstet Gynecol; 2014; 99-106; 210.
Nambiar, A, et al.; Chapter 4: Guidelines for the diagnosis and treatment of overactive bladder (OAB) and neurogenic detrusor overactivity (NDO); Neurourol Urodyn; 2014; S21-25; 33 Suppl. 3.
Moon, KH, et al.; Prospective Trial of Sacral Neuromodulation for Refractory Overactive Bladder Syndrome in Korean Patients; Low Urin Tract Symptoms; 2014; 175-179; 6.
Mehnert, U, et al.; The management of urinary incontinence in the male neurological patient; Curr Opin Urol; 2014; 586-592; 24.

(56) References Cited

OTHER PUBLICATIONS

Mcnevin, MS, et al.; Outcomes associated with Interstim therapy for medically refractory fecal incontinence; Am J Surg; 2014; 735-737; discussion 737-788; 207.

Mayr, CA, et al.; Cost-effectiveness of novel therapies for overactive bladder; Expert Rev Pharmacoecon Outcomes Res; 2014; 527-535; 14.

Matsuta, Y, et al.; Poststimlation inhibition of the micturition reflex induced by tibial nerve stimulation in rats; Physiol Rep; 2014; e00205; 2.

Mamopoulos, A, et al.; Active sacral neuromodulation during pregnancy: a unique case report; Am J Obstet Gynecol; 2014; e4-5; 211.

Lowette, K, et al.; Role of corticosterone in the murine enteric nervous system during fasting; Am J Physiol Gastointest Liver Physiol; 2014; G905-913; 307.

Lopez-Delgado, A, et al.; Effect on anal pressure of percutaneous posterior tibial nerve stimulation for faecal incontinence; Colorectal Dis; 2014; 533-537; 16.

Lombardi, G, et al.; Sacral neuromodulation for neurogenic nonobstructive urinary retention in incomplete spinal cord patients: a ten-year follow-up single-centre experience; Spinal Cord; 2014; 241-245; 52.

Lippmann, QK, et al.; Successful use of sacral neuromodulation in a 12-year-old with cerebral palsy and neurogenic bladder; Neuromodulation; 2014; 396-398; 17.

Levy, RM; The evolving definition of neuromodulation, Neuromodulation; 2014; 207-210; 17.

Levin, PJ, et al.; Psychosocial factors related to the use of InterStim(R) for the treatment of refractory overactive bladder; Female Pelvic Med Reconstr Surg; 2014; 272-275; 20;Abstract.

Lee, YY; What's New in the Toolbox for Constipation and Fecal Incontinence?; Front Med (Lausanne); 2014; 5; 1.

Laviana, A, et al.; Sacral neuromodulation for refractory overactive bladder, interstitial cystitis, and painful bladder syndrome; Neurosurg Clin N Am; 2014; 33-46; 25.

Kurpad, R, et al.; The evaluation and management of refractory neurogenic overactive bladder; Curr Urol Rep; 2014; 444; 15.

Knupfer, SC, et al.; Protocol for a randomized, placebo-controlled, double-blind clinical trial investigating sacral neuromodulation for neurogenic lower urinary tract dysfunction; BMC Urol; 2014; 65; 14.

Kessler, TM, et al., Urologists' referral attitude for sacral neuromodulationfor treating refractory idiopathic overactive bladder syndrome: discrete choice experiment; Neurourol Urodyn; 2014; 1240-1246; 33.

Johnsen, NV, et al.; The role of electrical stimulation techniques in the management of the male patient with urgency incontinence; Curr Opin Urol; 2014; 560-565; 24.

Jacobs, SA, et al.; Randomized prospective crossover study of interstim lead wire placement with curved versus straight stylet; Neurourol Urodyn; 2014; 488-492; 33.

Hotouras, A, et al.; Prospective clinical audit of two neuromodulatory treatments for fecal incontinence: sacral nerve stimulation (SNS) and percutaneouls tibial nerve stimulation (PTNS); Surg Today; 2014; 2124-2130; 44.

Hamann, MF, et al.; [Urinary incontinence in men and woman. Diagnostics and conservative therapy]; Urologe A; 2014; 1073-1084; quiz 1085-1076; 53.

Grossi, U, et al.; Sacral neuromodulation for anorectal dysfunction secondary to congenital imperforate anus: report of two cases; Int J Colorectal Dis; 2014; 889-890; 29.

Giarenis, I, et al.; Managing urinary incontinence: what works?; Climacteric; 2014; 26-33; 17 Suppl 2;Abstract.

Foditsch, EE, et al.; Laparoscopic placement of a tined lead electrode on the pudendal nerve with urodynamic monitoring of bladder function during electrical stimulation: an acute experimental study in healthy female pigs; Springerplus; 2014; 309; 3.

Faucheron, JL, et al.; Sacral neuromodulation for bowel dysfunction; Tech Coloproctol; 2014; 42433; 18.

Falletto, E, et al.; Sacral neuromodulation for bowel dysfunction: a consensus statement from the Italian group; Tech Coloproctol; 2014; 53-64; 18.

Evers, J, et al.; Effects of stimulation frequency and intensity in sacral neuromodulation on anorectal inputs to the somatosensory cortex in an experimental model; Br J Surg; 2014; 1317-1328; 101.

Elneil, S, et al.; Optimizing the duration of assessment of stage-1 sacral Neuromodulation in nonobstructive chronic urinary retention; neuromodulation; 2014; 66-70; discussion 70-61; 17.

Duelund-Jakobsen, J, et al.; Baseline factors predictive of patient satisfaction with sacral neuromodulation for idiopathic fecal incontinence; Int J Colorectal Dis; 2014; 793-798; 29.

Donon, L, et al.; [Sacral neuromodulation: results of a monocentric study of 93 patients]; Prog Urol; 2014; 1120-1131; 24;Abstract.

Chen, ML, et al.; Electrical stimulation of somatic afferent nerves in the foot increases bladder capacity in healthy human subjects; J Urol; 2014; 1009-1013; 191.

Chen, G, et al.; Sacral neuromodulation for neurogenic bladder and bowel dysfunction with multiple symptoms secondary to spinal cord disease; Spinal Cord; 2014;Abstract.

Chandra, A, et al.; Neuromodulation of perineally transposed antropylorus with pudendal nerve anastomosis following total anorectal reconstruction in humans; Neurogastroenterol Motil; 2014; 1342-1348; 26.

Carrington, EV, et al.; A systematic review of sacral nerve stimulation mechanisms in the treatment of fecal incontinence and constipation; Neurogastroenterol Motil; 2014; 1222-1237; 26.

Carlucci, L, et al.; Functional variability of sacral roots in bladder control; J Neurosurg Spine; 2014; 961-965; 21.

Campin, L, et al.; [Urinary functional disorders bound to deep endometriosis and to its treatment: review of the literature]; J Gynecol Obstet Biol Reprod (Paris); 2014; 431-442; 43;Abstract.

Burnstock, G; Purinergic signalling in the gastrointestinal tract and related organs in health and disease; Purinergic Signal; 2014; 18323; 10.

Buhmann, H, et al.; [Update on fecal incontinence]; Praxis (Bern 1994); 2014; 1313-1321; 103.

Gross, T, et al.; Transcutaneous Electrical Nerve Stimulation for Treating Neurogenic Lower Urinary Tract Dysfunction: A Systematic Review; Eur Urol; 2016;Abstract.

Bouguen, G, et al.; Effects of transcutaneous tibial nerve stimulation on anorectal physiology in fecal incontinence: a double-blind placebo-controlled cross-over evaluation; Neurogastroenterol Motil; 2014; 247-254; 26.

Banakhar, M, et al.; Effect of sacral neuromodulation on female sexual function and quality of life: Are they correlated?; Can Urol Assoc J; 2014; E762-767; 8.

Balchandra, P, et al.; Women's perspective: intra-detrusor botox versus sacral neuromodulation for overactive bladder symptoms after unsuccessful anitcholinerig treatment; Int Urogynecol J; 2014; 1059-1064; 25.

Anger, JT, et al.; The effect of sacral neuromodulation on anticholinergic use and expenditures in a privately insured population; Neuromodulation; 2014; 72-74; discussion 74; 17.

Amundsen, CL, et al.; The Refractory Overactive Bladder: Sacral NEuromodulation vs. BoTulinum Toxin Assessment: ROSETTA trial; Contemp Clin Trials; 2014; 272-283; 37

Abraham, N, et al.; Urgency after a sling: review of the management; Curr Urol Rep; 2014; 400; 15.

Zhang, F, et al.; Neural pathways involved in sacral neuromodulation of reflex bladder activity in cats; Am J Physiol Renal Physiol; 2013; F710-717; 304.

Yih, JM, et al.; Changes in sexual functioning in women after neuromodulation for voiding dysfunction; J Sex Med; 2016; 2477-2483; 10.

Wein, AJ; Re: is on-demand sacral neuromodulation in patients with OAB syndrome a feasible therapy regime?; J Urol; 2013; 610-611; 189.

Veeratterapillay, R, et al.; Augmentation cystoplasty: Contemporary indications, techniques and complications; Indian J Urol; 2013; 322-327; 29.

(56) References Cited

OTHER PUBLICATIONS

Tirlapur, Sa, et al.; Nerve stimulation for chronic pelvic pain and bladder pain syndrome: a systematic review; Acta Obstet Gynecol Scand; 2013; 881-887; 92
Thomas, GP, et al.; A pilot study of transcutaneous sacral nerve stimulation for faecal incontinence; Colorectal Dis; 2013; 1406-1409; 15.
Thomas, GP, et al.; Sacral nerve stimulation for faecal incontinence secondary to congenital imperforate anus; Tech Coloproctol; 2013; 227-229; 17.
Thin, NN, et al.; Systematic review of the clinical effectiveness of neuromodulation in the treatment of faecal incontinence; Br J Surg; 2013; 1430-1447; 100.
Suskin, AM, et al.; Understanding the dissemination of sacral neuromodulation; Surg Innov; 2013; 625-630; 20.
Su, X, et al., Role of the endogenous opioid system in modulation of urinary bladder activity by spinal nerve stimulation; Am J Physiol Renal Physiol; 2013; F52-60; 305.
Su, X, et al.; Quantification of effectivenss of bilateral and unilateral neuromodulation in the rat bladder rhythmic contraction model; BMC Urol; 2013; 34; 13.
Su, X, et al.; Neuromodulation attenuates bladder hyperactivity in a rat cystitis model; BMC Urol; 2013; 70; 13.
Stephany, HA, et al.; Prospective evaluation of sacral nerve modulation in children with validated questionnaires; J Urol; 2013; 1516-1522; 190.
Smits, MA, et al.; Sacral neuromodulation in patients with idiopathic overactive bladder after initial botulinum toxin therapy; J Urol; 2013; 2148-2152; 190.
Shi, P, et al.; Effects of acute sacral neuromodulation on bladder reflex in complete spinal cord injury rats; Neuromodulation; 2013; 583-589; discussion 589; 16.
Sherif, H, et al.; Posterior tibial nerve stimulation as treatment for the overactive bladder; Arab J Urol; 2013; 131-135; 11.
Sharma, A, et al.; Review of sacral neuromodulation for management of constipation; Surg Innov; 2013; 614-624; 20.
Schwen, Z, et al.; Involvement of 5-HT3 receptors in pudendal inhibition of bladder overactivity in cats; Am J Physiol Renal Physiol; 2013; F663-671; 305.
Schwen, Z, et al.; Inhibition of bladder overactivity by duloxetine in combination with foot stimulation or WAY-100635 treatment in cats; Am J Physiol Renal Physiol; 2013; F1663-1668; 305.
Schuns, O, et al.; Development and characterization of [123]iodotiagabine for in-vivo GABA-transporter imaging; Nucl Med Commun; 2013; 175-179; 34;Abstract.
Robinson, D, et al.; The medical management of refractory overactive bladder; Maturitas; 2013; 386-390; 74.
Robinson, D, et al.; The management of overactive bladder refractory to medical therapy; Maturitas; 2013; 101-104; 75.
Rashid, TG, et al.; Male incontinence: onabotulinum toxin A and sacral nerve stimulation; Curr Opin Urol; 2013; 545-551; 23.
Rana, MV, et al.; Tripolar spinal cord stimulation for the treatment of abdominal pain associated with irritable bowel syndrome; Neuromodulation; 2013; 73-77; discussion 77; 16.
Pucciani, F; A review on functional results of sphincter-saving surgery for rectal cancer: the anterior resection syndrome; Updates Surg; 2013; 257-263; 65.
Peters, KM, et al.; Effect of Sacral Neuromodulation Rate on Overactive Bladder Symptoms: A Randomized Crossover Feasibility Study; Low Urin Tract Symptoms; 2013; 129-133; 5.
Peters, KM, et al.; Does patient age impact outcomes of neuromodulation?; Neurourol Urodyn; 2013; 30-36; 32.
Peters, KM, et al.; Clinical outcomes of sacral neuromodulation in patients with neurologic conditions; Urology; 2013; 738-743; 81.
Peters, KM, et al.; Percutaneous tibial nerve stimulation for the long-term treatment of overactive bladder: 3-year results of the STEP study; J Urol; 2013; 2194-2201; 189.
Peng, CW, et al.; Pudendal neuromodulation with a closed-loop control strategy to improve bladder functions in the animal study; Conf Proc IEEE Eng Med Biol Soc; 2013; 3626-3629; 2013.

Osman, NI, et al.; Overactive bladder syndrome: Current pathophysiological concepts and therapeutic approaches; Arab J Urol; 2013; 313-318; 11.
Offiah, I, et al.; Interstitial cystitis/bladder pain syndrome: diagnosis and management; Int Urogynecol J; 2013; 1243-1256; 24.
Schneider, MP, et al.; Tibial Nerve Stimulation for Treating Neurogenic Lower Urinary Tract Dysfunction: A Systematic Review; Eur Urol; 2015; 859-867; 68.
Natalin, R, et al., Management of OAB in those over age 65; Curr Urol Rep; 2013; 379-385; 14.
Murphy, AM, et al., Treatment of overactive bladder: what is on the horizon?; Int Urogynecol J; 2013; 42503; 24.
Matsuta, Y, et al.; Effect of methysergide on pudendal inhibition of micturition reflex in cats; Exp Neurol; 2013; 250-258; 247.
Matsuta, Y, et al.; Contribution of opioid and metabotropic glutamate receptor mechanisms to inhibition of bladder overactivity by tibial nerve stimulation; Am J Physiol Regul Integr Comp Physiol; 2013; R126-133; 305.
Martinson, M, et al.; Cost of neuromodulation therapies for overactive bladder: percutaneous tibial nerve stimulation versus sacral nerve stimulation; J Urol; 2013; 2010-216; 189.
Mally, AD, et al.; Role of opioid and metabotropic glutamate 5 receptors in pudendal inhibition of bladder overactivity in cats; J Urol; 2013; 1574-1579; 189.
Maher, RM, et al.; A novel externally applied neuromuscular stimulator for the treatment of stress urinary incontinence in women—a pilot study; Neuromodulation; 2013; 590-594; discussion 594; 16.
Lombardi, G, et al.; Intravesical electrostimulation versus sacral neuromodulation for incomplete spinal cord patients suffering from neurogenic non-obstructive urinary retention; Spinal Cord; 2013; 571-578; 51.
Kantartzis, KL, et al.; Cost-effectiveness of test phase implantation strategies for InterStim(R) sacral neuromodulation; Female Pelvic Med Reconstr Surg; 2013; 322-327; 19;Abstract.
Kacker, R, et al.; Electrical and mechanical office-based neuromodulation; Urol Clin North Am; 2013; 581-589; 40.
Jadav, AM, et al.; Does sacral nerve stimulation improve global pelvic function in women?; Colorectal Dis; 2013; 848-857; 15.
Hyun, SJ, et al.; Comparative analysis between thoracic spinal cord and sacral neuromodulation in a rat spinal cord injury model: a preliminary report of a rat spinal cord stimulation model; Korean J Spine; 2013; 14-18; 10.
Hull, T, et al.; Long-term durability of sacral stimulation therapy for chronic fecal incontinence; Dis Colon Rectum; 2013; 234-245; 56.
Hersh, L, et al.; Clinical management of urinary incontinence in women; Am Fam Physician; 2013; 634-640; 87.
Hellstrom, PA, et al.; Sacral nerve stimulation lead implantation using the O-arm; BMC Urol; 2013; 48; 13.
Hassouna, M; Sacral neuromodulation for overactive bladder: Is it worth it?; Can Urol Assoc J; 2013; E454; 7.
Gleason, JL, et al.; Sacral neuromodulation effects on periurethral sensation and urethral sphincter activity; Neurourol Urodyn; 2013; 476-479; 32.
Gibbons, SJ et al.; Review article: carbon monoxide in gastrointestinal physiology and its potential in therapeutics; Aliment Pharmacol Ther; 2013; 689-702; 38.
Giarenis, I, et al.; Management of refractory overactive bladder; Minerva Ginecol; 2013; 41-52; 65;Abstract.
Firoozi, F, et al.; Increasing patient preparedness for sacral neuromodulation improves patient reported outcomes despite leaving objective measures of success unchanged; J Urol; 2013; 594-597; 190.
Ellsworth, P, et al.; Neurogenic detrusor overactivity: an update on management options; R I Med J (2013); 2013; 38-40; 96.
Dudding, TC, et al.; Sacral nerve stimulation: an effective treatment for chronic functional anal pain?; Colorectal Dis; 2013; 1140-1144; 15.
Davis, T, et al.; Sacral neuromodulation outcomes for the treatment of refractory idiopathic detrusor overactivity stratified by indication: Lack of anticholinergic efficacy versus intolerability; Can Urol Assoc J; 2013; 176-178; 7.
Cornu, JN; Actual treatment of overactive bladder and urge urinary incontinence; Minerva Urol Nefrol; 2013; 21-35; 65;Abstract.

(56) References Cited

OTHER PUBLICATIONS

Chiarioni, G, et al.; Neuromodulation for fecal incontinence: an effective surgical intervention; World J Gastroenterol; 2013; 7048-7054; 19.
Chen, SC, et al.; Pudendal neuromodulation improvies voiding efficiency in diabetic rats; Neurourol Urodyn; 2013; 293-300; 32.
Carlson, JJ, et al.; Estimating the cost-effectiveness of onabotulinumtoxinA for neurogenic detrusor overactivity in the United States; Clin Ther; 2013; 414-424; 35.
Cameron, AP, et al.; Battery explanation after sacral neuromodulation in the Medicare population; Neurourol Urodyn; 2013; 238-241; 32.
Burnstock, G; Introduction and perspective, historical note; Front Cell Neurosci; 2013; 227; 7.
Brown, SR, et al.; Surgery for faecal incontinence in adults; Cochrane Database Syst Rev; 2013; Cd001757; 7.
Bleier, JI, et al.; Surgical management of fecal incontinence; Gastroenterol Clin North Am; 2013; 815-836; 42.
Biemans, JM, et al.; Efficacy and effectiveness of percutaneous tibial nerve stimulation in the treatment of pelvic organ disorders: a systematic review; Neuromodulation; 2013; 25-33; discussion 33; 16.
Benson-Cooper, S, et al.; Introduction of sacral neuromodulation for the treatment of faecal incontinence; N Z Med J; 2013; 47-53; 126.
Bartley, JM, et al.; Understanding clinic options for overactive bladder; Curr Urol Rep; 2013; 541-548; 14.
Bartley, J, et al.; Neuromodulation for overactive bladder; Nat Rev Urol; 2013; 513-521; 10.
Barroso, U, JR., et al.; Posterior tibial nerve stimulation vs parasacral transcutaneous neuromodulation for overactive bladder in children; J Urol; 2013; 673-677; 190.
Barnett, G, et al.; Re: Cost of neuromodulation therapies for overactive bladder: percutaneous tibial nerve stimulation versus sacral nerve stimulation: m. Martinson, S. MacDiarmid and E. Black J Urol 2013; 189; 210-216; J Urol; 2013; 1444-1445; 190.
Amend, B, et al.; Prolonged percutaneous SNM testing does not cause infection-related explanation; BJU Int; 2013; 485-491; 111.
Abdel Raheem, A, et al.; Voiding dysfunction in women: How to manage it correctly; Arab J Urol; 2013; 319-330; 11.
Zhang, F, et al.; Inhibition of bladder overactivity by a combination of tibial neuromodulation and tramadol treatment in cats; Am J Physiol Renal Physiol; 2012; F1576-1582; 302.
Worsoe, J, et al.; Turning off sacral nerve stimulation does not affect gastric and small intestinal motility in patients treated for faecal incontinence; Colorectal Dis; 2012; e713-720; 14.
Van Wunnik, BP, et al.; Cost-effectiveness analysis of sacral neuromodulation for faecal incontinence in The Netherlands; Colorectal Dis; 2012; e807-814; 14.
Van Wunnik, BP, et al.; Sacral neuromodulation therapy: a promising treatment for adolescents with refractory functional constipation; Dis Colon Rectum; 2013; 278-285; 55.
Van Ophoven, A, et al., [The future of invasive neuromodulation: new techniques and expanded indications]; Urologe A; 2012; 212-216; 51.
Tai, C, et al.; Bladder inhibition by intermittent pudendal nerve stimulation in cat using transdermal amplitude-modulated signal (TAMS); Neurourol Urodyn; 2012; 1181-1184; 31.
Tai, C, et al.; Inhibition of bladder overactivity by stimulation of feline pudendal nerve using transdermal amplitude-modulated signal (TAMS); BJU Int; 2012; 782-787; 109.
Su, X, et al.; Neuromodulation in a rat model of the bladder micturition reflex; Am J Physiol Renal Physiol; 2012; F477-486; 302.
Su, X, et al.; Comparison of neural targets for neuromodulation of bladder micturition reflex in the rat; Am J Physiol Renal Physiol; 2012; F1196-1206; 303.
Steanu, ID, et al,; The Place of the Ice Water Test (IWT) in the Evaluation of the Patients with Traumatic Spinal Cord Injury; Maedica (Buchar); 2012; 125-130; 7.
Srivastava, D; Efficacy of sacral neuromodulation in treating chronic pain related to painful bladder syndrome/interstitial cystitis in adults; J Anaesthesiol Clin Pharmacol. 2012; 428-435; 28.
Snellings, AE, et al.; Effects of stimulation site and stimulation parameters on bladder inhibition by electrical nerve stimulation; BJU Int; 2012; 136-143; 110
Smits, MA, et al.; [Neuromodulation as a treatment for overactive bladder syndrome]; Ned Tijdschr Geneeskd; 2012; A4135; 156;Abstract.
Smith, AL, et al.; Contemporary management of overactive bladder; Postgrad Med; 2012; 104-116; 124;Abstract.
Sivalingam, N, et al.; Concepts in the management of the overactive bladder in women; Med J Malaysia; 2012; 137-141; quiz 142; 67.
Sievert, KD, et al.; [Unconventional treatment procedures of the bladder in paraplegia and myelomeningocele]; Urologe A; 2012; 1692-1696; 51.
Schwalenberg, T, et al.; [Sacral neuromodulation in urology—development and current status]; Aktuelle Urol; 2012; 39-48; 43;Abstract.
Sajadi, KP, et al.; Bladder augmentation and urinary diversion for neurogenic LUTS: current indications; Curr Urol Rep; 2012; 389-393; 13.
Robinson, D, et al.; Overactive bladder: diagnosis and management; Maturitas; 2012; 188-193; 71.
Rawashdeh, YF, et al.; International Children's Continence Society's recommendations for therapeutic intervention in congenital neurophatic bladder and bowel dysfunction in children; Neurourol Urodyn; 2012; 615-620; 31.
Rai, BP, et al.; Anticholinergic drugs versus non-drug active therapies for non-neurogenic overactive bladder syndrome in adults; Cochrane Database Syst Rev; 2012; Cd003193; 12;Abstract.
Qin, C, et al.; Is constant current or constant voltage spinal cord stimulation superior for the suppression of nociceptive visceral and somatic stimuli? A rat model; Neuromodulation; 2012; 132-142; discussion 143; 15.
Peters, KM; Sacral neuromodulation is an effective treatment for interstitial cystitis/bladder pain syndrome: pro; J Urol; 2012; 2043-2044; 188.
Penson, DF; Re: Cost-effectiveness analysis of sacral neuromodulation and botulinum toxin a treatment for patients with idiopathic overactive bladder; J Urol; 2012; 2157-2158; 187.
Otto, W, et al.; [Sacral neuromodulation as second-line treatment strategy for lower urinary tract symptoms of various aetiologies: experience of a German high-volume clinic]; Aktuelle Urol; 2012; 162-166; 43;Abstract.
Meurette, G, et al.; Sacral nerve stimulation enhances epithelial barrier of the rectum: results from a porcine model; Neurogastroenterol Motil; 2012; 267-273, e110; 24.
Mehnert, U, et al.; [Neuro-urological dysfunction of the lower urinary tract in CNS diseases: pathophysiology, epidemiology, and treatment options]; Urologe A; 2012; 189-197; 51.
Majerus, SJ, et al.; Wireless, Ultra-Low-Power Implantable Sensor for Chronic Bladder Monitoring; ACM J Emerg Technol Comput Syst; 2012;8.
Madersbacher, H, et al.; What are the causes and consequences of bladder overdistention? ICI-RS 2011; Neurourol Urodyn; 2012; 2012; 317-321; 31.
Levin, PJ, et al.; The efficacy of posterior tibial nerve stimulation for the treatment of overactive bladder in women: a systematic review; Int Urogynecol J; 2012; 1591-1597; 23.
Leicht, W, et al.; [Botulinum toxin versus sacral neuromodulation for idiopathic detrusor overactivity]; Urologe A; 2012; 348-351; 51.
Lay, AH, et al.; The role of neuromodulation in patients with neurogenic overactive bladder; Curr Urol Rep; 2012; 343-347; 13.
Koldewun; EL; [What to do if pills do not work for urge incontinence—still many questions and ambiguities]; Ned Tijdschr Geneeskd; 2012; A5099; 156;Abstract.
Kessler, TM, et al.; [Sacral neuromodulation for neurogenic bladder dysfunction]; Urologe A; 2012; 179-183; 51.
Kantartzis, K, et al.; Sacral neuromodulation and intravesical botulinum toxin for refractory overactive bladder; Curr Opin Obstet Gynecol; 2012; 331-336; 24.
Hubsher, CP, et al.; Sacral nerve stimulation for neuromodulation of the lower urinary tract; Can J Urol; 2012; 6480-6484; 19.

(56) References Cited

OTHER PUBLICATIONS

Guerci, B, et al.; Gastric electrical stimulation for the treatment of diabetic gastroparesis; Diabetes Metab; 2012; 393-402; 38.
Groen, LA, et al.; Sacral neuromodulation with an implantable pulse generator in children with lower urinary tract symptoms; 15-year experience; J Urol; 2012; 1313-1317; 188.
Gill, BC, et al.; Improvement of bower dysfunction with sacral neuromodulation for refractory urge urinary incontinence; Int Urogynecol J; 2012; 735-741; 23.
Ghiselli, R, et al.; Nitric oxide synthase expression in rat anorectal tissue after sacral neuromodulation; J Surg Res; 2012; 29-33; 176.
Evans, RJ; Sacral neuromodulation is an effective treatment for interstitial cystitis/bladder pain syndrome: con; J Urol; 2012; 2044-2045; 188.
Elser, DM; Stress urinary incontinence and overactive bladder syndrome: current options and new targets for management; Postgrad Med; 2012; 42-49; 124;Abstract.
Elkelini, MS, et al.; Mechanism of action of sacral nerve stimulation using a transdermal amplitude-modulated signal in a spinal cord injury rodent model; Can Urol Assoc J; 2012; 227-230; 6.
Dwyer, ME, et al.; The dysfunctional elimination syndrome in children—is sacral neuromodulation worth the trouble?; J Urol; 2012; 1076-1077; 188.
Devroede, G, et al.; Quality of life is markedly improved in patients with fecal incontinence after sacral nerve stimulation; Female Pelvic Med Reconstr Surg; 2012; 103-112; 18;Abstract.
Denzinger, S, et al.; Does sacral neuromodulation lead to relevant reduction in the need for intermittent catheterization? A single-center experience on patients with chronic urinary retention; Neuromodulation; 2012; 586-591; discussion 591; 15.
Del Popolo, G, et al.; [Standard pharmacological treatment and new therapies for overactive bladder]; Urologia; 2012; 42534; 79.
Crock, LW, et al.; Central amygdala metabotropic glutamate receptor 5 in the modulation of visceral pain; J Neurosci; 2012; 14217-14226; 32.
Chen, G, et al.; The inhibitory effects of pudendal nerve stimulation on bladder overactivity in spinal cord injury dogs: is early stimulation necessary?; Neuromodulation; 2012; 232-237; discussion 237; 15.
Cardarelli, S, et al.; Efficacy of sacral neuromodulation on urological diseases: a multicentric research project; Urologia; 2012; 90-96; 79.
Burnstock, G; Purinergic signalling: Its unpopular beginning, its acceptance and its exciting future; Bioessays; 2012; 218-225; 34.
Banakhar, MA, et al.; Sacral neuromodulation and refractory overactive bladder: an emerging tool for an old problem; Ther Adv Urol; 2012; 179-185; 4.
Arrabal-Polo, MA, et al.; Clinical efficacy in the treatment of overactive bladder refractory to anticholinergics by posterior tibial nerve stimulation; Korean J Urol; 2012; 483-486; 53.
Arnold, J, et al.; Overactive bladder syndrome—management and treatment options; Aust Fam Physician; 2012; 878-883; 41.
Allahdin, S, et al.; An overview of treatment of overactive bladder syndrome in women; J Obstet Gynaecol; 2012; 217-221; 32.
Zullo, MA, et al.; Sacral neuromodulation after stabilization of L2-S1 vertebrae with metallic fixation devices: is it feasbile?; Int Urogynecol J; 2011; 373-375; 22.
Yazdany, T, et al.; Determining outcomes, adverse events, and predictors of success after sacral neuromodulation for lower urinary disorders in women; Int Urogynecol J; 2011; 1549-1554; 22.
Wu, JM, et al.; Patient preferences for different severities of and treatments for overactive bladder; Female Pelvic Med Reconstr Surg; 2011; 184-189; 17;Abstract.
Van Wunnik, BP, et al.; Patient experience and satisfaction with sacral neuromodulation: results of a single-center sample survey; Dis Colon Rectum; 2011; 95-100; 54.
Van Wunnik, BP, et al.; Neuromodulation for constipation: sacral and transcutaneous stimulation; Best Pract Res Clin Gastroenterol; 2011; 181-191; 25.

Van Koeveringe, GA, et al.; Detrusor underactivity: a plea for new approaches to a common bladder dysfunction; Neurourol Urodyn; 2011; 723-728; 30.
Van Kerrebroeck, P; Editorial comment re: Killinger et al. "Secondary changes in bowel function after successful treatment of voiding symptoms with neuromodulation"; Neurourol Urodyn; 2011; 1403; 30.
Vaarala, MH, et al.; Sacral neuromodulation in urological indications: the Finnish experience; Scand J Urol Nephrol; 2011; 46-51; 45.
Uludag, O, et al.; Sacral neuromodulation: long-term outcome and quality of life in patients with faecal incontinence; Colorectal Dis; 2011; 1162-1166; 13.
Ullah, S, et al.; Temporary gastric neuromodulation for intractable nausea and vomiting; Ann R Coll Surg Engl; 2011; 624-628; 93.
Thoua, NM, et al.; Internal anal sphincter atropy in patients with systemic sclerosis; Rheumatology (Oxford); 2011; 1596-1602; 50.
Tai, C, et al.; Prolonged poststimulation inhibition of bladder activity induced by tibial nerve stimulation in cats; Am J Physiol Renal Physiol; 2011; F385-392; 300.
Tai, C, et al.; Irritation induced bladder overactivity is suppressed by tibial nerve stimulation in cats; J Urol; 2011; 326-330; 186.
Signorello, D, et al.; Impact of sacral neuromodulation on female sexual function and his correlation with clinical outcome and quality of life indexes: a monocentric experience; J Sex Med; 2011; 1147-1155; 8.
Shepherd, JP, et al.; InterStim Sacral Neuromodulation and Botox Botulinum-A Toxin Intradetrusor Injections for Refractory Urge Urinary Incontinence: A Decision Analysis Comparing Outcomes Including Efficacy and Complications; Female Pelvic Med Reconstr Surg; 2011; 199-203; 17;Abstract.
Shen, B, et al.; Neuromodulation of bladder activity by stimulation of feline pudendal nerve using a transdermal amplitude modulated signal (TAMS); Neurourol Urodyn; 2011; 1686-1694; 30.
Sharma, A, et al.; Sacral neuromodulation for the management of severe constipation: development of a constipation treatment protocol; Int J Colorectal Dis; 2011; 1583-1587; 26.
Sahai, A, et al.; Neurogenic detrusor overactivity in patients with spinal cord injury: evaluation and management; Curr Urol Rep; 2011; 404-412; 12.
Richter, EO, et al.; Percutaneous cephalocaudal implantation of epidural stimulation electrodes over sacral nerve roots—a technical note on the importance of the lateral approach; Neuromodulation; 2011; 62-67; discussion 67; 14.
Possover, M, et al.; Risks, symptoms, and management of pelvic nerve damage secondary to surgery for pelvic organ prolapse: a report of 95 cases; Int Urogynecol J; 2011; 1485-1490; 22.
Peters, KM, et al.; Is sensory testing during lead placement crucial for achieving positive outcomes after sacral neuromodulation?; Neurourol Urodyn; 2011; 1489-1492; 30.
Pena, G, et al.; Cholinergic regulatory lymphocytes re-establish neuromodulation of innate immune responses in sepsis; J Immunol; 2011; 718-725; 187.
Pascual, I, et al.; Sacral nerve stimulation for fecal incontinence; Rev Esp Enferm Dig; 2011; 355-359; 103.
Oerlemans, DJ, et al.; Is on-demand sacral neuromodulation in patients with OAB syndrome a feasible therapy regime?; Neurourol Urodyn; 2011; 1493-1496; 30.
Miotla, P, et al.; [Sacral nerve stimulation in the treatment of the lower urinary tract function disorders]; Ginekol Pol; 2011; 851-856; 82.
Marcelissen, TA, et al.; The use of bilateral sacral nerve stimulation in patients with loss of unilateral treatment efficacy; J Urol; 2011; 976-980; 185.
Marcelissen, TA, et al.; Psychological and psychiatric factors as predictors for success in sacral neuromodulation treatment; BJU Int; 2011; 1834-1838; 108.
Marcelissen, TA, et al.; The effect of pulse rate changes on the clinical outcome of sacral neuromodulation; J Urol; 2011; 1781-1785; 185.
Marcelissen, T, et al.; Is the screening method of sacral neuromodulation a prognostic factor for long-term success?; J Urol; 2011; 583-587; 185.

(56) References Cited

OTHER PUBLICATIONS

Marcelissen, T, et al.; Sacral neuromodulation as a treatment for chronic pelvic pain; J Urol; 2011; 387-393; 186.
Majerus, SJ, et al.; Low-power wireless micromanometer system for acute and chronic bladder-pressure monitoring; IEEE Trans Biomed Eng; 2011; 763-767; 58.
Lombardi, G, et al.; Clinical concomitant benefits on pelvic floor dysfunctions after sacral neuromodulation in patients with incomplete spinal cord injury; Spinal Cord; 2011; 629-636; 49.
Liberman, D, et al.; Concerns regarding sacral neuromodulation as a treatment option for medical-refractory overactive bladder; Can Urol Assoc J; 2011; 285-287; 5.
Leong, RK, et al.; Satisfaction and patient experience with sacral neuromodulation: results of a single center sample survey; J Urol. 2011; 588-592; 185.
Leong, RK, et al.; PNE versus 1st stage tine lead procedure: a direct comparison to select the most sensitive test method to identify patients suitable for sacral neuromodulation therapy; Neurourol Urodyn; 2011; 1249-1252; 30.
Leong, RK, et al.; Cost-effectiveness analysis of sacral neuromodulation and botulinum toxin A treatment for patients with idiopathic overactive bladder; BJU Int; 2011; 558-564; 108.
Le, NB, et al.; Expanding the Role of Neuromodulation for Overactive Bladder: New Indications and Alternatives to Delivery; Curr Bladder Dysfunct Rep; 2011; 25-30; 6.
Kubota, M, et al.; Effect of neuromodulation with sacral magnetic stimulation for intractable bowel or bladder dysfunction in postoperative patients with anorectal malformation; a preliminary report; Pediatr Surg Int; 2011; 599-603; 27.
Knupfer, S, et al.; [Therapy-refractory overactive bladder: alternative treatment approaches]; Urologe A; 2011; 806-809; 50.
Killinger, KA, et al.; Seconary changes in bowel function after successful treatment of voiding symptoms with neuromodulation; Neurourol Urodyn; 2011; 133-137; 30.
Griffin, KM, et al.; Sacral nerve stimulation increases activation of the primary somatosensory cortex by anal canal stimulation in an experimental model; Br J Surg; 2011; 1160-1169; 98.
Gill, BC, et al.; Improved sexual and urinary function in women with sacral nerve stimulation; Neuromodulation; 2011; 436-443; discussion 443; 14.
Ghazwani, YQ, et al.; Efficacy of sacral neuromodulation in treatment of bladder pain syndrome: long-term follow-up; Neurourol Urodyn; 2011; 1271-1275; 30.
George, E, et al.; Use of combined anticholinergic medication and sacral neuromodulation in the treatment of refractory overactive bladder; Female Pelvic Med Reconstr Surg; 2011; 97-99; 17;Abstract.
Gajewski, JB, et al.; The long-term efficacy of sacral neuromodulation in the management of intractable cases of bladder pain syndrome: 14 years of experience in one centre; BJU Int; 2011; 1258-1264; 107.
Gaj, F, et al.; [Chronic pelvic pain treatment with posterior tibial nerve stimulation]; Clin Ter; 2011; e111-114; 162;Abstract,
Duthie, JB, et al.; Botulinum toxin injections for adults with overactive bladder syndrome; Cochrane Database Syst Rev; 2011; Cd005493.
Dudding, TC, et al.; Sacral nerve stimulation for faecal incontinence: optimizing outcome and managing complications; Colorectal Dis; 2011; e196-202; 13.
Dudding, TC, et al.; Sacral nerve stimulation for faecal incontinence: patient selection, service provision and operative technique; Colorectal Dis; 2011; e187-195; 13.
Dudding, TC; Future indications for sacral nerve stimulation; Colorectal Dis; 2011; 23-28; 13 Suppl 2.
De Gennaro, M, et al.; Current state of nerve stimulation technique for lower urinary tract dysfunction in children; J Urol; 2011; 1571-1577; 185.
Chartier-Kastler, E, et al.; [Sacral neuromodulation with InterStim system: Results from the French national register]; Prog Urol; 2011; 209-217; 21;Abstract.
Chaabane, W, et al.; Sacral neuromodulation for treating neurogenic bladder dysfunction: clinical and urodynamic study; Neurourol Urodyn; 2011; 547-550; 30.
Burnstock, G, et al.; P2X receptors in health and disease; Adv Pharmacol; 2011; 333-372; 61;Abstract.
Burnstock, G; Intrductory overview of purinergic signalling; Front Biosci (Elite Ed); 2011; 896-900; 3;Abstract.
Baeten, CG; Status of sacral neuromodulation for refractory constipation; Colorectal Dis; 2011; 19-22; 13 Suppl 2.
Atnip, S, et al.; A unique approach to severe constipation; Urol Nurs; 2011; 348-350; 31.
Arlandis, S, et al.; Cost-effectivenss of sacral neuromodulation compared to botulinum neurotoxin a or continued medical management in refractory overactive bladder; Value Health; 2011; 219-228; 14.
Apostolidis, A; Neuromodulation for intractable OAB; Neurourol Urodyn; 2011; 766-770; 30.
Al-Zharani, AA, et al.; Long-term outcome and surgical interventions after sacral neuromodulation implant for lower urinary tract symptoms: 14-year experience at 1 center; J Urol; 2011; 981-986; 185.
Al-Shaui, TF, et al.; Pelvic electrical neuromodulation for the treatment of overactive bladder syndrome; Adv Urol; 2011; 757454; 2011.
Zempleni, MZ, et al.; Cortical substrate of bladder control in SCI and the effect of peripheral pudendal stimulation; Neuroimage; 2010; 2983-2994; 48.
Yoong, W, et al.; Neuromodulative treatment with percutaneous tibial nerve stimulation for intractable detrusor instability: outcomes following a shortened 6-week protocol; BJU Int; 2010; 1673-1676; 106.
Wolff, K, et al.; Functional outcome and quality of life after stapled transanal rectal resection for obstructed defecation syndrome; Dis Colon Rectum; 2010; 881-888; 53.
Wehbe, SA, et al.; Sacral neuromodulations for femal lower urinary tract, pelvic floor, and bowel disorders; Curr Opin Obstet Gyncol; 2010; 414-419; 22.
Wehbe, SA, et al.; Minimally invasive therapies for chronic pelvic pain syndrome; Curr Urol Rep; 2010; 276-285; 11.
Watanabe, JH, et al.; Cost analysis of interventions for antimuscarinic refractory patients with overactive bladder; Urology; 2010; 835-840; 76.
Vasdev, N, et al.; The surgical management of the refractory overactive bladder; Indian J Urol; 2010; 263-269; 26.
Van Kerrebroeck, PE; Advances in the role of sacral nerve neuromodulation in lower urinary tract symptoms; Int Urogynecol J; 2010; S467-474; 21 Suppl 2.
Vallet, C, et al.; Sacral nerve stimulation for faecal incontinence: response rate, satisfaction and the value of preoperative investigation in patient selection; Colorectal Dis; 2010; 247-253; 12.
Uludag, O, et al.; Sacral neuromodulation: does it affect the rectoanal angle in patients with fecal incontinene?; World J Surg; 2010; 1109-1114; 34.
Thompson, JH, et al.; Sacral neuromodulation: Therapy evolution; Indian J Urol; 2010; 379-384; 26.
Stoffel, JT; Contemporary management of the neurogenic bladder for multiple sclerosis patients; Urol Clin North Am; 2010; 547-557; 37.
Starkman, JS, et al.; Surgical options for drug-refractory overactive bladder patients; Rev Urol; 2010; e97-e110; 12.
Sievert, KD, et al.; Early sacral neuromodulation prevents urinary incontinence after complete spinal cord injury; Ann Neurol; 2010; 74-84; 67.
Sancaktar, M, et al.; The outcome of adding peripheral neuromodulation (Stoller afferent neuro-stimulation) to anti-muscarinic therapy in women with severe overactive bladder; Gynecol Endocrinol; 2010; 729-732; 26.
Sajadi, KP, et al.; Overactive bladder after sling surgery; Curr Urol Rep; 2010; 366-371; 11.
Roth, TM; Sacral neuromodulation and cardiac pacemakers; Int Urogynecol J; 2010; 1035-1037; 21.
Roth, TM; Subcapsular relocation for sacral neuromodulation pulse generator implant revision; Neuromodulation; 2010; 145-146; 13.

(56) References Cited

OTHER PUBLICATIONS

Riguad, J, et al.; [Specific treatments for painful bladder syndrome]; Prog Urol; 2010; 1044-1053; 20;Abstract.
Ridout, AE, et al.; Tibial nerve stimulation for overactive bladder syndrome unresponsive to medical therapy; J Obstet Gynaecol; 2010; 111-114; 30.
Reyblat, P, et al.; Augmentation enterocystoplasty in overactive bladder: is there still a role?; Curr Urol Rep; 2010; 432-439; 11.
Powell, CR, et al.; Long-term outcomes of urgency-frequency syndrome due to painful bladder syndrome treated with sacral neuromodulation and analysis of failures; J Urol; 2010; 173-176; 183.
Possover, M; The laparoscopic implantation of neuroprothesis to the sacral plexus for therapy of neurogenic bladder dysfunctions after failure of percutaneous sacral nerve stimulation; Neuromodulation; 2010; 141-144; 13.
Peters, KM, et al.; Chronic pudendal neuromodulation: expanding available treatment options for refractory urologic symptoms; Neurourol Urodyn; 2010; 1267-1271; 29.
Peters, KM, et al.; Randomized trial of percutaneous tibial nerve stimulation versus Sham efficacy in the treatment of overactive bladder syndrome: results from the SUmiT trial; J Urol; 2010; 1438-1443; 183.
Peters, KM; Alternative approaches to sacral nerve stimulation; Int Urogynecol J; 2010; 1559-1563; 21.
Peirce, C, et al.; Central representation of the inferior rectal nerve of the rat; Dis Colon Rectum; 2010; 315-320; 53.
Oom, DM, et al.; Is sacral neuromodulation for fecal incontinence worthwhile in patients with associated pelvic floor injury?; Dis Colon Rectum; 2010; 422-427; 53.
Occhino, JA, et al.; Sacral nerve modulation in overactive bladder; Curr Urol Rep; 2010; 348-352; 11.
Nilsson, KF, et al.; Estimation of endogenous adenosine activity at adenosine receptors in guinea-pig ileum using a new pharmacological method; Acta Physiol (Oxf); 2010; 231-241; 199.
Mayer, R; Neuromodulation—who, what, when, where and why?; J Urol; 2010; 17-18; 183.
Marcelissen, TA, et al.; Long-term results of sacral neuromodulation with the tined lead procedure; J Urol; 2010; 1997-2000; 184.
Lombardi, G, et al.; Clinical outcome of sacral neuromodulation in incomplete spinal cord-injured patients suffering from neurogenic bowel dysfunctions; Spinal Cord; 2010; 154-159; 48.
Leong, RK, et al.; Current information on sacral neuromodulation and botulinum toxin treatment for refractory idiopathic overactive bladder syndrome: a review; Urol Int; 2010; 245-253; 84.
Kim, JH, et al.; Sacral nerve stimulation for treatment of intractable pain associated with cauda equina syndrome; J Korean Neurosurg Soc; 2010; 473-476; 47.
Kavia, R, et al.; A funcational magnetic resonance imaging study of the effect of sacral neuromodulation on brain responses in women with Fowler's syndrome; BJU Int; 2010; 366-372; 105.
Karram, MM; Sacral neuromodulation: emerging technology with expanding indications; Int Urogynecol J; 2010; 1443; 21.
Kacker, R, et al.; Selection of ideal candidates for neuromodulation in refractory overactive bladder; Curr Urol Rep; 2010; 372-378; 11.
Indinnimeo, M, et al.; Sacral neuromodulation for the treatment of fecal incontinence: analysis of cost-effectiveness; Dis Colon Rectum; 2010; 1661-1669; 53.
Hull, TL; Sacral neuromodulation stimulation in fecal incontinence; Int Urogynecol J; 2010; 1565-1568; 21.
Hoda, MR, et al.; [Sacral neuromodulation in urology. The emperor's new clothes or effective high-tech medicine]; Urologe A; 2010; 1254-1259; 49.
Haddad, M, et al.; Sacral neuromodulation in children with urinary and fecal incontinence: a multicenter, open label, randomized, crossover study; J Urol; 2010; 696-701; 184.
Gulur, DM, et al.; Management of overactive bladder; Nat Rev Urol; 2010; 572-582; 7.

French, JS, et al.; What do spinal cord injury consumers want? A review of spinal cord injury consumer priorities and neuroprosthesis from the 2008 neural interfaces conference; Neuromodulation; 2010; 229-231; 13.
Foon, R, et al.; The overactive bladder; Ther Adv Urol; 2010; 147-155; 2.
Findlay, JM, et al.; Peripheral neuromodulation via posterior tibial nerve stimulation—a potential treatment for faecal incontinence?; Ann R Coll Surg Engl; 2010; 385-390; 92.
Fariello, JY, et al.; Sacral neuromodulation stimulation for IC/PBS, chronic pelvic pain, and sexual dysfunction; Int Urogynecol J; 2010; 1553-1558; 21.
Fall, M, et al.; EAU guidelines on chronic pelvic pain; Eur Urol; 2010; 35-48; 57.
Elneil, S; Urinary retention in women and sacral neuromodulation; Int Urogynecol J; 2010; S475-483; 21 Suppl 2.
Ellsworth, P, et al.; Update on the pharmacologic management of overactive bladder: the present and the future; Urol Nurs; 2010; 29-38, 53; 30.
Daniels, DH, et al.; Sacral neuromodulation in diabetic patients: success and complications in the treatment of voiding dysfunction; Neurourol Urodyn; 2010; 578-581; 29.
Carr, MC; Conservative nonsurgical management of spina bifida; Curr Urol Rep; 2010; 109-113; 11.
Cardot, V, et al.; [Guidelines for the treatment of urinary incontinence in women with refractory idiopathic vesical hyperactivity using sacral neuromodulation]; Prog Urol; 2010; S161-169; 20 Suppl 2;Abstract.
Burks, FN, et al.; Neuromodulation and the neurogenic bladder; Urol Clin North Am; 2010; 559-565; 37.
Brouwer, R, et al.; Sacral nerve neuromodulation is effective treatment for fecal incontinence in the presence of a sphincter defect, pudendal neuropathy, or previous sphincter repair; Dis Colon Rectum; 2010; 273-278; 53.
Bosch, JL, et al.; What treatment should we use if drugs fail for OAB; and, what really works after drugs?; Neurourol Urodyn; 2010; 658-661; 29.
Bosch, JL; An update on sacral neuromodulation: where do we stand with this in the management of lower urinary tract dysfunction in 2010?; BJU Int; 2010; 1432-1442; 105.
Amend, B, et al.; [Second-line therapy of idiopathic detrusor overactivity. Sacral neuromodulation and botulinum toxin A]; Urologe A; 2010; 245-252; 49.
Wyndaele, JJ; Clinical outcomes of sacral neuromodulation in incomplete spinal cord injured patient suffering from neurogenic lower urinary tract symptoms; Spinal Cord; 2009; 427; 47.
Wosnitzer, MS, et al.; The use of sacral neuromodulation for the treatment of non-obstructive urinary retention secondary to Guillain-Barre syndrome; Int Urogynecol J Pelvic Floor Dysfunct; 2009; 1145-1147; 20.
Wooldridge, LS; Percutaneous tibial nerve stimulation for the treatment of urinary frequenc, urinary urgency, and urge incontinence: results from a community-based clinic; Urol Nurs; 2009; 177-185; 29.
Vignes, JR, et al.; Animal models of sacral neuromodulation for detrusor overactivity; Neurourol Urodyn; 2009; 42594; 28.
Scaglia, M, et al.; Fecal incontinence treated with acupuncture—a pilot study; Auton Neurosci; 2009; 89-92; 145.
Roth, TM; Blunt trauma leading to delayed extrusion of sacral nerve implant; Int Urogynecol J Pelvic Floor Dysfunct; 2009; 735-737; 20.
Rasmussen, NT, et al.; Successful use of sacral neuromodulation after failed bladder augmentation; Can Urol Assoc J; 2009; E49-50; 3.
Possover, M, et al.; Neuromodulation of the superior hypogastric plexus: a new option to treat bladder atonia secondary to radical pelvic surgery?; Surg Neurol; 2009; 573-576; 72.
Possover, M; The sacral LION procedure for recovery of bladder/rectum/sexual functions in paraplegic patients after explanation of a previous Finetech-Brindley controller; J Minim Invasive Gynecol; 2009; 98-101; 16.

(56) References Cited

OTHER PUBLICATIONS

Possover, M; Laparoscopic management of endopelvic etiologies of pudendal pain in 134 consecutive patients; J Urol; 2009; 1732-1736; 181.
Oom, DM, et al.; Anterior sphincteroplasty for fecal incontinence: a single center experience in the era of sacral neuromodulation; Dis Colon Rectum; 2009; 1681-1687; 52.
Moutzouris, DA, et al.; Interstitial cystitis: an unsolved enigma; Clin J Am Soc Nephrol; 2009; 1844-1857; 4.
Lombardi, G, et al.; Clinical outcome of sacral neuromodulation in incomplete spinal cord injured patients suffering from neurogenic lower urinary tract symptoms; Spinal Cord; 2009; 486-491; 47.
Kohli, N, et al.; InterStim Therapy: A Contemporary Approach to Overactive Bladder; Rev Obstet Gyncol; 2009; 18-27; 2.
Kaufmann, S, et al.; Unilateral vs bilateral sacral neuromodulation in pigs with formalin-induced detrusor hyperactivity; BJU Int; 2009; 260-263; 103.
Ingber, MS, et al.; Neuromodulation and female sexual function: does treatment for refractory voiding symptoms have an added benefit?; Int Urogynecol J Pelvic Floor Dysfunct; 2009; 1055-1059; 20.
Herbison, GP, et al.; Sacral neuromodulation with implanted devices for urinary storage and voiding dysfunction in adults: Cochrane Database Syst Rev; 2009; Cd004202.
Hartmann, KE, et al.; Treatment of overactive bladder in women; Evid Rep Techol Assess (Full Rep); 2009; 1-120, v.
Govaert, B, et al.; Neuromodulation for functional bowel disorders; Best Pract Res Clin Gastroenterol; 2009; 545-553; 23.
Game, X, et al.; [Alternative treatments for interstitial cystitis]; Prog Urol; 2009; 357-363; 19;Abstract.
Fu, G, et al.; [Neuromodulation for treatment for neurogenic bowel dysfunction]; Zhonghua Wai Ke Za Zhi; 2009; 128-131; 47.
Finazzi-Agro, E, et al.; Percutaneous tibial nerve stimulation produces effects on brain activity: study on the modifications of the long latency somatosensory evoked potentials; Neurourol Urodyn; 2009; 320-324; 28.
Falletto, E, et al.; Is sacral nerve stimulation an effective treatment for chronic idiopathic anal pain?; Dis Colon Rectum; 2009; 456-462; 52.
Chatoor, D, et al.; Constipation and evacuation disorders; Best Pract Res Clin Gastroenterol; 2009; 517-530; 23.
Charter-Kastler, E, et al.; [Update on the second line management of idiopathic overactive bladder]; Prog Urol; 2009; 530-537; 19;Abstract.
Chapple, C, et al.; The second-line management of idiopathic overactive bladder: what is the place of sacral neuromodulation and botulinum toxin-A in contemporary practice?; BJU Int; 2009; 1188-1190; 104.
Campbell, JD, et al.; Treatment success for overactive bladder with urinary urge incontinence refractory to oral antimuscarinics: a review of published evidence; BMC Urol; 2009; 18; 9.
Burnstock, G; Purinergic signalling: past, present and future; Braz J Med Biol Res; 2009; 42437; 42.
Burnstock, G; Purinergic cotransmission; F1000 Biol Rep; 2009; 46; 1.
Burks, FN, et al.; Neuromodulation versus medication for overactive bladder: the case for early intervention; Curr Urol Rep; 2009; 342-346; 10.
Bolton, JF, et al.; Neuromodulation 10 years on: how widely should we use this technique in bladder dysfunction?; Curr Opin Urol; 2009; 375-379; 19.
Badlani, GH; Update on lower urinary tract symptoms; ScientificWorldJournal; 2009; 499-500; 9.
Antolak, SJ, JR., et al.; Therapeutic pudendal nerve blocks using corticosteroids cure pelvic pain after failure of sacral neuromodulation; Pain Med; 2009; 186-189; 10.
Zabihi, N, et al.; Short-term results of bilateral S2-S4 sacral neuromodulation for the treatment of refractory interstitial cystitis, painful bladder syndrome, and chronic pelvic pain; Int Urogynecol J Pelvic Floor Dysfunct; 2008; 553-557; 19.

Tjandra, JJ, et al.; Sacral nerve stimulation is more effective than optimal medical therapy for severe fecal incontinence: a randomized, controlled study; Dis Colon Rectum; 2008; 494-502; 51.
Starkman, JS, et al.; Refractory overactive bladder after urethrolysis for bladder outlet obstruction: management with sacral neuromodulation; Int Urogynecol J Pelvic Floor Dysfunct; 2008; 277-282; 19.
Starkman, JS, et al.; The evolution of obstruction induced overactive bladder symptoms following urethrolysis for female bladder outlet obstruction; J Urol; 2008; 1018-1023; 179.
Spinelli, M, et al.; Latest techologic and surgical developments in using InterStim Therapy for sacral neuromodulation: impact on treatment success and safety; Eur Urol; 2008; 1287-1296; 54.
Smaldone, MC, et al.; Neuromodulation versus neurotoxin for the treatment of refractory detrusor overactivity: for neurotoxin; Nat Clin Pract Urol; 2008; 120-121; 5.
Skobejko-Wlodarska, L; [Non-neurogenic lower urinary tract dysfunctioin]; Pol Merkur Lekarski; 2008; 131-137; 24 Suppl 4;Abstract.
Seth, A, et al.; What's new in the diagnosis and management of painful bladder syndrome/interstitial cystitis?; Curr Urol Rep; 2008; 349-357; 9.
Robaina Padron, FJ; [Surgical neuromodulation: new frontiers in neurosurgery]; Neurocirugia (Astur); 2008; 143-155; 19;Abstract.
Rittenmeyer, H; Sacral nerve neuromodulation (InterStim). Part I: Review of the InterStim system; Urol Nurs; 2008; 15-20; 28.
Peters, KM, et al.; Characterization of a clinical cohort of 87 women with interstitial cystitis/painful bladder syndrome; Urology; 2008; 634-640; 71.
Perrigot, M, et al., [Perineal electrical stimulation and rehabilitation in urinary incontinence and other symptoms of non-neurologic origin]; Ann Readapt Med Phys; 2008; 479-490; 51;Abstract.
Oerlemans, DJ, et al.; Sacral nerve stimulation for neuromodulation of the lower urinary tract; Neurourol Urodyn; 2008; 28-33; 27.
O'Reilly, BA, et al., A prospective randomised double-blind controlled trial evaluating the effect of trans-sacral magnetic stimulation in women with overactive bladder; Int Urogynecol J Pelvic Floor Dysfunct; 2008; 497-502; 19.
Nitti, VW; Urodynamics, Incontinence, and Neurourology: Highlights from the Society for Urodynamics and Female Urology Annual Winter Meeting, Feb. 28-Mar. 2, 2008; Miami Fl; Rev Urol; 2008; 229-231; 10
Nakib, N, et al.; Neuromodulation versus neurotoxin for the treatment of refractory detrusor overactivity: for neuromodulation; Nat Clin Pract Urol; 2008; 118-119; 5.
Minardi, D, et al.; Activity and expression of nitric oxide synthase in rat bladder after sacral neuromodulation; Int J Immunopathol Pharmacol; 2008; 129-135; 21;Abstract.
Milne, JL; Behavioral therapies for overactive bladder: making sense of the evidence; J Wound Ostomy Continence Nurs; 2008; 93-101; quiz 102-103; 35;Abstract.
Mckertich, K; Urinary incontinence-procedural and surgical treatments for women; Aust Fam Physician; 2008; 122-131; 37.
Lombardi, G, et al.; Clinical female sexual outcome after sacral neuromodulation implant for lower urinary tract symptom (LUTS); J Sex Med; 2008; 1411-1417; 5.
Lombardi, G, et al.; Sacral neuromodulation for lower urinary tract dysfunction and impact on erectile function; J Sex Med; 2008; 2135-2140; 5.
Liao, KK, et al.; Effect of sacral neuromodulation on the spinal nociceptive reflex of patients with idiopathic overactive bladder; Neuromodulation; 2008; 50-55; 11.
Kutzenberger, J; [Neurogenic urinary incontinence. Value of surgical management]; Urologe A; 2008; 699-706; 47.
Kosan, M, et al.; Alteration in contractile responses in human detrusor smooth muscle from obstructed bladders with overactivity; Urol Int; 2008; 193-200; 80.
Indar, A, et al.; A dual benefit of sacral neuromodulation; Surg Innov; 2008; 219-222; 15.
Groenendijk, PM, et al.; Urodynamic evaluation of sacral neuromodulation for urge urinary incontinence; BJU Int; 2008; 325-329; 101.
Game, X, et al.; Outcome after treatment of detrusor-sphincter dyssynergia by temporary stent; Spinal Cord; 2008; 74-77; 46.

(56) References Cited

OTHER PUBLICATIONS

Game, X; [Sacral neuromodulation and sexuality]; Prog Urol; 2008; 167; 18;Abstract.
Ferhi, K, et al.; [Results of sacral posterior neuromodulation on voiding disorders and impact on sexuality based on a single-center study]; Prog Urol; 2008; 160-166; 18;Abstract.
Faucheron, JL; [Anal incontinence]; Presse Med; 2008; 1447-1462; 37;Abstract.
Fang, Q, et al.; [Morphological study on the role of ICC-like cells in detrusor neuromodulation of rat urinary bladder]; Zhonghua Wai Ke Za Zhi; 2008; 1542-1545; 46.
Doumouchtsis, SK, et al.; Female voiding dysfuncation; Obstet Gynecol Surv; 2008; 519-526; 63.
De Seze, M, et al.; [Peripheral electrical stimulation in neurogenic bladder]; Ann Readapt Med Phys; 2008; 473-478; 51;Abstract.
De Boer, TA, et al.; [Male urinary incontinence]; Ned Tijdschr Geneeskd; 2008; 797-802; 152;Abstract.
Chartier-Kastler, E; Sacral neuromodulation for treating the symptoms of overactive bladder syndrome and non-obstructive urinary retention: >10 years of clinical experience; BJU Int; 2008; 417-423; 101.
Burnstock, G; The journey to establish purinergic signalling in the gut; Neurogastroenterol Motil; 2008; 42601; 20 Suppl 1.
Brosa, M, et al.; Cost-effectiveness analysis of sacral neuromodulation (SNM) with Interstim for fecal incontinence patients in Spain; Curr Med Res Opin; 2008; 907-918; 24.
Bannowsky, A, et al.; Urodynamic changes and response rates in patients treated with permanent electrodes compared to conventional wire electrodes in the peripheral nerve evaluation test; World J Urol; 2008; 623-626; 26.
Vignes, JR, et al.; Sacral neuromodulation as a functional treatment of bladder overactivity; Acta Neurochir Suppl; 2007; 315-322; 97;Abstract.
Vasavada, SP, et al.; Neuromodulation techniques: a comparison of available and new therapies; Curr Urol Rep; 2007; 455-460; 8.
Van Voskuilen, AC, et al.; Medium-term experience of sacral neuromodulation by tined lead implantation; BJU Int; 2007; 107-110; 99.
Van Kerrebroeck, PE, et al.; Results of sacral neuromodulation therapy for urinary voiding dysfunction: outcomes of a prospective, worldwide-clinical study; J Urol; 2007; 2029-2034; 178.
Van Balken, MR; Percutaneous tibial nerve stimulation: the Urgen PC device; Expert Rev Med Devices; 2007; 693-698; 4.
Unwala, DJ, et al.; Repeated botulinum toxin injection for idiopathic overactive bladder: will chemodenervation become a long-term solution?; Curr Urol Rep; 2007; 41-424; 8.
Starkman, JS, et al.; Management of refractory urinary urge incontinence following urogynecological surgery with sacral neuromodulation, Neurourol Urodyn; 2007; 29-35; discussion 36; 26.
South, MM, et al.; Detrusor overactivity does not predict outcome of sacral neuromodulation test stimulation; Int Urogynecol J Pelvic Floor Dysfunct; 2007; 1395-1398; 18.
Sherman, ND, et al.; Current and future techniques of neuromodulation for bladder dysfunction; Curr Urol Rep; 2007; 448-454; 8.
Shamliyan, T, et al.; Prevention of urinary and fecal incontinence in adults; Evid Rep Technol Assess (Full Rep); 2007; 1-379; ;Abstract,
Sevcencu, C; A review of electrical stimulation to treat motility dysfunctions in the digestive tract: effects and stimulation patterns; Neuromodulation; 2007; 85-99; 10.
Sevcencu, C; Gastrointestinal mechanisms activated by electrical stimulation to treat motility dysfunctions in the digestive tract: a review; Neuromodulation; 2007; 100-112; 10.
Schreiber, KL, et al.; Evidence for neuromodulation of enteropathogen invasion in the intestinal mucosa; J Neuroimmune Pharmacol; 2007; 329-337; 2.
Sakas, DE, et al.; An introduction to operative neuromodulation and functional neuroprosthetics, the new frontiers of clinical neuroscience and biotechnology; Acta Neurochir Suppl; 2007; 42439; 97;Abstract.
Reitz, A, et al.; Topographic anatomy of a new posterior approach to the pudendal nerve for stimulation; Eur Urol; 2007; 1350-1355; discussion 1355-1356; 51.
Ratto, C, et al.; Sacral neuromodulation in the treatment of defecation disorders; Acta Neurochir Suppl; 2007; 341-350; 97;Abstract.
Pauls, RN, et al.; Effects of sacral neuromodulation on female sexual function; Int Urogynecol J Pelvic Floor Dysfunct; 2007; 391-395; 18.
Melenhorst, J, et al.; Sacral neuromodulation in patients with faecal incontinence results of the first 100 permanent implantations; Colorectal Dis; 2007; 725-730; 9.
Mcachran, SE, et al.; Sacral neuromodulation in the older woman; Clin Obstet Gynecol; 2007; 735-744; 50.
Lewis, JM, et al.; Non-traditional management of the neurogenic bladder: tissue engineering and neuromodulation; ScientificWorldJournal; 2007; 1230-1241; 7.
Leong, FC, et al.; Neuromodulation for the treatment of urinary incontinence; Mo Med; 2007; 435-439; 104;Abstract.
Kuo, HC; Recovery of detrusor function after urethral botulinum A toxin injection in patients with idiopathic low detrusor contractility and voiding dysfunction; Urology; 2007; 57-61; discussion; 61-52; 69.
Kessler, TM, et al.; Sacral neuromodulation for refractory lower urinary tract dysfunction: results of a nationwide registry in Switzerland; Eur Urol; 2007; 1357-1363; 51.
Keppene, V, et al.; [Neuromodulation in the managment of neurogenic lower urinary tract dysfunction]; Prog Urol; 2007; 609-615; 17;Abstract.
Karsenty, G, et al.; Botulinum toxin type a injections into the trigone to treat idiopathic overactive bladder do not induce vesicoureteral reflux; J Urol; 2007; 1011-1014; 177.
Iarumov, N, et al.; [Anal incontinence—new methods of surgical treatment using artificial bowel sphincter and sacral nerve stimulation]; Khirurgiia (Sofiia); 2007; 40-45;;Abstract.
Hoque, T, et al.; Validation of internal controls for gene expression analysis in the intestine of rats infected with Hymenolepis diminuta; Parasitol Int; 2007; 325-329; 56.
Hashim, H, et al.; Novel uses for antidiuresis; Int J Clin Pract Suppl; 2007; 32-36;;Abstract.
Groenendijk, PM, et al.; Five-Year Follow-up After Sacral Neuromodulation: Single Center Experience; Neuromodulation; 2007; 363-368; 10.
Glinski, RW, et al.; Refractory overactive bladder: Beyond oral anticholinergic therapy; Indian J Urol; 2007; 166-173; 23.
Felt-Bersma, RJ, et al.; Temperature-controlled radiofrequency energy (SECCA) to the anal canal for the treatment of faecal incontinence offers moderate improvement; Eur J Gastroenterol Hepatol; 2007; 575-580; 19;Abstract.
Duthie, J, et al.; Botulinum toxin injections for adults with overactive bladder syndrome; Cochrane Database Syst Rev; 2007; Cd005493; ;Abstract,
Dmochowski, R; Neuromodulation and the urinary tract—are we over the rainbow or have we simply stepped through the looking glass?; J Urol; 2007; 1844-1845; 178.
Deffieux, X, et al.; [Voiding dysfunction after surgical resection of deeply infiltrating endometriosis: pathophysiology and management]; Gynecol Obstet Fertil; 2007; S8-13; 35 Suppl 1;Abstract.
Yun, AJ, et al.; Opening the floodgates: benign prostatic hyperplasia may represent another disease in the compendium of ailments causes by the global sympathetic bias that emerges with aging; Med Hyptheses; 2006; 392-394; 67.
Wein, AJ, et al.; Overactive bladder: a better understanding of pathophysiology, diagnosis and management; J Urol; 2006; S5-10; 175.
Van Voskuilen, AC, et al.; Long term results of neuromodulation by sacral nerve stimulation for lower urinary tract symptoms: a retrospective single center study; Eur. Urol; 2006; 366-372; 49.
Van Der Pal, F, et al.; Implant-Driven Tibial Nerve Stimulation in the Treatment of Refractory Overactive Bladder Syndrome: 12-Month Follow-up; Neuromodulation; 2006; 163-171; 9.
Van Der Pal, F, et al.; Current opinion on the working mechanisms of neuromodulation in the treatment of lower urinary tract dysfunction; Curr Opin Urol; 2006; 261-267; 16.

(56) References Cited

OTHER PUBLICATIONS

Van Balken, MR, et al.; Prognostic factors for successful percutaneous tibial nerve stimulation; Eur Urol; 2006; 360-365; 49.
Van Balken, MR, et al.; Sexual functioning in patients with lower urinary tract dysfunction improves after percutaneous tibial nerve stimulation; Int J Impot Res; 2006; 470-475; discussion 476; 18.
Uludag, O, et al.; Sacral neuromodulation; does it affect colonic transit time in patients with faecal incontinence?; Colorectal Dis; 2006; 318-322; 8.
Sherman, ND, et al.; The current use of neuromodulation for bladder dysfunction; Minerva Ginecol; 2006; 283-293; 58;Abstract.
Seif, C, et al.; [Use of permanent electrodes in the peripheral nerve evaluation test (PNE-Test) in comparison to conventional wire electrodes]; Aktuelle Urol; 2006; 277-280; 37;Abstract.
Pelliccioni, G, et al.; External anal sphincter responses after S3 spinal root surface electrical stimulation; Neurourol Urodyn; 2006; 788-791; 25.
Nyarangi-Dix, JN, et al.; [Overactive bladder syndrome. Are there indications for surgical therapy?]; Urologe A; 2006; 1289-1290; 1292; 45.
Nordling, J; Surgical treatment of painful bladder syndrome/interstitial cystitis; Womens Health (Lond Engl); 2006; 233-238; 2.
Ng, CK, et al.; Refractory overactive bladder in men: update on novel therapies; Curr Urol Rep; 2006; 456-461; 7.
Michelsen, HB, et al.; Rectal volume tolerability and anal pressures in patients with fecal incontinence treated with sacral nerve stimulation; Dis Colon Rectum; 2006; 1039-1044; 49.
Lazzeri, M, et al.; The challenge of overactive bladder therapy: alternative to antibuscarinic agents; Int Braz J Urol; 2006; 620-630; 32.
Krivoborodov, GG, et al.; [Tibial neuromodulation in the treatment of neurogenic detrusor hyperactivity in patients with Parkinson's disease]; Urologiia; 2006; 42435;;Abstract.
Kenefick, NJ; Sacral nerve neuromodulation for the treatment of lower bowel motility disorders; Ann R Coll Surg Engl; 2006; 617-623; 88.
Humphreys, MR, et al.; Preliminary results of sacral neuromodulation in 23 children; J Urol; 2006; 2227-2231; 176.
Hoch, M, et al.; [Chemical destruction of sacral nerve roots by alcohol injection for the treatment of overactive bladder]; Prog Urol; 2006; 584-587; 16;Abstract.
Hijaz, A, et al.; Complications and troubleshooting of two-stage sacral neuromodulation therapy; a single-institution experience; Urology; 2006; 533-537; 68.
Guys, JM, et al.; [Neurogenic bladder in children: basic principles in diagnosis and treatment]; Ann Urol (Paris); 2006; 15-27; 40;Abstract.
Groen, J, et al.; Sacral neuromodulation women with idiopathic detrusor overactivity incontinence: decreased overactivity but unchanged bladder contraction strength and urethral resistance during voiding; J Urol; 2006; 1005-1009; discussion.
Elkelini, MS, et al.; Safety of MRI at 1.5Tesla in patients with implanted sacral nerve neurostimulator; Eur Urol; 2006; 311-316; 50.
Daneshgari, F; Application for neuromodulation of the lower urinary tract in female urology; Int Braz J Urol; 2006; 262-272; 32.
Corcos, J, et al.; Candian Urological Association guidelines on urinary incontinence; Can J Urol; 2006; 3127-3138; 13;Abstract.
Blok, BF, et al.; Different brain effects during chronic and acute sacral neuromodulation in urge incontinent patients with implanted neurostimulators; BJU Int; 2006; 1238-1243; 98.
Atiemo, HO, et al.; Evaluation and management of refractory overactive bladder; Curr Urol Rep; 2006; 370-375; 7.
Walter, S; [Duloxetine. A new preparation for patients with urinary incontinence]; Ugeskr Laeger; 2005; 4553-4555; 167;Abstract.
Vignes, JR, et al.; Sacral neuromodulation in lower urinary tract dysfunction; Adv Tech Stand Neurosurg; 2005; 177-224; 30;Abstract.
Spinelli, M, et al.; A new minimally invasive procedure for pudendal nerve stimulation to treat neurogenic bladder: description of the method and preliminary data; Neurourol Urodyn; 2005; 305-309; 24.

Sievert, KD; Neuromodulation; Neurourol Urodyn; 2005; 310; 24.
Sherman, ND, et al.; Sacral neuromodulation for the treatment of refractory urinary urge incontinence after stress incontinence surgery; Am J Obstet Gynecol; 2005; 2083-2087; 193.
Seif, C, et al.; [Pudendal nerve stimulation therapy of the overactive bladder—an alternative to sacral neuromodulation?]; Aktuelle Urol; 2005; 234-238; 36;Abstract.
Riazimand, SH, et al.; Interaction between neurotransmitter antagonists and effect of sacral neuromodulation in rats with chronically hyperactive bladder; BJU Int; 2005; 900-908; 96.
Park, SH, et al.; Overactive bladder: treatment options for the aging woman; Int J Fertil Womens Med; 2005; 37-44; 50;Abstract.
Olujide, LO, et al.; Female voiding dysfunction; Best Pract Res Clin Obstet Gynaecol; 2005; 807-828; 19.
Minardi, D, et al.; Lower urinary tract and bowel disorders and multiple sclerosis: role of sacral neuromodulation: a preliminary report; Neuromodulation; 2005; 176-181; 8.
Miller, JJ, et al.; Diagnosis and treatment of overactive bladder; Minerva Ginecol; 2005; 501-520; 57;Abstract.
Mazo, EB, et al.; [The role of somatosensory evoked potentials in prognosis of efficacy of tibial neuromodulation in patients with hyperactive urinary bladder]; Urologiia; 2005; 49-52; ;Abstract.
Leng, WW, et al.; How sacral nerve stimulation neuromodulation works; Urol Clin North Am; 2005; 42692; 32.
Leclers, F, et al.; [Cystomanometric study of bladder sensation during sacral neuromodulation test]; Prog Urol; 2005; 238-243; 15;Abstract.
Kocjancic, E, et al.; Sacral neuromodulation for urinary retention in a kidney-transplant patient; Urol Int; 2005; 187-188; 75.
Kessler, TM, et al.; Prolonged sacral neuromodulation testing using permanent leads: a more reliable patient selection method?; Eur Urol. 2005; 660-665; 47.
Kavia, R, et al.; Overactive bladder; J R Soc Promot Health; 2005; 176-179; 125;Abstract.
Karsenty, G, et al.; Understanding detrusor sphincter dyssynergia—significance of chronology; Urology; 2005; 763-768; 66.
Karademir, K, et al.; A peripheral neuromodulation technique for curing detrusor overactivity: Stoller afferent neurostimulation; Scand J Urol Nephrol; 2005; 230-233; 39.
Kapoor, DS, et al.; Combined urinary and faecal incontinence; Int Urogynecol J Pelvic Floor Dysfunct; 2005; 321-328; 16.
Johnston, TE, et al.; Implantable FES system for upright mobility and bladder and bowel function for individuals with spinal cord injury; Spinal Cord; 2005; 713-723; 43.
Jarrett, ME; Neuromodulation for constipation and fecal incontinence, Urol Clin North Am; 2005; 79-87; 32.
Groen, J, et al.; Chronic pudendal nerve neuromodulation in women with idiopathic refractory detrusor overactivity incontinence: results of a pilot study with a novel minimally invasive implantable mins-stimulator; Neurourol Urodyn; 2005; 226-230; 24.
Freeman, RM, et al.; Overactive bladder; Best Pract Res Clin Obstet Gynaecol; 2005; 829-841; 19.
Everaert, K, et al.; Sacral nerve stimulation for pelvic floor and bladder dysfunction in adults and children; Neuromodulation; 2005; 186-187; 8.
Dasgupta, R, et al.; Changes brain activity following sacral neuromodulation for urinary retention; J Urol; 2005; 2268-2272; 174.
Daneshgari, F, et al.; Future directions in pelvic neuromodulation; Urol Clin North Am; 2005; 113-115, viii; 32.
Craggs, MD; Objective measurement of bladder sensation: use of a new patient-activated device and response to neuromodulation; BJU Int; 2005; 29-36; 96 Suppl 1.
Bernstein, AJ, et al.; Expanding indications for neuromodulation; Urol Clin North Am; 2005; 59-63; 32.
Benson, JT, et al.; Pudendal neuralgia, a severe pain syndrome; Am J Obstet Gynecol; 2005; 1663-1668; 192.
Badawi, JK, et al.; [Current diagnosis and therapy of the overactive bladder and urge incontinence]; Dtsch Med Wochenschr; 2005; 1503-1506; 130;Abstract.
Amundsen, CL, et al.; Sacral neuromodulation for intractable urge incontinence: are there factors associated with cure?; Urology; 2005; 746-750; 66.

(56) References Cited

OTHER PUBLICATIONS

Amoroso, L, et al.; Sacral-neuromodulation CT-guided; Radiol Med; 2005; 421-429; 109;Abstract.
Van Balken, MR, et al.; The use of electrical devices for the treatment of bladder dysfunction: a review of methods; J Urol; 2004; 846-851; 172.
Uludag, O, et al.; Sacral neuromodulation in patients with fecal incontinence: a single-center study; Dis Colon Rectum; 2004; 1350-1357; 47.
Svensson, L, et al.; Neuromodulation of experimental Shigella infection reduces damage to the gut mucosa; Microbes Infect; 2004; 256-264; 6.
Silveri, M, et al.; Voiding dysfunction in x-linked adrenoleukodystrophy: symptom score and urodynamic findings; J Urol; 2004; 2651-2653; 171.
Seif, C, et al.; Finding with Bilateral Sacral Neurostimulation: Sixty-two PNE-Tests in Patients with Neurogenic and Idiopathic Bladder Dysfunctions; Neuromodulation; 2004; 141-145; 7.
Roupret, M, et al.; Sacral neuromodulation for refractory detrusor overactivity in women with an artificial urinary sphincter; J Urol; 2004; 236-239; 172.
Riazimand, SH, et al.; A rat model for studying effects of sacral neuromodulation on the contractile activity of a chronically inflamed bladder; BJU Int; 2004; 158-163; 94.
Pelaez, E, et al.; [Epidural spinal cord stimulation for interstitial cystitis]; Rev Esp Anestesiol Reanim; 2004; 549-552; 51;Abstract.
Qzyalcin, NS, et al.; [Sacral nerve stimulation in fecal incontinence; efficacy and safety]; Agri; 2004; 35-44; 16;Abstract.
Nijman, RJ; Role of antimuscarinics in the treatment of non-neurogenic daytime urinary incontinence in children; Urology; 2004; 45-50; 63.
Madersbacher, H; Overactive bladder—a practical approach to evaluation and management; J Med Liban; 2004; 220-226; 52;Abstract.
Krames, E, et al.; Spinal cord stimulation reverses pain and diarrheal episodes of irritable bowel syndrome: a case report; Neuromodulation; 2004; 82-88; 7.
Kessler, TM, et al.; [Urodynamic phenomena in the aging bladder]; Urologe A; 2004; 542-546; 43.
Hashim H, et al.; Drug treatment of overactive bladder: efficacy, cost and quality-of-life considerations; Drugs; 2004; 1643-1656; 64.
Guys, JM, et al.; Sacral neuromodulation for neurogenic bladder dysfunction in children; J Urol; 2004; 1673-1676; 172.
Gonzalez-Chamorro, F, et al.; [Neurostimulation and neuromodulation in urinary incontinence]; Rev Med Univ Navarra; 2004; 75-84; 48;Abstract.
Fowler, CJ; The perspective of a neurologist on treatment-related research in fecal and urinary incontinence; Gastroenterology; 2004; S172-174; 126.
Fall, M, et al.; EAU guidelines on chronic pelvic pain; Eur Urol; 2004; 681-689; 46.
De Gennaro, M, et al.; Percutaneous tibial nerve neuromodulation is well tolerated in children and effective for treating refractory vesical dysfunction; J Urol; 2004; 1911-1913; 171.
Bower, WF, et al.; A review of non-invasive electro neuromodulation as an intervention for non-neurogenic bladder dysfunction in children; Neurourol Urodyn; 2004; 63-67; 23.
Abrams, P; The role of neuromodulation in the management of urinary urge incontinence; BJU Int; 2004; 1116; 93.
Wein, AJ; Diagnosis and treatment of the overactive bladder; Urology; 2003; 20-27; 62.
Takahashi, S, et al.; Overactive bladder: magnetic versus electrical stimulations; Curr Opin Obstet Gynecol; 2003; 429-433; 15.
Spinelli, M, et al.; New sacral neuromodulation lead for percutaneous implantation using lical anesthesia: description and first experience; J Urol; 2003; 1905-1907; 170.
Shafik, A, et al.; Percutaneous peripheral neuromodulation in the treatment of fecal incontinence; Eur Surg Res; 2003; 103-107; 35.
Seif, C, et al.; Improved sacral neuromodulation in the treatment of the hyperactive detrusor: signal modification in an animal model; BJU Int; 2003; 711-715; 91.
Schurch, B, et al.; Electrophysiological recordings during the peripheral nerve evaluation (PNE) test in complete spinal cord injury patients; World J Urol; 2003; 319-322; 20.
Schonberger, B; [Bladder dysfunction and surgery in the small pelvis. Therapeutic possibilities]; Urologe A; 2003; 1569-1575; 42.
Scheepens, WA, et al.; Urodynamic results of sacral neuromodulation correlate with subjective improvement in patients with an overactive bladder; Eur Urol; 2003; 282-287; 43.
Ruffion, A, et al.; [Two indications for bilateral neuromodulation]; Prog Urol; 2003; 1394-1396; 13;Abstract.
Ruffion, A, et al.; [Sacral root neuromodulation for the treatment of urinary incontinence reported to detrusor hyperactivity]; Neurochirurgie; 2003; 377-382; 49;Abstract.
Romero Maroto, J, et al.; [Techniques and current practice of urodynamics. Problems and traps]; Actas Urol Esp; 2003; 75-91; 27;Abstract.
Ratto, C, et al.; Minimally invasive sacral neuromodulation implant technique: modifications to the conventional procedure; Dis Colon Rectum; 2003; 414-417; 46.
Pannek, J, et al.; [Initial results of Stoller peripheral neuromodulation in disorders of bladder function]; Urologe A; 2003; 1470-1476; 42.
Oliver, S, et al.; Measuring the sensations of urge and bladder during cystometry in urge incontinence and the effects of neuromodulation; Neurourol Urodyn; 2003; 42567; 22.
Martin Braun, P, et al.; [Continuous bilateral sacral neuromodulation as a minimally invasive implantation technique in patients with functional bladder changes]; Arch Esp Urol; 2003; 497-501; 56.
Julius, F, et al.; Catheter tip granuloma associated with sacral region intrathecal drug administration; Neuromodulation; 2003; 225-228; 6.
Hassouna, M, et al.; Update on sacral neuromodulation: indications and outcomes; Curr Urol Rep; 2003; 391-398; 4.
Green, BT, et al.; Neuromodulation of enteropathogen internalization in Peyer's patches from porcine jejunum; J Neuroimmunol; 2003; 74-82; 141.
Fraser, MO, et al.; Neural control of the urethra and development of pharmacotherapy for stress urinary incontinence; BJU Int; 2003; 743-748; 91.
Fjorback, MV, et al.; A portable device for experimental treatment of neurogenic detrusor overactivity; Neuromodulation; 2003; 158-165; 6.
Feler, CA, et al.; Sacral neuromodulation for chronic pain conditions; Anesthesiol Clin North America; 2003; 785-795; 21.
Dasgupta, R, et al.; The management of female voiding dysfunction: Fowler's syndrome—a contemporary update; Curr Opin Urol; 2003; 293-299; 13.
Comiter, CV; Sacral neuromodulation for the symptomatic treatment of refractory interstitial cystitis: a prospective study; J Urol; 2003; 1369-1373; 169.
Bross, S, et al.; [Sacral neuromodulation in patients with nonobstructive, chronic urinary retention: relevance of the carbachol test and influence of associated nerve lession]; Aktuelle Urol; 2003; 157-161; 34;Abstract.
Bross, S, et al.; The role of the carbachol test and concomitant diseases in patients with nonobstructive urinary retention undergoing sacral neuromodulation; World J Urol; 2003; 346-349; 20.
Brooks, DR, et al.; The Caenorhabditis elegans orthologue of mammalian puromycin-sensitive aminopeptidase has roles in embryogenesis and reproduction; J Biol Chem; 2003; 42795-42801; 278.
Braun, PM, et al.; Stimulation signal modification in a porcine model for suppression of unstable detrusor contractions; Urology; 2003; 839-844; 61.
Bouchelouche, K, et al.; Recent developments in the management of interstitial cystitis; Curr Opin Urol; 2003; 309-313; 13.
Beneton, C, et al.; [The medical treatment of overactive bladder]; Neurochirurgie; 2003; 369-376; 49;Abstract.
Banyo, T; [The role of electrical neuromodulation in the therapy of chronic lower urinary tract dysfunction]; Ideggyogy Sz; 2003; 68-71; 56;Abstract.

(56) References Cited

OTHER PUBLICATIONS

Bannowsky, A, et al.; [Sacral neuromodulation in treatment of functional disorders of the lower urinary tract. An overview of basic principles, indications, outcomes]; Urologe A; 2003; 1357-1365; 42.
Antolak, SJ, JR.; Re: Sacral neuromodulation for the symptomatic treatment of refractory interstitial cystitis: a prospective study; J Urol; 2003; 1956; author reply 1956; 170.
Amarenco, G, et al.; Urodynamic effect of acute transcutaneous posterior tibial nerve stimulation in overactive bladder; J Urol; 2003; 2210-2215; 169.
Abrams, P, et al.; The role of neuromodulation in the management of urinary urge incontinence; BJU Int; 2003; 355-359; 91.
Zhou, Y, et al.; Change of vanilloid receptor 1 following neuromodulation in rats with spinal cord injury; J Surg Res; 2002; 140-144; 107.
Yamanouchi, M, et al.; Integrative control of rectoanal reflex in guinea pigs through lumbar colonic nerves; Am J Physiol Gastrointest Liver Physiol; 2002; G148-156; 283.
Whitemore, KE; Complementary and alternative therapies as treatment approaches for interstitial cystitis; Rev Urol; 2002; S28-35; 4 Suppl 1.
Van Kerrebroeck, PE; Neuromodulation and other electrostimulatory techniques; Scand J Urol Nephrol Suppl; 2002; 82-86.
Uranga, A, et al.; An integrated implantable electrical sacral root stimulator for bladder control; Neuromodulation; 2002; 238-247; 5.
Uludag, O, et al.; [Sacral neuromodulation is effective in the treatment of fecal incontinence with intact sphincter muscles; a prospective study]; Ned Tijdschr Geneeskd; 2022; 989-993; 146;Abstract.
Swinn, MJ, et al.; The cause and natural history of isolated urinary retention in yound women; J Urol; 2002; 151-156; 167.
Scheepens, WA, et al.; Predictive factors for sacral neuromodulation in chronic lower urinary tract dysfunction; Urology; 2002; 598-602; 60.
Scheepens, WA, et al.; Unilateral versus bilateral sacral neuromodulation in patients with chronic voiding dysfunction; J Urol; 2002; 2046-2050; 168.
Ripetti, V, et al.; Sacral nerve neuromodulation improves physical, psychologica and social quality of life in patients with fecal incontinence; Tech Coloproctol; 2002; 147-152; 6.
Ramundo, JM, et al.; State of the science: pathology and management of the patient with overactive bladder; Ostomy Wound Manage; 2002; 22-27; 48.
Pettit, PD, et al.; Sacral neuromodulation: new applications in the treatment of female pelvic floor dysfunction; Curr Opin Obstet Gynecol; 2002; 521-525; 14.
Ordia, JI, et al.; Continuous intrathecal baclofen infusion delivered by a programmable pump for the treatment of severe spasticity following traumatic brain injury; Neuromodulation; 2002; 103-107; 5.
Mazo, EB, et al.; [Temporary sacral and tibial neuromodulation in treating patients with overactive urinary bladder]; Zh Vopr Neirokhir Im N N Burdenko; 2002; 17-21; Abstract.
Malouf, AJ, et al.; Short-term effects of sacral nerve stimulation for idiopathic slow transit constipation; World J Surg; 2002; 166-170; 26.
Malossi, J, et al.; Sacral neuromodulation for the treatment of bladder dysfunction; Curr Urol Rep; 2002; 61-66; 3.
Linares Quevedo, AI, et al.; [Posterior sacral root neuromodulation in the treatment of chronic urinary dysfunction]; Actas Urol Esp; 2002; 250-260; 26;Abstract.
Krivoborodov, GG, et al.; [Afferent stimulation of the tibial nerve in patients with hyperactive bladder]; Urologiia, 2002; 36-39; ;Abstract.
Kohli, N, et al.; Neuromodulation techniques for the treatment of the overactive bladder; Clin Obstet Gynecol; 2002; 218-232; 45.
Kirkham, AP, et al; neuromodulation through sacral nerve roots 2 to 4 with a Finetech-Brindley sacral posterior and anterior root stimulator; Spinal Cord; 2002; 272-281; 40.
Jezernik, S, et al.; Electrical stimulation for the treatment of bladder dysfunction: current status and future possibilities; Neurol Res; 2002; 413-430; 24;Abstract.
Hedlund, H, et al.; Sacral neuromodulation in Norway: clinical experience of the first three years; Scand J Urol Nephrol Suppl; 2002; 87-95; ;Abstract.
Ferulano, GP, et al.; [Sacral neuromodulation in fecal continence disorders]; Recenti Prog Med; 2002; 403-409; 93;Abstract.
Braun, PM, et al.; [Chronic sacral bilateral neuromodulation. Using a minimal invasive implantation technique in patients with disorders of bladder function]; Urologe A; 2002; 44-47; 41.
Braun, PM, et al.; Alterations of cortical electrical activity in patients with sacral neuromodulation; Eur Urol; 2002; 562-566; discussion 566-567; 41.
Amundsen, CL, et al.; Sacral neuromodulation in an older, urge-incontinent population; Am J Obstet Gynecol; 2002; 1462-1465; discussion 1465; 187.
Wyndaele, JJ, et al.; Conservative treatment of the neuropathic bladder in spinal cord injured patients; Spinal Cord; 2001; 294-300; 39.
Walsh, IK, et al.; Non-invasive antidromic neurostimulation: a simple effective method for improving bladder storage; Neurourol Urodyn; 2001; 73-84; 20.
Scheepens, WA, et al.; [Neuromodulation and neurostimulation in urology]; Ned Tijdschr Geneeskd; 2001; 1730-1734; 145;Abstract.
Mauroy, B, et al.; [Long-term results of interferential current stimulation in the treatment of bladder instability]; Prog Urol; 2001; 34-39; 11; Abstract.
Maher, CF, et al.; Percutaneous sacral nerve root neuromodulation for intractable interstitial cystitis; J Urol; 2001; 884-886; 165.
Krolczyk, G, et al.; Effects of continuous microchip (MC) vagal neuromodulation on gastrointestinal function in rats; J Physiol Pharmacol; 2001; 705-715; 52.
Kirkham, AP, et al.; The acute effects of continuous and conditional neuromodulation on the bladder in spinal cord injury; Spinal Cord; 2001; 420-428; 39.
Jarvis, JC, et al.; Functional electrical stimulation for control of internal organ function; Neuromodulation; 2001; 155-164; 4.
Hohenfellner, M, et al.; Chronic sacral neuromodulation for treatment of neurogenic bladder dysfunction: long-term results with unilateral implants; Urology; 2001; 887-892; 58.
Hoebeke, P, et al.; Transcutaneous neuromodulation for the urge syndrome in children: a pilot study; J Urol; 2001; 2416-2419; 166.
Hindley, RG, et al.; The 2-year symptomatic and urodynamic results of a prospective randomized trial of interstitial radiofrequency therapy vs transurethral resection of the prostate; BJU Int; 2001; 217-220; 88.
Groen, J, et al.; Computerized assessment of detrusor instability in patients treated with sacral neuromodulation; J Urol; 2001; 169-173; 165.
Groen, J, et al.; Neuromodulation techniques in the treatment of the overactive bladder; BJU Int; 2001; 723-731; 87.
Govier, FE, et al.; Percutaneous afferent neuromodulation for the refractory overactive bladder: results of a multicenter study; J Urol; 2001; 1193-1198; 165.
Ganio, E, et al.; Neuromodulation for fecal incontinence: outcome in 16 patients with definitive implant. The initial Italian Sacral Neurostimulation Group (GINS) experience; Dis Colon Rectum; 2001; 965-970; 44.
Dorflinger, A, et al.; Voiding dysfunction; Curr Opin Obstet Gynecol; 2001; 507-512; 13.
Carey, M, et al.; Sacral nerve root stimulation for lower urinary tract dysfunction: overcoming the problem of lead migration; BJU Int; 2001; 15-18; 87.
Bugee, M, et al.; An implant for chronic selective stimulation of nerves; Med Eng Phys; 2001; 29-36; 23.
Buback, D; The use of neuromodulation for treatment of urinary incontinence; Aorn J; 2001; 176-178, 181-177, 189-190; uiz 191-176; 76;Abstract.
Bower, WF, et al.; A pilot study of the home application of transcutaneous neuromodulation in children with urgency or urge incontinence; J Urol; 2001; 2420-2422; 166.

(56) References Cited

OTHER PUBLICATIONS

Benson, JT; New therapeutic options for urge incontinence; Curr Womens Health Rep; 2001; 61-66; 1;Abstract.
Alo, KM, et al.; Selective Nerve Root Stimulation (SNRS) for the Treatment of Intractable Pelvic Pain and Motor Dysfunction: A Case Report; Neuromodulation; 2001; 19-23; 4.
Alo, KM, et al.; Sacral nerve root stimulation for the treatment of urge incontinence and detrusor dysfunction utilizing a cephalocaudal intraspinal method of lead insertion: a case report; Neuromodulation; 2001; 53-58; 4.
Wyndaele, JJ, et al.; Influence of sacral neuromodulation on electrosensation of the lower urinary tract; J Urol; 2000; 221-224; 163.
Weil, EH, et al.; Sacral root neuromodulation in the treatment of refractory urinary urge incontinence: a prospective randomized clinical trial; Eur Urol; 2000; 161-171; 37;Abstract.
Wang, Y, et al.; Neuromodulation reduces urinary frequency in rats with hydrochloric acid-induced cystitis; BJU Int; 2000; 726-730; 86.
Wang, Y, et al.; Neuromodulation reduces c-fos gene expression in spinalized rats: a double-blind randomized study; J Urol; 2000; 1966-1970; 163.
Sun, Y, et al.; Effects of neural blocking agents on motor activity and secretion in the proximal and distal rat colon: evidence of marked segmental differences in nicotinic receptor activity; Scand J Gastroenterol; 2000; 380-388; 35.
Shaker, H, et al.; Role of C-afferent fibres in the mechanism of action of sacral nerve root neuromodulation in chronic spinal cord injury; BJU Int; 2000; 905-910; 85.
Rovner, ES; Treatment of urinary incontinence; Curr Urol Rep; 2000; 235-244; 1.
Nijman, RJ; Classification and treatment of functional incontinence in children; BJU Int; 2000; 37-42; discussion 45-36; 85 Suppl 3.
Mazo, EB, et al., [Temporary sacral neuromodulation in patients with urge incontinence]; Urologiia; 2000; 42-46; ;Abstract.
Klingler, HC, et al.; Use of peripheral neuromodulation of the S3 regions for treatment of detrusor overactivity: a urodynamic-based study; Urology; 2000; 766-771; 56.
Hohenfellner, M, et al.; [Sacral neuromodulation of the urinary bladder]; Urologe A; 2000; 55-63; 39.
Hohenfellner, M, et al.; Sacral neuromodulation for treatment of lower urinary tract dysfunction; BJU Int; 2000; 10-19; discussion 22-13; 85 Suppl 3.
Grill, WM; Electrical activation of spinal neural circuits: application to motor-system neural prostheses; Neuromodulation; 2000; 97-106; 3.
Dahms, SE, et al.; Sacral neurostimulation and neuromodulation in urological practice; Curr Opin Urol; 2000; 329-335; 10.
Costa, JA, et al.; Spinal cord neuromodulation for voiding dysfunction; Clin Obstet Gynecol; 2000; 676-688; 43.
Chancellor, MB, et al.; Principles of Sacral Nerve Stimulation (SNS) for the Treatment of Bladder and Urethral Sphincter Dysfunctions; Neuromodulation; 2000; 16-26; 3.
Bosch, JL, et al.; Sacral nerve neuromodulation in the treatment of patients with refractory motor urge incontinence: long-term results of a prospective longitudinal study; J Urol; 2000; 1219-1222; 163.
Bosch, JL; Sacral neuromodulation: treatment success is not just a matter of optimal electrode position; BJU Int; 2000; 20-21; discussion 22-23; 85 Suppl 3.
Van Der Aa, HE, et al.; Sacral anterior root stimuation for bladder control: clinical results; Arch Physiol Biochem; 1999; 248-256; 107.
Vaizey, CJ, et al.; Effects of short term sacral nerve stimulation on anal and rectal function in patients with anal incontinence; Gut; 1999; 407-412; 44.
Sullivan, J, et al.; Overactive detrusor; Curr Opin Urol; 1999; 291-296; 9.
Sullivan, J, et al.; The overactive bladder: neuropharmacological basis of clinical management; Curr Opin Obstet Gynecol; 1999; 477-483; 11.

Shaker, H, et al.; Sacral root neuromodulation in the treatment of various voiding and storage problems; Int Urogynecol J Pelvic Floor Dysfunct; 1999; 336-343; 10;Abstract.
Ishigooka, M, et al.; Sacral nerve stimulation and diurnal urine volume; Eur Urol; 1999; 421-426; 36;Abstract.
Craggs, M, et al.; Neuromodulation of the lower urinary tract; Exp Physiol; 1999; 149-160; 84.
Braun, PM, et al.; Tailored laminectomy: a new techniqu for neuromodulator implantation; J Urol; 1999; 1607-1609; 162.
Bemelmans, BL, et al.; Neuromodulation by implant for treating lower urinary tract symptoms and dysfunction; Eur Urol; 1999; 81-91; 36;Abstract.
Anton, PA; Stress and mind-body impact on the course of inflammatory bowel diseases; Semin Gastrointest Dis; 1999; 14-19; 10;Abstract.
Zvara, P, et al.; An animal model for the neuromodulation of neruogenic bladder dysfunction; Br J Urol; 1998; 267-271; 82.
Wallace, JL, et al.; Lack of beneficial effect of a tachykinin receptor antagonist in experimental colitis; Regul Pept; 1998; 95-101; 73.
Van Kerrebroeck, PE; The role of electrical stimulation in voiding dysfunction; Eur Urol; 1998; 27-30; 34 Suppl 1;Abstract.
Shaker, HS, et al.; Sacral root neuromodulation in idiopathic nonobstructive chronic urinary retention; J Urol; 1998; 1476-1478; 159.
Shaker, HS, et al.; Sacral nerve root neuromodulation: an effective treatment for refractory urge incontinence; J Urol. 1998; 1516-1519; 159.
Schultz-Lampel, D, et al.; Experimental results on mechanisms of action of electrical neuromodulation in chronic urinary retention; World J Urol; 1998; 301-304; 16.
Schmidt, RA, et al.; Neurostimulation and neuromodulation: a guide to selecting the right urologic patient; Eur Urol; 1998; 23-26; 34 Suppl 1;Abstract.
Jiang, CH; Modulation on the micturition reflex pathway by intravesical electrical stimulation: an experimental study in the rat: Neurourol Urodyn; 1998; 543-553; 17.
Hohenfellner, M, et al.; Bilateral chronic sacral neuromodulation for treatment of lower urinary tract dysfunction; J Urol; 1998; 821-824; 160.
Hasan, ST, et al.; Neuromodulation in bladder dysfunction; Curr Opin Obstet Gynecol; 1998; 395-399; 10.
Grunewald, V; Neuromodulation/neurostimulation; World J Urol; 1998; 299-300; 16.
Chapple, CR, et al.; Surgery for detrusor overactivity; World J Urol; 1998; 268-273; 16.
Brown, DR, et al.; Delta-opioid receptor mRNA expression and immunohistochemical localization in porcine ileum; Dig Dis Sci; 1998; 1402-1410 ;43.
Bower, WF, et al.; A urodynamic study of surface neuromodulation versus sham in detrusor instability and sensory urgency; J Urol; 1998; 2133-2136; 160.
Bosch, JL, et al.; Neuromodulation: urodynamic effects of sacral (S3) spinal nerve stimulation in patients with detrusor instability or detrusor hyperflexia; Behav Brain Res; 1998; 141-150; 92.
Bosch, JL; Sacral neuromodulation in the treatment of the unstable bladder; Curr Opin Urol; 1998; 287-291; 8.
Turner, WH, et al.; Smooth muscle of the bladder in the normal and the diseased state: pathophysiology, diagnosis and treatment; Pharmacol Ther; 1997; 77-110; 75.
Sutherland, RS, et al.; Vesicourethral function in mice with genetic disruption of neuronal nitric oxide synthase; J Urol; 1997; 1109-1116; 157.
Gottwald, T, et al., [Sex differences in neuromodulation of mucosal mast cells in the rat jejunum]; Langenbecks Arch Chir. 1997; 157-163; 382;Abstract.
Gonzalez-Chamorro, F, et al.; [Current status of neurostimulation and neuromodulation for vesicourethral dysfunction]; Arch Esp Urol; 1997; 687-694; 50;Abstract.
Everaert, K, et al.; The urodynamic evaluation of neuromodulation in patients with voiding dysfunction; Br J Urol; 1997; 702-707; 79.
Sheriff, MK, et al.; Neuromodulation of detrusor hyper-reflexia by functional magnetic stimulation of the sacral roots; Br J Urol; 1996; 39-49; 78;Abstract.

(56) References Cited

OTHER PUBLICATIONS

Hasan, ST, et al.; Surface localization of sacral foramina for neuromodulation of bladder funtion. An Anatomical study; Eur Urol; 1996; 90-98; 29;Abstract.
Hasan, ST, et al.; Transcutaneous electrical nerve stimulation and temporary S3 neuromodulation in idiopathic detrusor instability; J Urol; 1996; 2005-2011; 155.
Bristow, SE, et al.; TENS: a treatment option for bladder dysfunction; Int Urogynecol J Pelvid Floor Dysfunct; 1996; 185-190; 7.
Traynor, TR, et al.; Neuromodulation of ion transport in porcine distal colon: NPY reduces secretory action of leukotrienes; Am J Physiol; 1995; R426-431; 269;Abstract.
Kinder, MV, et al.; Neuronal circuitry of the lower urinary tract central and peripheral neuronal control of the micturition cycle; Anat Embryol (Berl); 1995; 195-209; 192.
Hassouna, M, et al.; Dog as an animal model for neurostimulation; Neurourol Urodyn; 1994; 159-167; 13.
Duve, H, et al.; Distribution and functional significance of Leu-callatostatins in the blowfly *Calliphora vomitoria*; Cell Tissue Res; 1994; 367-379; 276.
Wiklund, CU et al.; Modulation of cholinergic and substance P-like neurotransmission by nitric oxide in the guinea-pig ileum; Br J Pharmacol; 1993; 833-839; 110.
Tanagho, EA; Concepts of neuromodulation; Neurourol Urodyn; 1993; 487-488; 12.
Katsuragi, T, et al.; Possible transsynaptic cholinergic neuromodulation by ATP released from ileal longitundinal muscles of giunea pigs; Life Sci; 1993; 911-918; 53.
Dijkema, HE, et al.; Neuromodulation of sacral nerves for incontinence and voiding dysfunctions. Clinical results and complications; Eur Urol; 1993; 72-76; 24;Abstract.
Tanagho, EA; Neuromodulation in the management of voiding dysfunction in children; J Urol; 1992; 655-657; 148;Abstract.
Dijkema, HE, et al.; [Initial experiences with neuromodulation as treatment for incontinence and micturition disorders in The Netherlands]; Ned Tijdschr Geneeskd; 1992; 88-90; 136;Abstract.
Collins, SM; Is the irritable gut an inflamed gut?; Scand J Gastroenterol Suppl; 1992; 102-105; 192;Abstract.
Parija, SC, et al.; Adenosine- and alpha,beta-methylene ATP-induced differential inhibition of cholinergic and non-cholinergic neurogenic responses in rat urinary bladder; Br J Pharmacol; 1991; 396-400; 102.
Kachur, JF, et al.; neuromodulation of guinea pig intestinal electrolyte transport by cholecystokinin octapeptide; Gastroenterology; 1991; 344-349; 100;Abstract.
Katsuragi T, et al.; Involvement of dihydropyridine-sensitive Ca2+ channers in adenosine-evoked inhibition of acetylcholine release from guinea pig ileal preparation; J Neurochem; 1990; 363-369; 55.
Burnstock, G; Innervation of bladder and bowel, Ciba Found Symp; 1990; 2-18; discussion 18-26; 151;Abstract.
Wiklund, NP, et al.; Cholinergic neuromodulation by endothein in guinea pig ileum; Neurosci Lett; 1989; 342-346; 101.
Carey, HV, et al.; Neuromodulation of intestinal transport in the sucking mouse; Am J Physiol; 1989; R481-486; 256;Abstract.
Wiklund, NP, et al.; Neuromodulation by adenine nucleotides, as indicated by experiments with inhibtors of nucleotide inactivation; Acta Physiol Scand; 1986; 217-223; 126;Abstract.
Hoyle, CH, et al.; Ethylcholine mustard aziridinium ion (AF64A) impairs cholinergic neuromuscular transmission in the guinea-pig ileum and urinary bladder, and cholinergic neuromodulation in the enteric nervous system of the guinea-pig distal colon; Gen Pharmacol; 1986; 543-548; 17.
Katsuragi, T, et al.; Cholinergic neuromodulation by ATP, adenosince and its N6-substituted analogues in guinea-pig ileum; Clin Exp Pharmacol Physiol; 1985; 73-78; 12;Abstract.
Barroso U Jr et al.; Electrical nerve stimulation for overactive bladder in children;Nature Reviews Urology; 2011; 402-407; 8.
M. Matsushita et al.; Primary somatosensory evoked magnetic fields elicited by sacralsurface electrical stimulation; Neuroscience Letters; 2008; 77?80; 431.
N. Patidar et al.; Transcutaneous posterior tibial nerve stimulation in pediatric overactivebladder: A preliminary report; Journal of Pediatric Urology; 2015; 351.e1-351.e6; 11.
Perissinotto et al.; Transcutaneous Tibial Nerve Stimulation in the Treatment of Lower UrinaryTract Symptoms and Its Impact on Health-Related Quality of Life in Patients With ParkinsonDisease; J Wound, Ostomy and Continence Nurses Society; 2015; 94-99; 42.
Tomonori Yamanishi et al.; Neuromodulation for the Treatment of Lower Urinary TractSymptoms; Low Urin Tract Symptoms; 2015; 121-132; 7.
Christopher J. Chermansky et al., "MP68-15 Electrical Stimulation of Afferent Nerves in the Foot NITH Transcutaneous Adhesive Pad Electrodes Improves Overactive Bladder Symptoms in Women", The Journal of Urology, vol. 195, No. 4S, Supplement, Monday, May 9, 2016, 2 pages.
Christopher J. Chermansky, "Foot/Hand Neuromodulation for Overactive Bladder (OAB) (FootStim)"; First Posted: Oct. 30, 2013; http://clinicaltrials.govict2/show/NCT01972061; pp. 1-5.
Tai et al., "FootStim: Neuromodulation therapy for overactive bladder"; http://www.engineering.pitt.edu/Sub-Sites/Programs/Coulter/Projects/2013---FootStim/: retrieved on Sep. 26, 2017.
Oliver_et_al—2003—Neurourology_and_Urodynamics.
J. Groen and J.L.H.R. Bosch; Neuromodulation techniques in the treatment of the overactive bladder; BJU International (2001), 87, 723-731.
Michael Craggs and Jonathon McFarlane; Neuromodulation of the lower urinary tract; Experimental Physiology (1999), 84, 149-160.
Yogi A. Patel; Kilohertz Electrical Stimulation Nerve Conduction Block: Effects of Electrode Surface Area; IEEE Transactions on Neural Systems and Rehabilitation Engineering, vol. 25, No. 10, Oct. 2017.

\* cited by examiner

Action Potential in a Neuron

TOPICAL NERVE STIMULATOR AND SENSOR FOR BLADDER CONTROL

RELATED APPLICATIONS AND CLAIM OF PRIORITY

This application claims priority to and the benefit of the filing date of United States provisional patent application Ser. No. 62/119,134 filed Feb. 21, 2015. This application also claims priority to and the benefit of the filing date as a continuation-in-part application of U.S. utility patent application Ser. No. 14/893,946 filed Nov. 25, 2015, which claims priority to and the benefit of the filing date as a national stage application of PCT patent application serial no. PCT/US14/40240, filed May 30, 2014, which in turn claims priority to U.S. provisional patent application Ser. No. 61/828,981, filed May 30, 2013.

TECHNICAL PROBLEM

Mammalian and human nerves control organs and muscles. Artificially stimulating the nerves elicits desired organ and muscle responses. Accessing the nerves to selectively control these responses from outside the body, without invasive implants or needles penetrating the dermis, muscle or fat tissue is desired.

A Topical Nerve Stimulator and Sensor (TNSS) device described in the related U.S. Patent Application Serial No. PCT/US 14/40240 filed May 30, 2014 is used to stimulate nerves. A TNSS may apply electrode generated electric field(s) in a low frequency to dermis in the proximity of a nerve. The TNSS also includes hardware and logic for high frequency (GHz) communication to mobile devices.

A wireless system including a TNSS device is described herein. Its components, features and performance characteristics are set forth in the following technical description. Advantages of a wireless TNSS system over existing transcutaneous electrical nerve stimulation devices are:

fine control of all stimulation parameters from a remote device such as a smartphone, either directly by the user or by stored programs;

multiple electrodes of a TNSS can form an array to shape an electric field in the tissues;

multiple TNSS devices can form an array to shape an electric field in the tissues;

multiple TNSS devices can stimulate multiple structures, coordinated by a smartphone;

selective stimulation of nerves and other structures at different locations and depths in a volume of tissue;

mechanical, acoustic or optical stimulation in addition to electrical stimulation;

transmitting antenna of TNSS device can focus beam of electromagnetic energy within tissues in short bursts to activate nerves directly without implanted devices;

inclusion of multiple sensors of multiple modalities, including but not limited to position, orientation, force, distance, acceleration, pressure, temperature, voltage, light and other electromagnetic radiation, sound, ions or chemical compounds, making it possible to sense electrical activities of muscles (EMG, EKG), mechanical effects of muscle contraction, chemical composition of body fluids, location or dimensions or shape of an organ or tissue by transmission and receiving of ultrasound;

TNSS devices are expected to have service lifetimes of days to weeks and their disposability places less demand on power sources and battery requirements;

combination of stimulation with feedback from artificial or natural sensors for closed loop control of muscle contraction and force, position or orientation of parts of the body, pressure within organs, and concentrations of ions and chemical compounds in the tissues;

multiple TNSS devices can form a network with each other, with remote controllers, with other devices, with the internet and with other users;

collection of large amounts of data from one or many TNSS devices and one or many users regarding sensing and stimulation, collected and stored locally or through the internet;

analysis of large amounts of data to detect patterns of sensing and stimulation, apply machine learning, and improve algorithms and functions;

creation of databases and knowledge bases of value;
convenience;
absence of wires to become entangled in clothing
showerproof and sweat proof
low profile, flexible, camouflaged or skin colored
integrated power, communications, sensing and stimulating
inexpensive
disposable TNSS, consumable electronics power management that utilizes both hardware and software functions will be critical to the convenience factor and widespread deployment of TNSS device.

DESCRIPTION OF ACTION POTENTIALS AND NERVE PHYSIOLOGY

Figure 1:
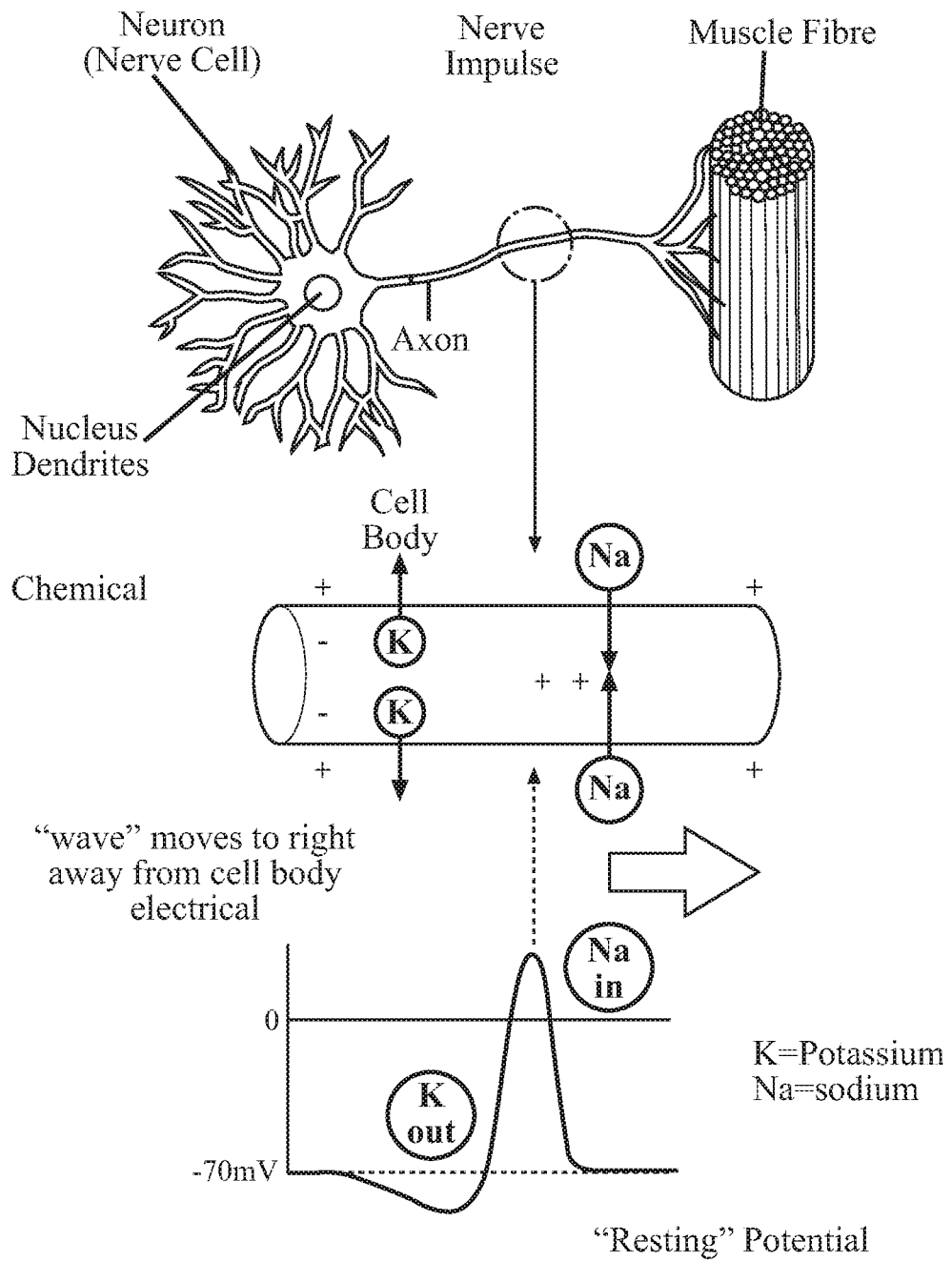
FIG. 1 is a depiction of a neuron activating a muscle by electrical impulse.

Referring to FIG. 1, a nerve cell normally has a voltage across the cell membrane of 70 millivolts with the interior of the cell at a negative voltage with respect to the exterior of the cell. This is known as the resting potential and it is normally maintained by metabolic reactions which maintain different concentrations of electrical ions in the inside of the cell compared to the outside. Ions can be actively "pumped" across the cell membrane through ion channels in the membrane that are selective for different types of ion, such as sodium and potassium. The channels are voltage sensitive and can be opened or closed depending on the voltage across the membrane. An electric field produced within the tissues by a stimulator can change the normal resting voltage across the membrane, either increasing or decreasing the voltage from its resting voltage.

Figure 2:
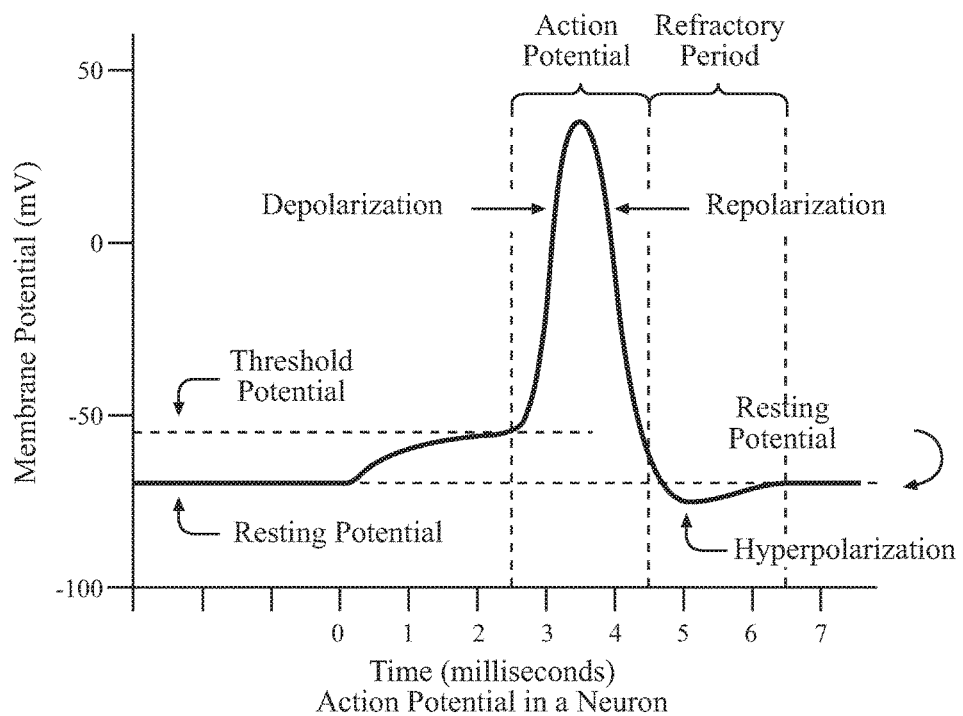
FIG. 2 is a representation of the electrical potential activation time of an electrical impulse in a nerve.

Referring to FIG. 2, a decrease in voltage across the cell membrane to about 55 millivolts opens certain ion channels, allowing ions to flow through the membrane in a self-catalyzing but self-limited process which results in a transient decrease of the trans membrane potential to zero, and even positive, known as depolarization followed by a rapid restoration of the resting potential as a result of active pumping of ions across the membrane to restore the resting situation which is known as repolarization. This transient change of voltage is known as an action potential and it typically spreads over the entire surface of the cell. If the shape of the cell is such that it has a long extension known as an axon, the action potential spreads along the length of the axon. Axons that have insulating myelin sheaths propagate action potentials at much higher speeds than those axons without myelin sheaths or with damaged myelin sheaths.

If the action potential reaches a junction, known as a synapse, with another nerve cell, the transient change in membrane voltage results in the release of chemicals known as neuro-transmitters that can initiate an action potential in the other cell. This provides a means of rapid electrical communication between cells, analogous to passing a digital pulse from one cell to another.

If the action potential reaches a synapse with a muscle cell it can initiate an action potential that spreads over the surface of the muscle cell. This voltage change across the membrane of the muscle cell opens ion channels in the membrane that allow ions such as sodium, potassium and calcium to flow across the membrane, and can result in contraction of the muscle cell.

Increasing the voltage across the membrane of a cell below −70 millivolts is known as hyper-polarization and reduces the probability of an action potential being generated in the cell. This can be useful for reducing nerve activity and thereby reducing unwanted symptoms such as pain and spasticity The voltage across the membrane of a cell can be changed by creating an electric field in the tissues with a stimulator. It is important to note that action potentials are created within the mammalian nervous system by the brain, the sensory nervous system or other internal means. These action potentials travel along the body's nerve "highways". The TNSS creates an action potential through an externally applied electric field from outside the body. This is very different than how action potentials are naturally created within the body.

Electric Fields that can Cause Action Potentials

Referring to FIG. 2, electric fields capable of causing action potentials can be generated by electronic stimulators connected to electrodes that are implanted surgically in close proximity to the target nerves. To avoid the many issues associated with implanted devices, it is desirable to generate the required electric fields by electronic devices located on the surface of the skin. Such devices typically use square wave pulse trains of the form shown in FIG. 3. Such devices may be used instead of implants and/or with implants such as reflectors, conductors, refractors, or markers for tagging target nerves and the like, so as to shape electric fields to enhance nerve targeting and/or selectivity.

Figure 3:
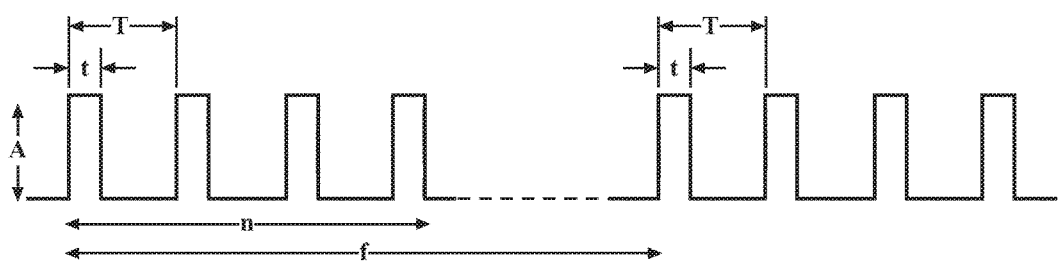
FIG. 3 is a graph showing pulses applied to the skin.
Figure 4:
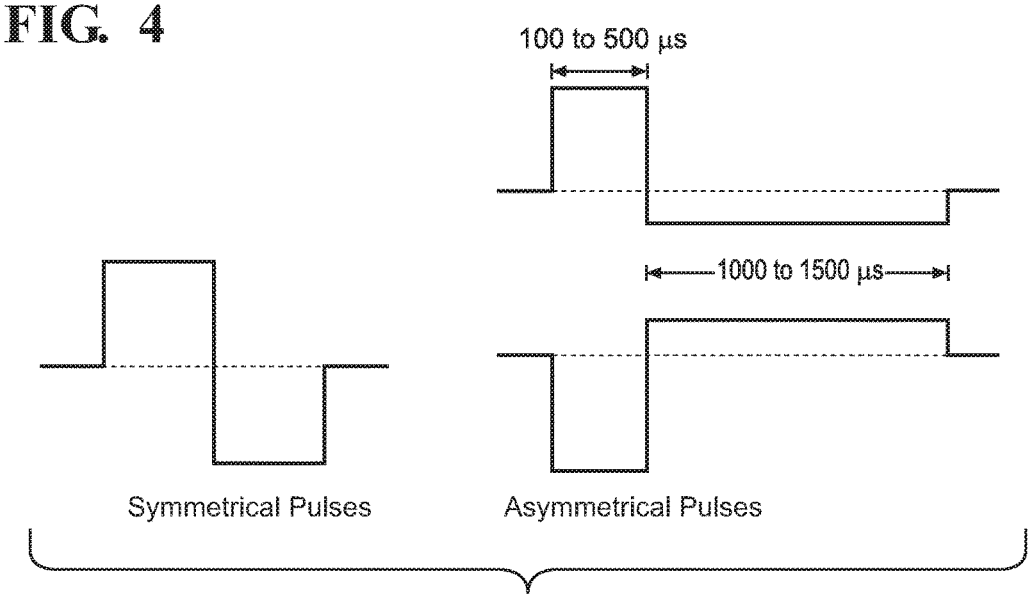
FIG. 4 is a graph showing symmetrical and asymmetrical pulses applied to the skin.

Referring to FIG. 3, the amplitude of the pulses, A, applied to the skin, may vary between 1 and 100 Volts, pulse width, t, between 100 microseconds and 10 milliseconds, duty cycle (t/T) between 0.1% and 50%, the frequency of the pulses within a group between 1 and 100/sec, and the number of pulses per group, n, between 1 and several hundred. Typically, pulses applied to the skin will have an amplitude of up to 60 volts, a pulse width of 250 microseconds and a frequency of 20 per second, resulting in a duty cycle of 0.5%. In some cases balanced-charge biphasic pulses will be used to avoid net current flow. Referring to FIG. 4, these pulses may be symmetrical, with the shape of the first part of the pulse similar to that of the second part of the pulse, or asymmetrical, in which the second part of the pulse has lower amplitude and a longer pulse width in order to avoid canceling the stimulatory effect of the first part of the pulse.

Formation of Electric Fields by Stimulators

The location and magnitude of the electric potential applied to the tissues by electrodes provides a method of shaping the electrical field. For example, applying two electrodes to the skin, one at a positive electrical potential with respect to the other, can produce a field in the underlying tissues such as that shown in the cross-sectional diagram, FIG. 5.

Figure 5:
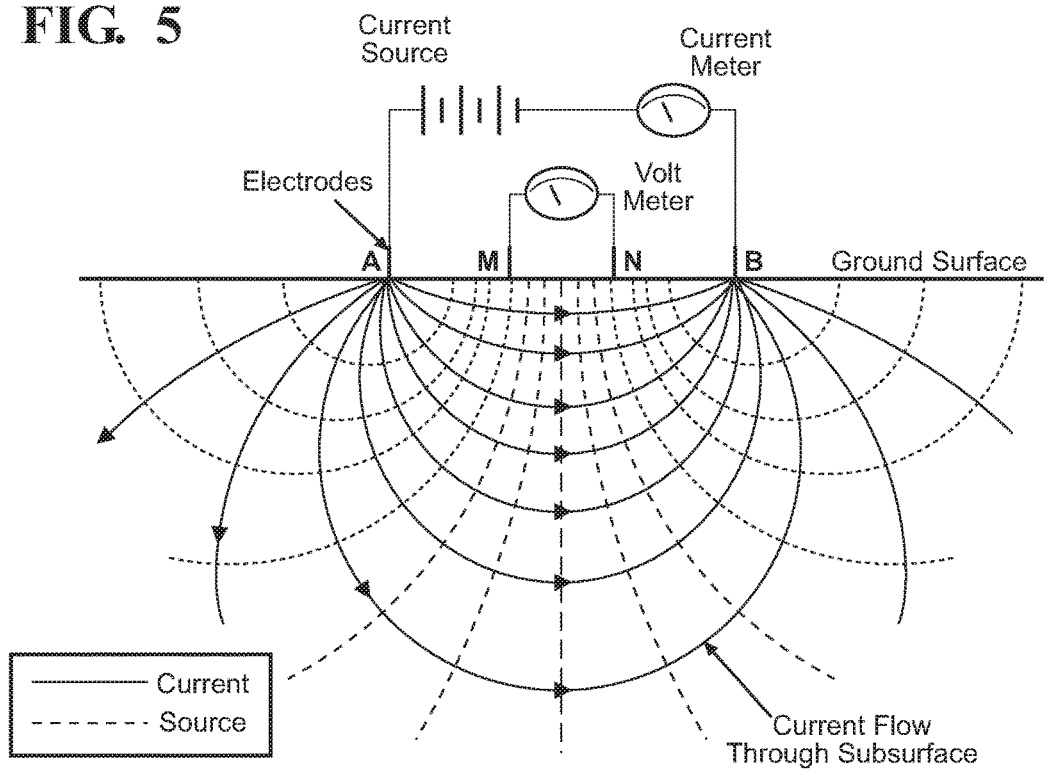
FIG. 5 is a cross-sectional diagram showing a field in underlying tissue produced by application of two electrodes to the skin.

The diagram in FIG. 5 assumes homogeneous tissue. The voltage gradient is highest close to the electrodes and lower at a distance from the electrodes. Nerves are more likely to be activated close to the electrodes than at a distance. For a given voltage gradient, nerves of large diameter are more likely to be activated than nerves of smaller diameter. Nerves whose long axis is aligned with the voltage gradient are more likely to be activated than nerves whose long axis is at right angles to the voltage gradient.

Figure 6:
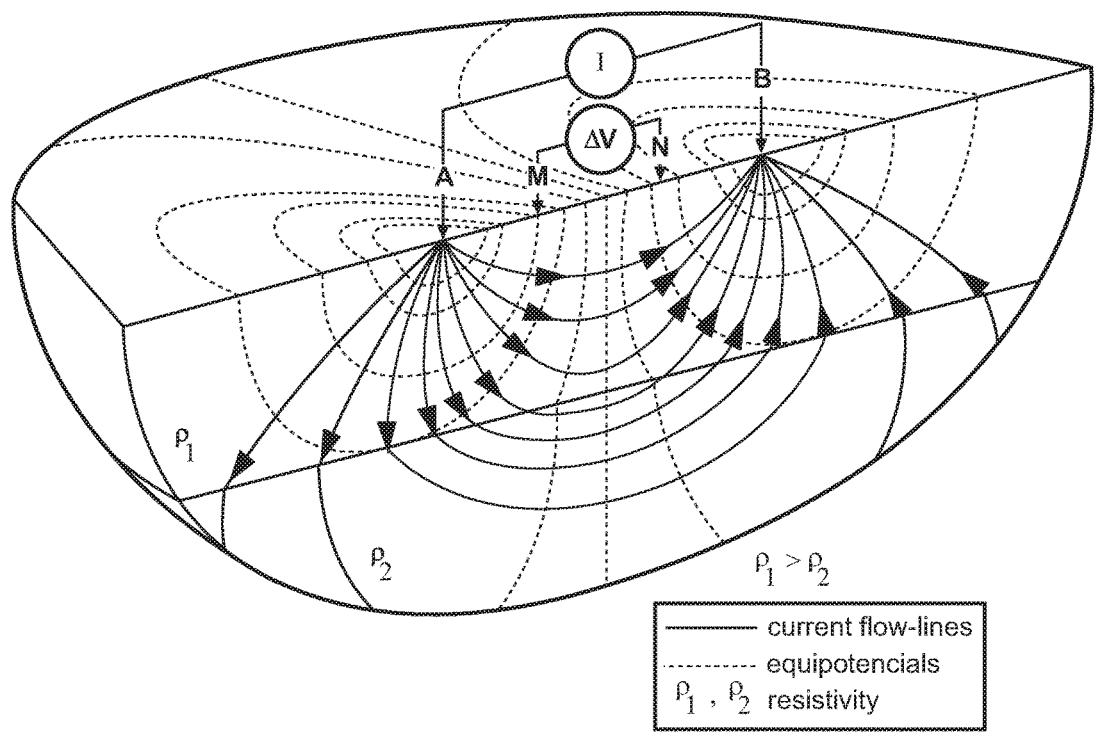
FIG. 6 is a cross-sectional diagram showing a field in underlying tissue produced by application of two electrodes to the skin, with two layers of tissue of different electrical resistivity.

Referring to FIG. 6, applying similar electrodes to a part of the body in which there are two layers of tissue of different electrical resistivity, such as fat and muscle, can produce a field such as that shown in FIG. 6. Layers of different tissue may act to refract and direct energy waves and be used for beam aiming and steering. An individual's tissue parameters may be measured and used to characterize the appropriate energy stimulation for a selected nerve.

Figure 7:
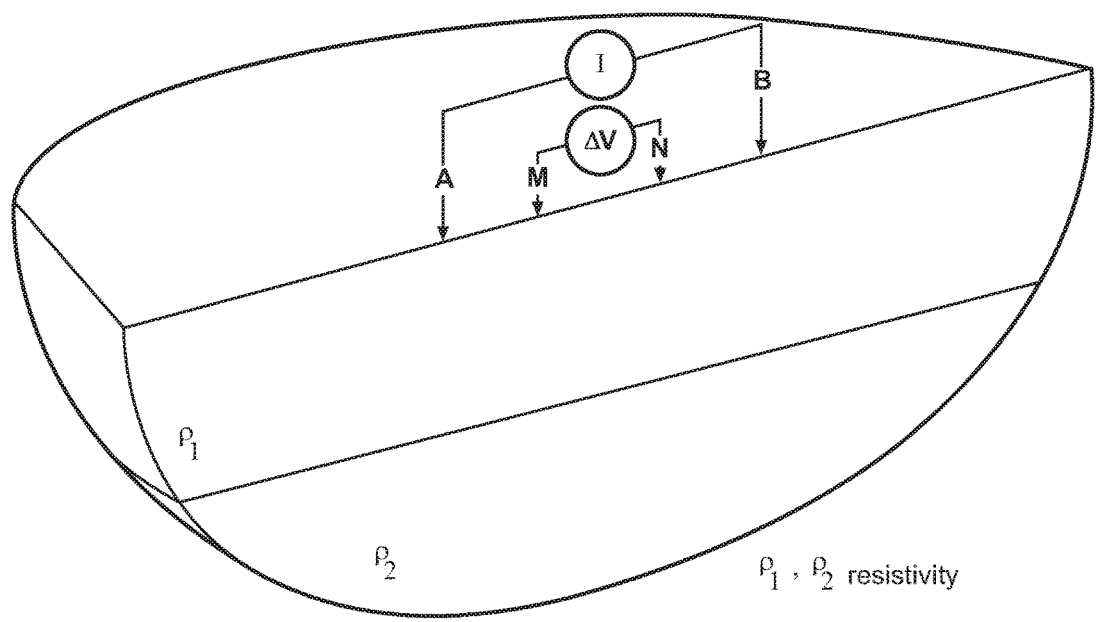
FIG. 7 is a cross-sectional diagram showing a field in underlying tissue when the stimulating pulse is turned off.

Referring to FIG. 7, when the stimulating pulse is turned off the electric field will collapse and the fields will be absent as shown.

It is the change in electric field that will cause an action potential to be created in a nerve cell, provided sufficient voltage and the correct orientation of the electric field occurs. More complex three-dimensional arrangements of tissues with different electrical properties can result in more complex three-dimensional electric fields, particularly since tissues have different electrical properties and these properties are different along the length of a tissue and across it, as shown in Table 1.

TABLE 1

| Electrical Conductivity (siemens/m) | Direction | Average |
|---|---|---|
| Blood | | .65 |
| Bone | Along | .17 |
| Bone | Mixed | .095 |
| Fat | | .05 |
| Muscle | Along | .127 |
| Muscle | Across | .45 |
| Muscle | Mixed | .286 |
| Skin (Dry) | | .000125 |
| Skin (Wet) | | .00121 |

Modification of Electric Fields by Tissue

An important factor in the formation of electric fields used to create action potentials in nerve cells is the medium through which the electric fields must penetrate. For the human body this medium consists of various types of tissue including bone, fat, muscle, and skin. Each of these tissues possesses different electrical resistivity or conductivity and different capacitance and these properties are anisotropic. They are not uniform in all directions within the tissues. For example, an axon has lower electrical resistivity along its axis than perpendicular to its axis. The wide range of conductivities is shown in Table 1. The three-dimensional structure and resistivity of the tissues will therefore affect the orientation and magnitude of the electric field at any given point in the body.

Modification of Electric Fields by Multiple Electrodes

Applying a larger number of electrodes to the skin can also produce more complex three-dimensional electrical fields that can be shaped by the location of the electrodes and the potential applied to each of them. Referring to FIG. 3, the pulse trains can differ from one another indicated by A, t/T, n, and f as well as have different phase relationships between the pulse trains. For example with an 8×8 array of electrodes, combinations of electrodes can be utilized ranging from simple dipoles, to quadripoles, to linear arrangements, to approximately circular configurations, to produce desired electric fields within tissues.

Applying multiple electrodes to a part of the body with complex tissue geometry will thus result in an electric field of a complex shape. The interaction of electrode arrangement and tissue geometry can be modeled using Finite Element Modeling, which is a mathematical method of dividing the tissues into many small elements in order to calculate the shape of a complex electric field. This can be used to design an electric field of a desired shape and orientation to a particular nerve.

High frequency techniques known for modifying an electric field, such as the relation between phases of a beam, cancelling and reinforcing by using phase shifts, may not apply to application of electric fields by TNSSs because they use low frequencies. Instead, the present system uses beam selection to move or shift or shape an electric field, also described as field steering or field shaping, by activating different electrodes, such as from an array of electrodes, to move the field. Selecting different combinations of electrodes from an array may result in beam or field steering. A particular combination of electrodes may shape a beam and/or change the direction of a beam by steering. This may shape the electric field to reach a target nerve selected for stimulation.

Activation of Nerves by Electric Fields

Usually in the past selectivity in activating nerves has required electrodes to be implanted surgically on or near nerves. Using electrodes on the surface of the skin to focus activation selectively on nerves deep in the tissues has many advantages. These include avoidance of surgery, avoidance of the cost of developing complex implants and gaining regulatory approval for them, and avoidance of the risks of long-term implants.

The features of the electric field that determine whether a nerve will be activated to produce an action potential can be modeled mathematically by the Activating Function described by Rattay (Rattay F. The basic mechanism for the electrical stimulation of the nervous system. Neuroscience Vol. 89, No. 2, pp. 335-346, 1999). The electric field can produce a voltage, or extracellular potential, within the tissues that varies along the length of a nerve. If the voltage is proportional to distance along the nerve, the first order spatial derivative will be constant and the second order spatial derivative will be zero. If the voltage is not proportional to distance along the nerve, the first order spatial derivative will not be constant and the second order spatial derivative will not be zero. The Activating Function is proportional to the second-order spatial derivative of the extracellular potential along the nerve. If it is sufficiently greater than zero at a given point it predicts whether the electric field will produce an action potential in the nerve at that point. This prediction may be input to a nerve signature.

In practice this means that electric fields that are varying sufficiently greatly in space or time can produce action potentials in nerves. These action potentials are also most likely to be produced where the orientation of the nerves to the fields change, either because the nerve or the field changes direction. The direction of the nerve can be determined from anatomical studies and imaging studies such as MRI scans. The direction of the field can be determined by the positions and configurations of electrodes and the voltages applied to them, together with the electrical properties of the tissues.

As a result it is possible to activate certain nerves at certain tissue locations selectively while not activating others.

To accurately control an organ or muscle, the nerve to be activated must be accurately selected. This selectivity may be improved by using the system described herein, and described herein as a nerve signature, in several ways, as follows:

Improved algorithms to control the effects when a nerve is stimulated, for example, by measuring the resulting electrical or mechanical activity of muscles and feeding back this information to modify the stimulation and measuring the effects again. Repeated iterations of this process can result in optimizing the selectivity of the stimulation, either by classical closed loop control or by machine learning techniques such as pattern recognition and artificial intelligence;

Improving nerve selectivity by labeling or tagging nerves chemically; for example, introduction of genes into some nerves to render them responsive to light or other electromagnetic radiation can result in the ability to activate these nerves and not others when light or electromagnetic radiation is applied from outside the body;

Improving nerve selectivity by the use of electrical conductors to focus an electric field on a nerve; these conductors might be implanted, but could be passive and much simpler than the active implantable medical devices currently used;

Improving nerve selectivity by the use of reflectors or refractors, either outside or inside the body, to focus a beam of electromagnetic radiation on a nerve. If these reflectors or refractors are implanted, they may be passive and much simpler than the active implantable medical devices currently used;

Improving nerve selectivity by the use of feedback from the person upon whom the stimulation is being performed; this may be an action taken by the person in response to a physical indication such as a muscle activation or a feeling from one or more nerve activations;

Improving nerve selectivity by the use of feedback from sensors associated with the TNSS, or separately from other sensors, that monitor electrical activity associated with the stimulation; and Improving nerve selectivity by the combination of feedback from both the person or sensors and the TNSS that may be used to create a unique profile of the user's nerve physiology for selected nerve stimulation.

Figure 8:
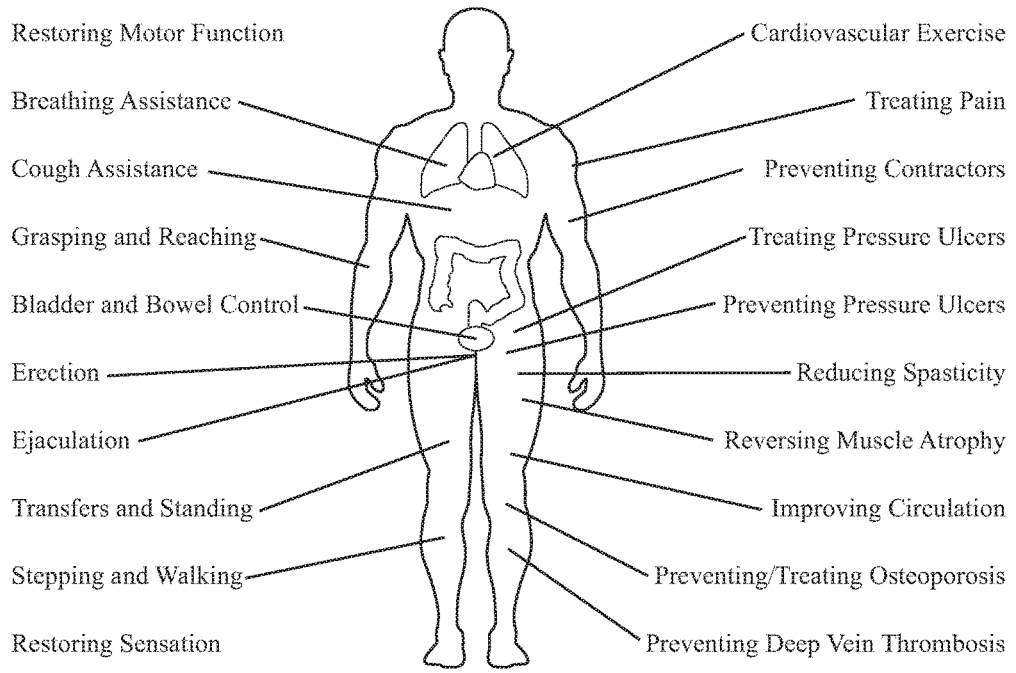
FIG. 8 shows potential applications of electrical stimulation to the body.

Potential applications of electrical stimulation to the body are shown in FIG. 8.

Logic Components

Figure 9A:
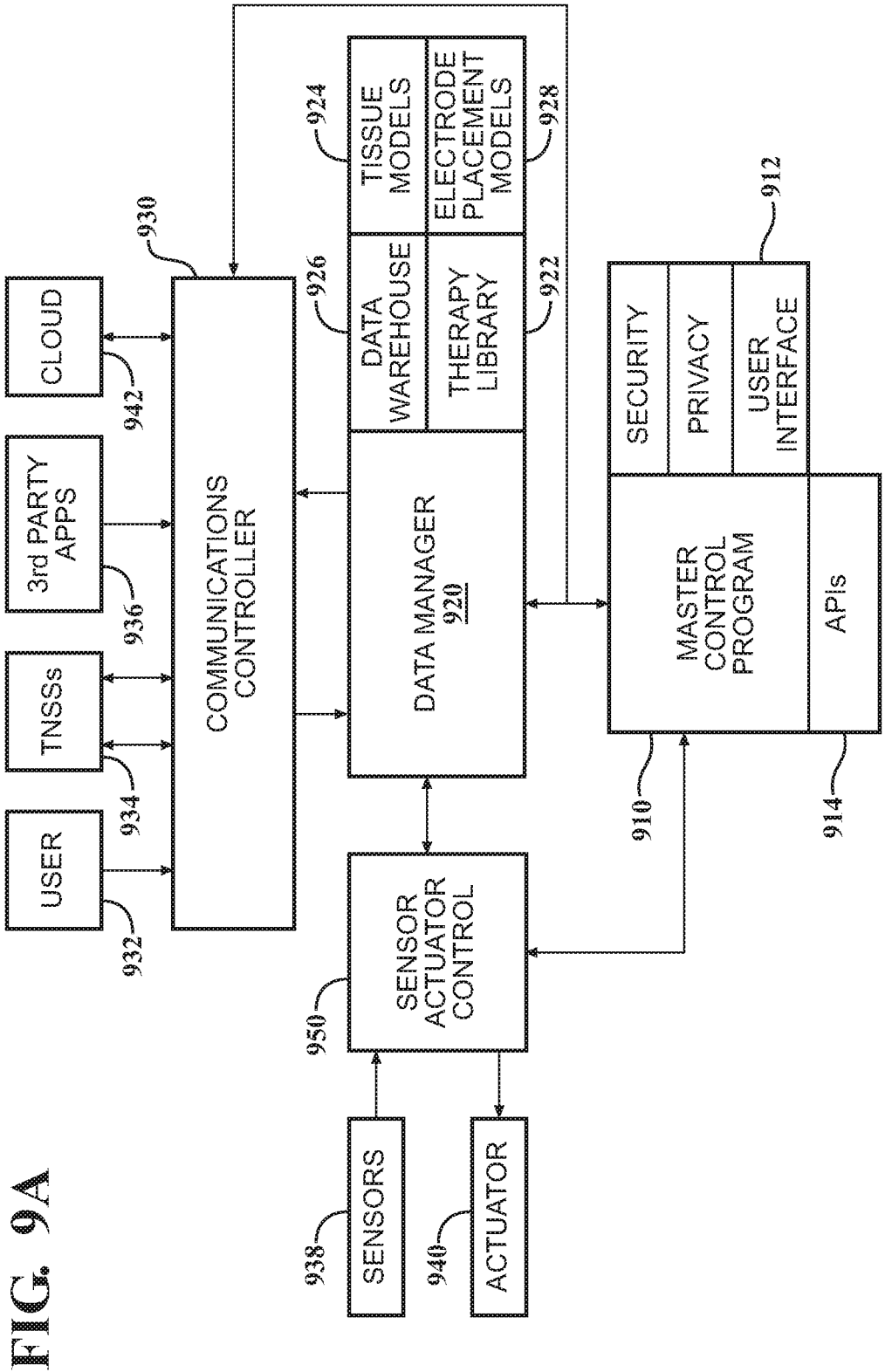
FIG. 9A is a system diagram of an example software and hardware components showing an example of a Topical Nerve Stimulator/Sensor (TNSS) interpreting a data stream from a control device.

Referring to FIG. 9A, the TNSS 934 human and mammalian interface and its method of operation and supporting system are managed by a Master Control Program (MCP) 910 represented in function format as block diagrams. It provides the logic for the nerve stimulator system.

Master Control Program

The primary responsibility of the MCP 910 is to coordinate the activities and communications among the various control programs, the Data Manager 920, the User 932, and the external ecosystem and to execute the appropriate response algorithms in each situation. The MCP 910 accomplishes electric field shaping and/or beam steering by providing an electrode activation pattern to the TNSS device 934 to selectively stimulate a target nerve. For example, upon notification by the Communications Controller 930 of an external event or request, the MCP 910 is responsible for executing the appropriate response, working with the Data Manager 920 to formulate the correct response and actions. It integrates data from various sources such as Sensors 938 and external inputs such as TNSS devices 934, and applies the correct security and privacy policies, such as encryption and HIPAA required protocols. It will also manage the User Interface (UI) 912 and the various Application Program Interfaces (APIs) 914 that provide access to external programs.

The MCP is also responsible for effectively managing power consumption by the TNSS device through a combination of software algorithms and hardware components that may include, among other things: computing, communications, and stimulating electronics, antenna, electrodes, sensors, and power sources in the form of conventional or printed batteries.

Communications Controller

The communications controller is responsible for receiving inputs from the User 932, from a plurality of TNSS devices 934, and from 3rd party apps 936 via communications sources such as Internet or cellular networks. The format of such inputs will vary by source and must be received, consolidated, possibly reformatted, and packaged for the Data Manager 920.

User inputs may consist of simple requests for activation of TNSS devices 934 to status and information concerning the User's 932 situation or needs. TNSS devices 934 will provide signaling data that may consist of voltage readings, TNSS 934 status data, responses to control program inquiries, and other signals. The Communications Controller 930 is also responsible for sending data and control requests to the plurality of TNSS devices 934. 3rd party applications 936 can send data, requests, or instructions for the Master Control Program 910 or User 932 via Internet or cellular networks. The Communications Controller 930 is also responsible for communications via the cloud where various software applications reside.

Data Manager

The Data Manager (DM) 920 has primary responsibility for the storage and movement of data to and from the Communications Controller 930, Sensors 938, Actuators 940, and the Master Control Program 910. The DM 920 has the capability to analyze and correlate any of the data under its control. It provides logic to select and activate nerves. Examples of such operations upon the data include: statistical analysis and trend identification; machine learning algorithms; signature analysis and pattern recognition, correlations among the data within the Data Warehouse 926, the Therapy Library 922, the Tissue Models 924, and the Electrode Placement Models 928, and other operations. There are several components to the data that is under its control as described in the following paragraphs.

The Data Warehouse (DW) 926 is where incoming data is stored; examples of this data can be real-time measurements from TNSS devices 934 or from Sensors (938), data streams from the Internet, or control and instructional data from various sources. The DM 920 will analyze data, as specified above, that is held in the DW 926 and cause actions, including the export of data, under MCP 910 control. Certain decision making processes implemented by the DM 920 will identify data patterns both in time, frequency, and spatial domains and store them as signatures for reference by other programs. Techniques like EMG, even multi-electrode EMG, gather a lot of data that is the sum of hundreds to thousands of individual motor units and the normal procedure is to perform complex decomposition analysis on the total signal to attempt to tease out individual motor units and their behavior. The DM 920 will perform big data analysis over the total signal and recognize patterns that relate to specific actions or even individual nerves or motor units. This analysis can be performed over data gathered in time from an individual, or over a population of TNSS Users.

The Therapy Library 922 contains various control regimens for the TNSS devices 934. Regimens specify the parameters and patterns of pulses to be applied by the TNSS devices 934. The width and amplitude of individual pulses may be specified to stimulate nerve axons of a particular size selectively without stimulating nerve axons of other sizes. The frequency of pulses applied may be specified to modulate some reflexes selectively without modulating other reflexes. There are preset regimens that may be loaded from the Cloud 942 or 3rd party apps 936. The regimens may be static read-only as well as adaptive with read-write capabilities so they can be modified in real-time responding to control signals or feedback signals or software updates. Referring to FIG. 3 one such embodiment of a regimen has parameters A=40 volts, t=500 microseconds, T=1 millisecond, n=100 pulses per group, and f=20 per second. Other embodiments of regimens will vary the parameters within ranges previously specified.

The Tissue Models 924 are specific to the electrical properties of particular body locations where TNSS devices 934 may be placed. As noted previously, electric fields for production of action potentials will be affected by the different electrical properties of the various tissues that they encounter. Tissue Models 924 are combined with regimens from the Therapy Library 922 and Electrode Placement Models 928 to produce desired actions. Tissue Models 924 may be developed by MRI, Ultrasound or other imaging or measurement of tissue of a body or particular part of a body. This may be accomplished for a particular User 932 and/or based upon a body norm. One such example embodiment of a desired action is the use of a Tissue Model 924 together with a particular Electrode Placement Model 928 to determine how to focus the electric field from electrodes on the surface of the body on a specific deep location corresponding to the pudendal nerve in order to stimulate that nerve selectively to reduce incontinence of urine. Other example embodiments of desired actions may occur when a Tissue Model 924 in combination with regimens from the Therapy Library 22 and Electrode Placement Models 928 produce an electric field that stimulates a sacral nerve. Many other embodiments of desired actions follow for the stimulation of other nerves.

Electrode Placement Models 928 specify electrode configurations that the TNSS devices 934 may apply and activate in particular locations of the body. For example, a TNSS device 934 may have multiple electrodes and the Electrode Placement Model 928 specifies where these electrodes should be placed on the body and which of these electrodes should be active in order to stimulate a specific structure selectively without stimulating other structures, or to focus an electric field on a deep structure. An example embodiment of an electrode configuration is a 4 by 4 set of electrodes within a larger array of multiple electrodes, such as an 8 by 8 array. This 4 by 4 set of electrodes may be specified anywhere within the larger array such as the upper right corner of the 8 by 8 array. Other example embodiments of electrode configurations may be circular electrodes that may even consist of concentric circular electrodes. The TNSS device 934 may contain a wide range of multiple electrodes of which the Electrode Placement Models 928 will specify which subset will be activated. These Electrode Placement Models 928 complement the regimens in the Therapy Library 922 and the Tissue Models 924 and are used together with these other data components to control the electric fields and their interactions with nerves, muscles, tissues and other organs. Other examples may include TNSS devices 934 having merely one or two electrodes, such as but not limited to those utilizing a closed circuit.

Sensor/Actuator Control

Independent sensors 938 and actuators 940 can be part of the TNSS system. Its functions can complement the electrical stimulation and electrical feedback that the TNSS devices 934 provide. An example of such a sensor 938 and actuator 940 include, but are not limited to, an ultrasonic actuator and an ultrasonic receiver that can provide real-time image data of nerves, muscles, bones, and other tissues. Other examples include electrical sensors that detect signals from stimulated tissues or muscles. The Sensor/Actuator Control module 950 provides the ability to control both the actuation and pickup of such signals, all under control of the MCP 910.

Application Program Interfaces

The MCP 910 is also responsible for supervising the various Application Program Interfaces (APIs) that will be made available for 3rd party developers. There may exist more than one API 914 depending upon the specific developer audience to be enabled. For example many statistical focused apps will desire access to the Data Warehouse 926 and its cumulative store of data recorded from TNSS 934 and User 932 inputs. Another group of healthcare professionals may desire access to the Therapy Library 922 and Tissue Models 924 to construct better regimens for addressing specific diseases or disabilities. In each case a different specific API 914 may be appropriate.

The MCP 910 is responsible for many software functions of the TNSS system including system maintenance, debugging and troubleshooting functions, resource and device management, data preparation, analysis, and communications to external devices or programs that exist on the smart phone or in the cloud, and other functions. However, one of its primary functions is to serve as a global request handler taking inputs from devices handled by the Communications Controller 930, external requests from the Sensor Control Actuator Module (950), and 3rd party requests 936.

Examples of High Level Master Control Program (MCP) functions are set forth in the following paragraphs.

Figure 9B:
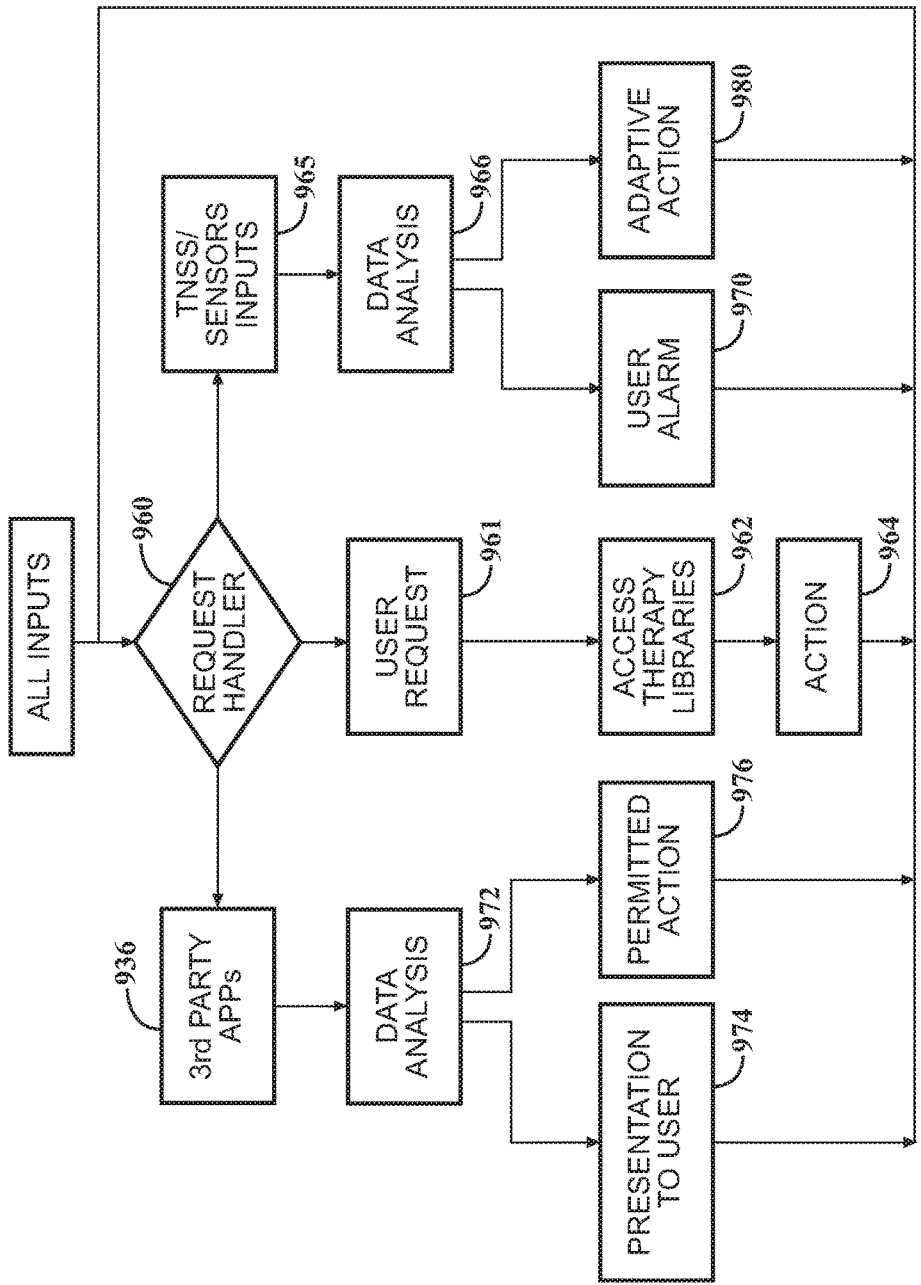
FIG. 9B is a flow chart showing an example of a function of a master control program.

The manner in which the MCP handles these requests is shown in FIG. 9B. The Request Handler (RH) 960 accepts inputs from the User 932, TNSS devices 934, 3rd party apps 936, sensors 938 and other sources. It determines the type of request and dispatches the appropriate response as set forth in the following paragraphs.

User Request: The RH 960 will determine which of the plurality of User Requests 961 is present such as: activation; display status, deactivation, or data input, e.g. specific User condition. Shown in FIG. 9B is the RH's 960 response to an activation request. As shown in block 962, RH 960 will access the Therapy Library 922 and cause the appropriate regimen to be sent to the correct TNSS 934 for execution, as shown at block 964 labeled "Action."

TNSS/Sensor Inputs: The RH 960 will perform data analysis over TNSS 934 or Sensor inputs 965. As shown at block 966, it employs data analysis, which may include techniques ranging from DSP decision making processes, image processing algorithms, statistical analysis and other algorithms to analyze the inputs. In FIG. 9B two such analysis results are shown; conditions which cause a User Alarm 970 to be generated and conditions which create an Adaptive Action 980 such as causing a control feedback loop for specific TNSS 934 functions, which of course can iteratively generate further TNSS 934 or Sensor inputs 965 in a closed feedback loop.

3rd Party Apps: Applications can communicate with the MCP 910, both sending and receiving communications. A typical communication would be to send informational data or commands to a TNSS 934. The RH 960 will analyze the incoming application data, as shown at block 972. FIG. 9B shows two such actions that result. One action, shown at block 974 would be the presentation of the application data, possibly reformatted, to the User 932 through the MCP User Interface 912. Another result would be to perform a User 932 permitted action, as shown at 976, such as requesting a regimen from the Therapy Library 922.

Figure 10:
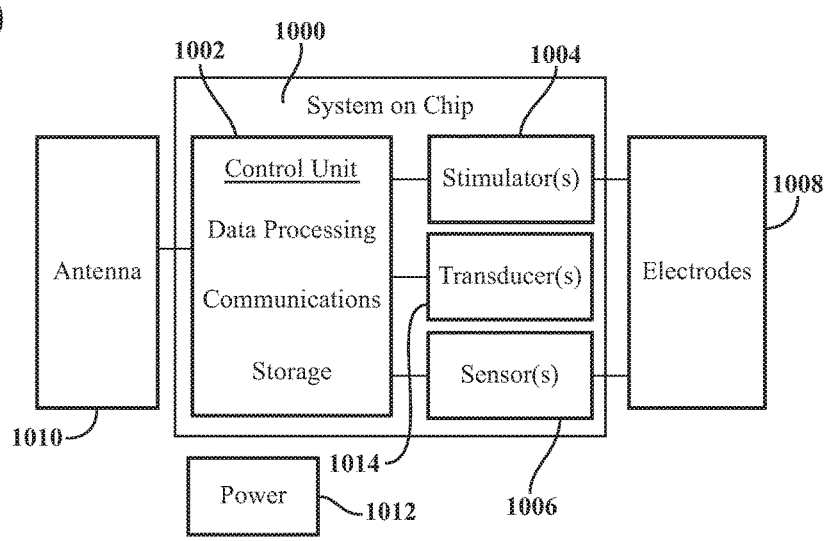
FIG. 10 is a block diagram of an example TNSS component configuration including a system on a chip (SOC)

Referring to FIG. 10, an example TNSS is shown. The TNSS has one or more electronic circuits or chips 1000 that perform the functions of: communications with the controller, nerve stimulation via one or more electrodes 1008 that produce a wide range of electric field(s) according to treatment regimen, one or more antennae 1010 that may also serve as electrodes and communication pathways, and a wide range of sensors 1006 such as, but not limited to, mechanical motion and pressure, temperature, humidity, chemical and positioning sensors. In another example, TNSS interfaces to transducers 1014 to transmit signals to the tissue or to receive signals from the tissue.

One arrangement is to integrate a wide variety of these functions into an SOC, system on chip 1000. Within this is shown a control unit 1002 for data processing, communications, transducer interface and storage and one or more stimulators 1004 and sensors 1006 that are connected to electrodes 1008. An antenna 1010 is incorporated for external communications by the control unit. Also present is an internal power supply 1012, which may be, for example, a battery. An external power supply is another variation of the chip configuration. It may be necessary to include more than one chip to accommodate a wide range of voltages for data processing and stimulation. Electronic circuits and chips will communicate with each other via conductive tracks within the device capable of transferring data and/or power.

The TNSS interprets a data stream from the control device, such as that shown in FIG. 9A, to separate out message headers and delimiters from control instructions. In one arrangement, control instructions contain information such as voltage level and pulse pattern. The TNSS activates the stimulator 1004 to generate a stimulation signal to the electrodes 1008 placed on the tissue according to the control instructions. In another arrangement the TNSS activates a transducer 1014 to send a signal to the tissue. In another embodiment, control instructions cause information such as voltage level and pulse pattern to be retrieved from a library stored in the TNSS.

The TNSS receives sensory signals from the tissue and translates them to a data stream that is recognized by the control device, such as the example in FIG. 9A. Sensory signals include electrical, mechanical, acoustic, optical and chemical signals among others. Sensory signals come to the TNSS through the electrodes 1008 or from other inputs originating from mechanical, acoustic, optical, or chemical transducers. For example, an electrical signal from the tissue is introduced to the TNSS through the electrodes 1008, is converted from an analog signal to a digital signal and then inserted into a data stream that is sent through the antenna 1010 to the control device. In another example an acoustic signal is received by a transducer 1014 in the TNSS, converted from an analog signal to a digital signal and then inserted into a data stream that is sent through the antenna 1010 to the control device. In certain cases sensory signals from the tissue are directly interfaced to the control device for processing.

Application to Bladder Control

Figure 11:
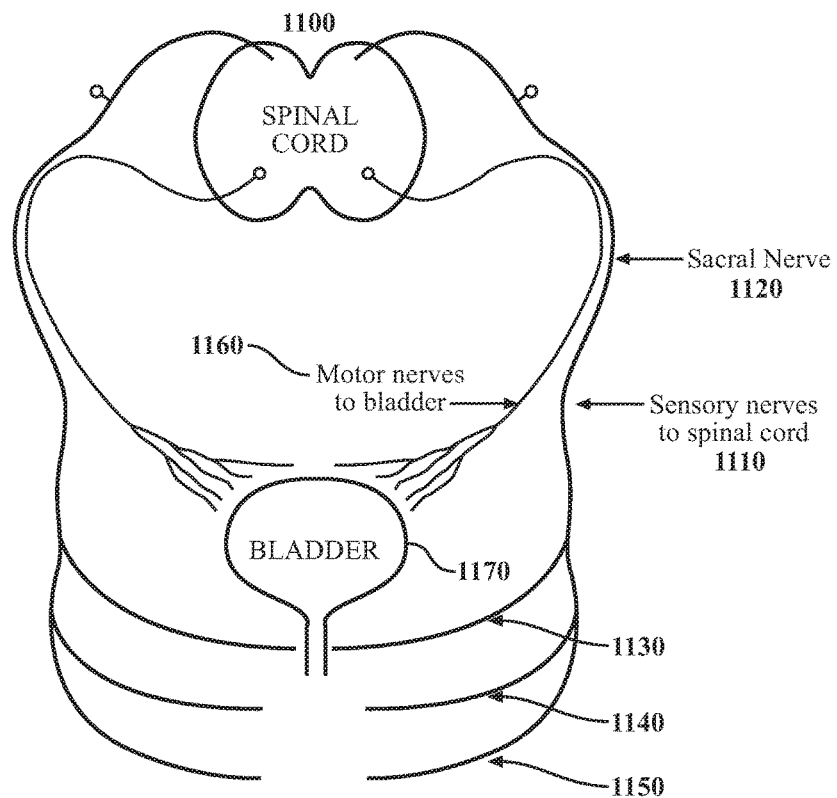
FIG. 11 is a nerve diagram showing the nerve signals related to bladder function.

Bladder function may be modified directly or indirectly using the principles described above. Referring to FIG. 11, in some cases, electrical stimulation of sacral sensory nerves 1110 causes action potentials that travel to the spinal cord 1100 where they reduce the activity in motor nerves 1160 from the spinal cord back to the bladder 1170, producing relaxation of the bladder. This is known as reflex inhibition of the bladder and is one form of neuromodulation. Reduction of unwanted bladder contraction may provide useful function such as reduced urgency in needing to pass urine, reduced frequency of passing urine and reduced urge incontinence of urine. This pattern of symptoms is sometimes considered as a syndrome called Over Active Bladder.

In other cases, electrical stimulation of these sensory nerves causes action potentials that travel to the spinal cord 1100 where they reduce the activity in motor nerves from the spinal cord to the sphincter, allowing relaxation of the sphincter. This form of neuromodulation can reduce unwanted contraction of the sphincter and provide useful function such as reduced straining to pass urine, an improved stream of urine and more complete bladder emptying, for example in a condition known as Fowler's Syndrome.

In other cases, electrical stimulation of sacral sensory nerves 1110 causes action potentials that travel to the spinal cord 1100 where they increase the activity in nerves from the spinal cord to the internal and external urethral sphincters, producing contraction of these sphincter muscles that surround the exit of the bladder. In other cases, electrical stimulation of motor axons in the pudendal nerve 1130 to the external urethral sphincter muscle can produce contraction of that muscle. Whether the contraction of the sphincters is produced indirectly, as a reflex response to stimulation of sensory nerves, or directly, as a response to stimulation of motor nerves, it can reduce incontinence or leaking of urine, for example during straining, coughing or sneezing. This may benefit some people with stress incontinence.

Electrodes can be applied to the skin on the back of the penis in proximity to the dorsal penile nerve 1140, or to the skin on or near the back of the clitoris in proximity to the dorsal clitoral nerve, at the base of the spine or other sites around the pelvis in proximity to the sacral nerves 1120 or their branches and tributaries or the pudendal nerves 1130 or their branches and tributaries, or the back of the lower leg adjacent to the posterior tibial nerve 1150.

The electrodes are typically used in pairs to apply electrical stimuli in the form of square waves having amplitudes of between 20 and 100 volts, pulse widths of between 100 and 500 microseconds, and a pulse repetition rate of between 3 and 30 pulses per second.

Non-invasive methods of directing or focusing electrical stimulation from electrodes on the surface of the skin towards nerves deeper in the body may also be used to allow selective stimulation of deep nerves such as the sacral nerves 1120 or pudendal nerves 1130 without the need for surgical implantation of electrodes or stimulators.

The electrodes on the surface of the skin are connected to or part of a Topical Nerve Stimulator and Sensor (TNSS) 934 (FIG. 9A).

Operation

Figure 12:
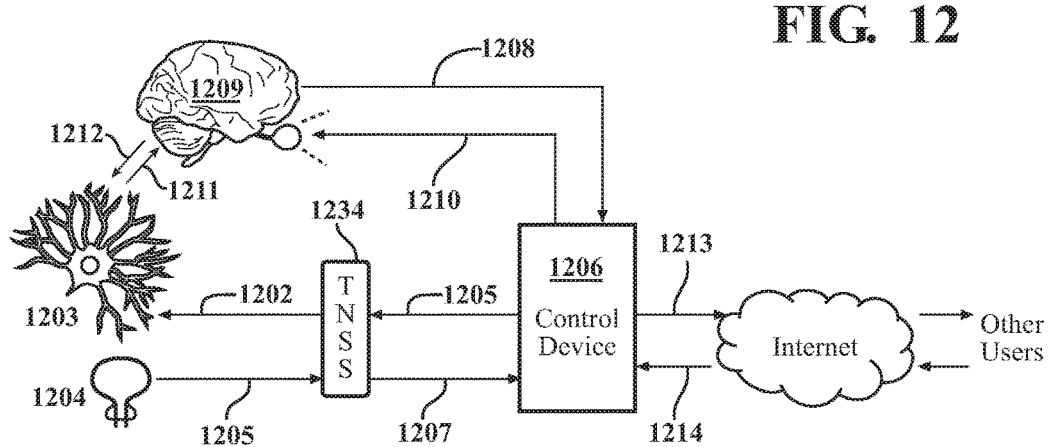
FIG. 12 is a system diagram showing an example TNSS system.

The stimulator may be operated voluntarily by the user or may be operated automatically in response to signals from sensors in the TNSS or elsewhere in a TNSS system shown in FIG. 12.

Voluntary Operation by the User for Control of Over Active Bladder or Urge Incontinence As the bladder 1204 fills, there are usually signals transmitted by sensory nerves 1211 to the brain 1209 resulting in awareness by the user of a sensation of bladder fullness, or an urge to pass urine, or a fear of incontinence; these sensations may or may not be associated with contraction of the bladder.

When these sensations are felt, the user can press a button on the TNSS 934 (FIG. 9A) or a Control Device 1206 which may be a smartphone or a dedicated device. A dedicated device is a small portable device resembling a key fob and containing electronic circuits for storage and operation of programs and buttons that the user can operate. When the user presses a button on the Control Device this can cause it to transmit radio-frequency signals to the TNSS to control the operation of the TNSS. The Control Device can also receive radio-frequency signals from the TNSS 934 (FIG. 9A).

The TNSS 934 (FIG. 9A) and the Control Device are under software control, responding to actions from the user. There will be safeguards to prevent false activations or unnecessary repetitive activations. The activation by the user causes a stimulator in the TNSS 934 (FIG. 9A) to send electrical stimulation signals 1202 to activate nerves 1203 affecting the bladder and sphincter, such as pudendal nerves 1130 (FIG. 11), dorsal genital nerves 1140, posterior tibial nerves 1150 or other nerves, as described above.

The TNSS 934 (FIG. 9A) can stimulate the appropriate nerve(s) to relax the bladder. This stimulation can be with a preset pulse signal, or the user can select from variety of pulse signals, and their intensities; this might be implemented as one or more of a plurality of virtual buttons on the interface of a smartphone or physical buttons on a dedicated device. The user selects from programs to deal with a weak urge, a moderate urge, or a strong urge; the programs may provide an intermittent or a continuous pulse signal and the signal may have a timeout of a duration chosen by the user. The user can reactivate the TNSS 934 either immediately if the urge is not completely abated, or the next time he/she feels the urge to urinate.

Voluntary Operation by the User for Control of Stress Incontinence

When a user becomes aware that they are about to engage in an activity such as straining, coughing or sneezing that may cause stress incontinence, the user can press a button on the TNSS 934 or a control device 1206 to cause electrical stimulation of sacral sensory or motor nerves to produce reflex or direct activation of the urethral sphincters. The contraction of these sphincters may reduce stress incontinence.

Automatic Operation for Control of Over Active Bladder or Urge Incontinence

In some cases it will be possible to control the urge to empty the bladder automatically, without the intervention of the user. The normal feedback to cause the TNSS 934 to be activated for this purpose comes from the user's perception of an urge to urinate, which is communicated to the control device 1206 as described previously. There is a plurality of other non-invasive portable methods of obtaining feedback that can control the bladder in parallel with or separately from this feedback. For example, the TNSS 934 may include an acoustic transceiver that can send an acoustic pulse into the body and detect acoustic echoes from the pelvic region indicating bladder position, shape or volume, or a sensor of bladder pressure may transmit a signal to the TNSS 934 or control device 1206.

The TNSS 934 will then automatically stimulate bladder nerves as described above to inhibit bladder contraction before the user becomes aware of the urge. This automatic mode of operation will make use of the various feedback loops shown in FIG. 12. For example, the state of the bladder 1204 may be sensed and transmitted 1205 to the TNSS 934, which may act upon the signal to send a signal 1202 to stimulate the nerves 1203 that control the bladder 1204. The TNSS 934 may also send signals 1207 to a control device 1206 that can respond with signals 1205 to control the TNSS 934. The control device 1206 may also send signals 1210 to the user who may respond with signals 1208 to modify the actions of the control device 1206. The control device 1206 may also send signals 1213 via the Internet to other users who may respond with signals 1214 to modify the actions of the control device 1206.

Automatic Operation for Control of Stress Incontinence

In some cases it will be possible to reduce stress incontinence automatically, without the intervention of the user. The normal feedback to cause the TNSS 934 to be activated for this purpose comes from the user's awareness that they are about the engage in an activity that may cause stress incontinence. There is a plurality of other methods of obtaining feedback that can control the sphincters in parallel with or separately from this feedback. For example, sensors and associated pattern recognition software may detect a pattern of activity indicating an impending sneeze, cough or episode of straining. The control device 1206 and TNSS 934 will then automatically stimulate nerves to cause sphincter contraction and reduce stress incontinence.

Adaptive Operation

With training using data from one or many individuals, software in the TNSS 934 or in the control device 1206 or in other computing systems available via the internet may use machine learning to recognize patterns in time or space and improve determination of when incontinence is about to occur.

There may be additional functions in addition to the operations described above. These include logging functions, incorporating data from the cloud, and data from other sensors and sources.

Upon activation of the TNSS 934 one or more of the following functions can occur.

The user's activation profile is recorded by the TNSS 934 and shared with the control device 1206. The activation profile consists of a User ID, stimulation signal identifier and stimulus parameters, date and time of day, and if the user interface permits, user conditions at the time of activation. Historical data can be gathered and analyzed for the user's benefit.

The control device 1206 and/or the TNSS 934 may accept data from other users via the Internet. Types of data may be instructions from a healthcare professional, population data, statistical analyses and trend data relative to the individual user or across populations. This data can be passed through to the user, or cause actions to be taken, such as alarms or notifications.

Data can be gathered from other sensors, from other sensors, which may be located in the TNSS 1401, in the control device, and other patches, or in other devices, on a continuous basis or only when the TNSS 934 is activated. When the TNSS 934 is activated, these data can be used to alter or modify the stimulation signals that the TNSS 934 transmits to the user. An example would be an acoustic transceiver that may be implemented in MEMS that can both transmit and receive acoustic data to create acoustic images of the bladder and pelvic region. This would allow the TNSS 934 to gather image data of the pelvic region over time and learn the state of bladder, as compared to historical conditions.

The invention claimed is:

1. A method of modifying bladder function of a user comprising:

applying a dermal patch on an external surface of a skin of the user on a lower leg of the user adjacent to a tibial nerve, the dermal patch comprising electrodes, a sensor, communications, a control unit and a stimulator, the electrodes, the sensor, the communications, the control unit and the stimulator integral to the dermal patch;

automatically determining a state of a bladder of the user using the sensor;

determining an electrical stimulation corresponding to the tibial nerve, by the control unit of the dermal patch, the control unit processing instructions comprising:

in response to the automatically determined state of the bladder, automatically initiating an applying, without user intervention, on the external surface of the skin, of the electrical stimulation by the electrodes and the stimulator to produce an electric field; and selectively activating the tibial nerve by the electric field using the electrodes on the external surface of the skin to inhibit a contraction of the bladder.

2. The method of claim 1, further comprising applying the dermal patch in the proximity of a sacral or pudendal nerve.

3. The method of claim 1, the dermal patch comprising a system on a chip that includes the control unit, the electrodes and the stimulator and determining a subset of the electrodes that are active by the selectively activating, the subset of electrodes less than all of the electrodes that are integral to the dermal patch, the determining based on a determination of a type of nerve to be stimulated.

4. The method of claim 1, further comprising applying the dermal patch in the proximity of a branch or tributary of the tibial nerve.

5. The method of claim 1, the electric stimulation comprising square waves having an amplitude between 20 and 100 volts, pulse widths between 100 and 500 microseconds, and a pulse repetition rate of between 3 and 30 pulses per second.

6. The method of claim 1, the state of the bladder indicating an urge to urinate by the user and the automatically initiating the applying occurring before the user is aware of the urge.

7. The method of claim 1, further comprising sensing physiological feedback based upon the activation of the stimulator and activating the electrodes based at least in part on the feedback.

8. The method of claim 1, further comprising selecting from a plurality of pulse strengths or pulse types and applying the stimulation in accordance with the selected pulse strength or pulse type.

9. The method of claim 1, further comprising the electric field targeting a urethral sphincter for reflex or direct activation.

10. The method of claim 1, further comprising modifying stress incontinence, overactive bladder incontinence or urge incontinence.

11. The method of claim 1, the automatically determining the state of the bladder comprising detecting by an acoustic transceiver integral to the dermal patch an acoustic echo from a pelvic region indicating a position of a bladder, a shape of the bladder or a volume of the bladder; and
automatically activating the electrodes, by the stimulator, to inhibit bladder contraction based at least in part on the acoustic echo.

12. The method of claim 1, further comprising modifying the stimulation based upon a manual input received at a wireless device wirelessly connected to the dermal patch or a sensor input.

13. The method of claim 1, the automatically determining the state of the bladder of the user comprising: sensing a physiological pattern of activity indicating an impending sneeze, cough or episode of straining.

14. The method of claim 1, further comprising:
recording by the dermal patch an activation profile;
assimilating a plurality of activation profiles for multiple dermal patches by wireless communication from the dermal patch to a remote controller;
analyzing the activation profiles by the controller;
communicating the activation profile analysis results by the controller wirelessly to the dermal patch; and
modifying the stimulation based at least in part on the activation profile analysis results.

15. A bladder control system for modifying bladder function of a user, the system comprising:
a dermal patch configured to be applied on an external surface of a skin of the user on a lower leg of the user adjacent to a tibial nerve, comprising electrodes, a sensor, communications, a control unit and a stimulator, the electrodes, the sensor, the communications, the control unit and the stimulator integral to the dermal patch;
the control unit processing instructions that, when executed, configure the control unit to:
automatically determine a state of a bladder of the user using the sensor;
determine an electrical stimulation corresponding to the tibial nerve;
in response to the automatically determined state of the bladder, automatically initiate an applying, without user intervention, on the external surface of the skin, the electrical stimulation by the electrodes and the stimulator to produce an electric field; and
selectively activating the tibial nerve by the electric field using the electrodes on the external surface of the skin to inhibit a contraction of the bladder.

16. The bladder control system of claim 15, the dermal patch comprising a system on a chip that includes the control unit, the electrodes and the stimulator, the control unit further configured to determining a subset of the electrodes that are active by the selectively activating, the subset of electrodes less than all of the electrodes that are integral to the dermal patch, the determining based on a determination of a type of nerve to be stimulated.

17. The bladder control system of claim 15, the control unit further configured to receive a manual command received from a wireless device to activate the stimulator.

18. The bladder control system of claim 15, the control unit further configured to sense physiological feedback based upon the activation of the stimulator and activating the electrodes based at least in part on the feedback.

19. The bladder control system of claim 15, the electric stimulation comprising square waves having an amplitude between 20 and 100 volts, pulse widths between 100 and 500 microseconds, and a pulse repetition rate of between 3 and 30 pulses per second.

20. The bladder control system of claim 15, the state of the bladder indicating an urge to urinate by the user and the automatically initiate the applying occurring before the user is aware of the urge.

* * * * *